(12) United States Patent
Moll et al.

(10) Patent No.: US 8,703,460 B2
(45) Date of Patent: Apr. 22, 2014

(54) METHOD FOR THE PRODUCTION OF AN ADDITIVE FOR THE ENZYMATIC DECOMPOSITION OF MYCOTOXINS, ADDITIVE, AND USE THEREOF

(75) Inventors: Wulf-Dieter Moll, Stockerau (AT); Doris Hartinger, Vienna (AT); Karin Grießler, Pottenbrunn (AT); Eva Maria Binder, Tulln (AT); Gerd Schatzmayr, Tulln (AT)

(73) Assignee: Erber Aktiengesellschaft, Herzogenburg (AT)

( * ) Notice: Subject to any disclaimer, the term of this patent is extended or adjusted under 35 U.S.C. 154(b) by 3 days.

(21) Appl. No.: 12/998,061

(22) PCT Filed: Sep. 18, 2009

(86) PCT No.: PCT/AT2009/000364
§ 371 (c)(1),
(2), (4) Date: Apr. 18, 2011

(87) PCT Pub. No.: WO2010/031101
PCT Pub. Date: Mar. 25, 2010

(65) Prior Publication Data
US 2011/0189755 A1    Aug. 4, 2011

(30) Foreign Application Priority Data
Sep. 18, 2008   (AT) ................. GM501/2008

(51) Int. Cl.
| | |
|---|---|
| *C12N 9/10* | (2006.01) |
| *C12N 9/18* | (2006.01) |
| *C12N 9/80* | (2006.01) |
| *A61K 8/00* | (2006.01) |
| *C07H 21/04* | (2006.01) |

(52) U.S. Cl.
USPC ............ 435/193; 435/197; 435/228; 426/63; 536/23.2

(58) Field of Classification Search
None
See application file for complete search history.

(56) References Cited

U.S. PATENT DOCUMENTS 6,538,177 B1 *   3/2003   Duvick et al. ................. 800/279

FOREIGN PATENT DOCUMENTS

| WO | 99/02703 | 1/1999 |
|---|---|---|
| WO | 00/04158 | 1/2000 |
| WO | 00/04160 | 1/2000 |
| WO | 2004/085624 | 10/2004 |
| WO | 2006/053357 | 5/2006 |

OTHER PUBLICATIONS

D. Hartinger et al., "Heterologous expression of genes from the fumonisin degradation gene cluster of *Sphingomonas* spp. MTA144 and activity of the catabolic enzymes," New Biotechnology, Aug. 13, 2009, vol. 25, Supplement 1, pp. S132-S133.

S. Heinl et al., "Identification of a fumonisin B1 degrading gene cluster in *Sphingomonas* spp. MTA144," New Biotechnology, Aug. 13, 2009, vol. 25, Supplement 1, pp. S61-S62.

S. Heinl et al., "Degradation of fumonisin B1 by the consecutive action of two bacterial enzymes," Journal of Biotechnology, 2010, vol. 145, pp. 120-129.

* cited by examiner

*Primary Examiner* — Iqbal H Chowdhury
(74) *Attorney, Agent, or Firm* — Jacobson Holman PLLC

(57) ABSTRACT

In a method for producing an additive for the enzymatic degradation of mycotoxins, in particular fumonisins, it is provided that at least one nucleic acid sequence of genes corresponding to sequences ID Nos. 1, 2, 4, 6, 8, 10, 12, 14, 16, 18, 20, 22 and 24 is provided, the at least one nucleic acid sequence is expressed in prokaryotic or eukaryotic host cells, and at least one thus prepared enzyme corresponding to sequences ID Nos. 3, 5, 7, 9, 11, 13, 15, 17, 19, 21, 23 and 25, or at least one complete recombinant host organism optionally along with a cosubstrate, are used in a vegetable raw material.

14 Claims, 3 Drawing Sheets

SEQUENCE LISTING

```
<160> NUMBER OF SEQ ID NOS: 25

<210> SEQ ID NO 1
<211> LENGTH: 15420
<212> TYPE: DNA
<213> ORGANISM: Sphingopyxis sp.
<220> FEATURE:
<223> OTHER INFORMATION: Seq ID 1 (fum)

<400> SEQUENCE: 1
tgtcggcgat crgtaaactt ctaccgtggt cctcgttcgc ccacakcata catcacagac      60
rtcgggattt ccaactgaac gggtcccggc ctgccggccc acatttcccg gaacgccata     120
tgggtgattt cgacaatccg gttccaggcg aagatgggtg cgccccattt aaccgcgggt     180
cgaaagaggt cgatctggtc ttgtccctga aaggtttttg gcgtgcaggg ataaacgaca     240
ccaagttgat gctgggacgt tattgcgacg aagggaaccc cttcgtggcg tgccgtcacg     300
actccaggca gaaggtttgc cgtaccggga cccggattcg tgacaatcgc ggcgacctgt     360
```

```
ccggtggtct tgtaaatgcc ctcggccata taggctgcgg cggcctcgtg ccgcaccggg    420
acgaacaata tcccattgtc ttcgagcgca gccaggagcg gatccacctc cggcgacatg    480
aggccgaaga cataccggac gccttcgacg gccaaacatc gtgccaataa ttctccgccc    540
gtgaggcgca tgacgatctc cagtacgaaa ggtgagtgcc caggttccgg cacattcgct    600
gtggttagtt gatgcgctga tcggccaacc gactgagtgg agttggatgg ccgcacctta    660
ccctgtcgcg cataactctc agatccgaaa acggaccccg acattaaaat agcggccgac    720
cggatcatag gcagagctgg tcgggctgga aaaactgctg gggtcgttcg tcgctattgg    780
cggatctcgg tcgaacaaat tattgaccga tagaaacagc tgctgcttct ggccaaaagc    840
cgcgatgtcg aaggtcaatg tcgcgtcggt gtaccaaacc gccggagcgt ggttcaaatt    900
cgtatcgacg ccctccacat tgtcggcatt gaacaccgat gctgcgatga agcgctgctg    960
cacgagaagc gcccaatcgt cggtcgaata tcgcgcctgg aagttggccg accattttgg   1020
cgtgtccggt tgtccgagcg aacggatggg cgccgagccg gtcgcgatgc gataggcaga   1080
ggtatggtgc gttgccagcg cacgaagact gaacgtgccg ccgccgacgg ggcgtgagta   1140
ataggcctcg aagtcaattc ccgccgcttt ctggacagcc aggttgagat tgggacccgt   1200
cactgtgatg gtgccgtccg gattctccgt tatgaggtcg cagaagaagg tgtttcctgc   1260
atcgcacgcg tcgatttcct gctggggaag gaggaaatcg atcgcgccct tcaccttcac   1320
cacatagcga tcgaccgaaa actgaaaccc cggcacgaag gcgggcgta gcaccgcgcc    1380 gaatgtaagg acgtccgcct tttcagggcg caaatccgcg ttgccggcgg taaagaaccg   1440
cgtctgcaca gcctgtccgc cataaattga attgagcgtc gcctgacggc cggggtcgaa   1500
tagctcgaca aggcttggcc cgcggatatc tcgcgaacgg gtcgcgcgga acctgaggcc   1560
gtcgatcggc tcatattctc cgcccagctt ccaggttgtt actccaccgg actggctgta   1620
atcggcatat cggacggcgc cgtttaagtt cagcgaacgt cccagcgcgc tgtccttcag   1680
aatcgggacg ccgatttcga caaaaccttc cttgatgtca tagcttcccg agaagggaag   1740
tgggttgtag agattgaagc ctccaggccg acctgcctgc gccgccggag ccccctgat    1800 tcccgtgatc gaggtcgtcg cctgcgatat cgcgtcggtt tcctgccggg ccttctcctt   1860
gcgatattcg ataccagcgg cgaccgagac cgggcccgcg ccgaacgaca ggctatcgcc   1920
gaggtcgccg gaaatcgtga gtcccgccac atattgctca agcctcagct gagcgacgcc   1980
atcagcggtg acatagtcga tggccgacgc gctcggcgag cctgtgccga agagattgag   2040
cggcacgcaa tcttggtcga ggccggccag tgttgaacgg cagacgatat tgcccgcggg   2100
atcgcggacc gcatcgacgg cggcgtagag attgcggttg atggtgagat tgttttcacg   2160
aagctcgagg tccgtaaggc caaggaggc cgagccatcg agtttccagc cattgccaat    2220
gtctgcccgg aagccggcag cgccgcggta gacctttgcg aaattctcga tttcgaccaa   2280
gggaaagtcg cttgagaagc gaccgacaac gatcgaagcc tgggcatttc tgtccatgag   2340
cgtcgcgagt ggagccggaa ggaaggcgtt atcacggaag atccggaaat tattcgagcc   2400
accgacatgc gatattacga atgcacccag gttggtgtgg aataagcat aggtgccctc    2460 cgcatacacc tgcacagtgt cggacacatc atatgcggcg cgtaggaacg cgttgtagcg   2520
aagctgatcc ggggcgaagc cgatattcac gcgcggtcca tcgccgccgc tctgaacga    2580 cgagctcgta aaattcccgt agtcgaaggt ccctaggact cctccgggca aaacgcgat    2640 gcctttcaga gggccggacg tgacaagtcc gccgtaggat ccgcgagaac tgcgaatatc   2700
gggcacgacc gtgacgcctg tcgtagcgcc gggcacggga tattggccgg cggcgatgtc   2760
```

```
gaaccagcgg cgacccgttg cttcatcggc ccggattccg tcctgtcgaa aatattcgaa    2820
gctgccgagc aagtgcaacc ggtcgtcggc aaacgaagtg ccgaaggcga tcgaaccgcc    2880
gtaggacggg aggtcgccgc gggttgaaac acccgactgg agctcggccc tgatgccttc    2940
cagatcttcg tcgagcacga agttgatgac gcccgaaacg gcatcggaac cgtaggcggc    3000
cgaggcgccg cccgtcacga catcgacgcg cttgaccaac gcctgcggca gcacgttgat    3060
atcgaccgag cctgtgaaat tggtcgcgac gaaacggttg ccgttcagca ggacgaggtt    3120
ccggtttgac ccgaggccgc gcatgttgag caggttctga ccgctgttcc ccgttccggg    3180
tgtcgtgcca gggttggagg tcttcaagct gtcgttgaac acgggcagct ggttgagtgc    3240
gtcggcaagg ttggtcggag atgcctcctt caactgctcg ctggatacgg ctgtaaccgg    3300
cgtcggcgaa ttgaagccgt tctggaggcg gctgccggtc acgacgattt cgctcgttcc    3360
ccggtccgtg tccgcttcgt ccggctgacc tatcgatgcg ggatcgctat cctgagcact    3420
ggcagagaca ggaaatgcga gggtgccgag cgctactgcg ccgagcaaac tatttgcctt    3480
gccgggcttt tcgattctga acttccgata catctgcagt ccctcccgaa ttgatatggga    3540 ctccgtttga gtccccttgt ttcttgacgc gccgtcgct caccacggtc cggtcggagg    3600
ctaagcgtcg ggcctaagga cccgcaattt gaacatcaaa tgcaatgatc ggaggcttca    3660
ttgcacttcg cgcatagacc ggcgcggtag ctgaaagtgc caataatcag ggattttgct    3720
gaacagttgc ggcatgacgt ccggcatcgg ccacgcggtt ggcggcatcg acgtggcttt    3780
cgcgtcgccg cccctcaagc accggcgagt tgcattaaaa tgggatgagg ctggagagac    3840
gcaaaatctc tgaggaccgc gctgaacgcg cgatccgtcg cctcgagggt ctccgttaca    3900
tcgtcaactg tatgggccgc agagagaaac atattgtgat agggatgaac atagacgccg    3960
cccttcaggc acgccgcggc ccacgcatag ccgatccgaa aatcgggatc gtccgcaaag    4020
aatatttgcg gcatctgcgc cgggcccgtc tgcttcaact caagaccatg gcgctgagac    4080
tgtgcctcca ggcctgcccg cagggcggcg ccgctggcga tcagcgtttc gagataaggc    4140
gtctctcgaa tgatcctgag ggtttcgatc gcggccgcca tcggtaccgc agagaaccag    4200
aaggagccgg tcacaaatat atcccgcgcc gcatcgcgcg ccttgttcga gcccagcagg    4260
gcggagatcg gatagccatt cgcaaagcat tttccccagc aactgagatc gggttcgata    4320
cccaaatgcg tccagctgca atcgcgcgcc acccggaaac ctgcgcgcac atcgtcaacg    4380
accagaagcg caccggtctc gtcacaacat tttcgagcgg tgcgcgcgaa ctcaagctgg    4440
gcgagggcct ggtcctcaaa tacttcgtgt cggaaaggtg tggcaaagac agccgcaata    4500
tcgccatcgt gcgccttgaa cgcgtccgat aagctttggg cgtcgttata ggtataatat    4560
gcgacatgca cgcgatcgga agcgagaatc ccggcagtat gcggagtgtt ccacggggaa    4620
gcgccatgat aggcgccttt ggcgcataat atggttttgc ccccgtatg gcacgcgcg     4680 agaaccatcg ccgttgaggt ggcatcgctg ccattttttgc agaacatcgc ccaatccgca    4740
tgacggacca tgcccacaaa ggcttcggcg aggttgacca tgatctccga aggaccggtc    4800
atggtgtcgc cgagaagtcg ctgcgcatca gccgcggctt cgatttcgga ttgccggtaa    4860
ccgagcaaat ttggcccata cgcgcacata tagtcgatat agggctgctc gtcggcgtcc    4920
caaattcgtg cccccagcgc gcgcctgaag aactggggga attctggcgg cagcaaccgt    4980
gtcgactcgt ggccgtacat cccgcccgga atgacccgtt cggcgcgttc tctgagatct    5040
ttctgccttg ttccgttcgc cataatgcac ctctcgcgat aaataatggg taaaaatcca    5100
cgaaattcaa cgattcgtga tctgaaagag atatatcttg taatatactg tataattata    5160
```

```
cacaatgcgc aatcggacga cgggatagcg gggcagggag gacggggaaa tctatgcgga    5220
acgtcagcga caaggcgccg ccccacgaga cgctcaccgt agtcgtcgcg gcaatgatcg    5280
ttggcacggc cgccttgatg gtgcttggaa tacagcccat ccttctcggc gcccttgtag    5340
aggaggggcg tattcccgcc gaggggttgg gatcggcggc aacggtggaa atactggcga    5400
tcgcggcggg aacatgcatc ggacccgttc ttatgaagac gggatatctg cgggcgaaat    5460
gcgcggcact ctgcttaatg ctcgccgcaa tcaacttcgg attgacgttg ccgggtttcg    5520
atttgcccat cgtggcttgc cgagcggcag cgggagccct ggaaggtctt tcgctcagcg    5580
cggcgatcct gatcatgact cataatcggc ggccggaccg gctgagcgga atatttctgg    5640
gcgcgcagac gataccgcag gtaatatctg cttatttgct cccgacggag attattccgc    5700 gctggggag cgcaggcggc ttcacgatcc tgggcattct cgcggcgatc gccgcgatcg    5760
cggctctgtg cctcgtcgat cgcgttgagc tcgatccgac gaccgttaac gacgacttgc    5820
agtggtcacc cgcggcgatc gtcatttcga tggcggcatt cgttcaattc tcggggtcg    5880 gtgccgcatg gagctatctg gagcgactgg ctgcgcagca cggattttcg ggagaaacga    5940
tcggtatcgc catttccggg agtttgcttt gccaggtagg cggggcttgg ctggccgctt    6000
ggatcggtgg gcgggtcgga tatcgcttcg ccttaatcgc tgggagcctg cttcaggcgg    6060
gcaacgtgat cgcattggcg gtggccgatc agccaagctg gtttatttcc gcttcctgtg    6120
ctttcggcct gttctggttg gcgatgcagc ccttccaaat ccgcttcgcg atcgcgatag    6180
ataacagccg gcagcttgct gtactgctga cgccgatcgc cctcgtcggg ttgagcgcgg    6240
ggcccttgtt gctctctcgc tttgccgggg cgaccgactt gcgctggatc tttgtgggga    6300
gttcgacctt gttgctggcc agcgcgcttc tgtatctttg cgcttctctg tttcaaccgc    6360
gcggaaaggt gatcgctgaa acggtggacg tatgaaaaag acggatcggg gttcgcgatg    6420
acatcgcagg tcaagcttcg tagcgcggca aagcggccgc gcagtcctaa aagcgagcga    6480
ggtcttgctc gttacgagtc cttgcttgat gcgaccgaca ggctgttggt cgatctagac    6540
cccgatcagg tcggtctcta tcagattgca gaggaagcgg gtgcctcacc gtcgtccgtc    6600
tatcatttct ttccgaccaa ggaagtggct catctcgctc tgatgcgccg ctatctggag    6660
gggctccgga atctcgacgc gatggaagtc gacatcggcc agctcgaaag ctggcaggac    6720
ctgatgaagt tggatcagat cagggcgcga gactattata atagccaccc gcccgccctc    6780
aagcttctgt tcggcggata tggcggggtc gaggccagaa agcttgacga gcgatactcc    6840
gaggaaatcg tgagctccat gtatggcaga tacaacggca ttttccatat gccgcaaatg    6900
gagaatgagg ctctcatgtt cacgatctgc ttcgcaattc tcgacgcggt atgggccgtc    6960
tcctttcgcc ggttcggtga aattacgtcg gattttcttc gggaggggca gcggcttgc    7020 attgcctatt gccgacacta tctgcccgag cgaacgccat cagcgtgaat ccgttcaacg    7080
atatgcagga atgtccgttg cgttgagttc ggttctgagt tcggtcggtt aggaggcccc    7140
gcgataaacc aacgctcttc tgtcgaaggg atgtcgcctg gttcgaccag gccctgcgaa    7200
gtcagccgca atcaacgagg cagatgtcaa cgtggccagc aagttcaact gtgagttact    7260
cgatctgcga tcatttgttg cggtgtatga aacgcgaagt tttagccacg ccgcgcggct    7320
tctgaatcaa tcgcagcccg cgctcagccg gagaatccag cgcctcgaga gtctcgtggg    7380
cggtccgttg ttcgagcgga ccagtcggtc gcttgccgaa acggcgctcg gcaaagagtt    7440
gctcccggtc gcccaccgag cgttggaact tgtcgatacg tcgctgtttg cgtcgcccaa    7500
tgtccgggag ttccgctgga cagacatcac gattgcctgt gtacagaccg ccgccttcca    7560
```

```
tgttctcccg cgagctgcgc gcttgtacat ggatcaaaat ccgagggtcc gactccgcat    7620
ccttgacgtg ccggcggtcg aggctgcgga cctggttgcg agcggcgagg cggagttcgg    7680
catcagcatt gagagcctgt tgccatcaag cctgcggttc gatgcgctcc acgaggaccc    7740
gttcggcctg gcatgccacc gaagccatcc gctggcgtcg ctcgagatcc ttgaatggac    7800
gcaattgaaa ggtgaaagcc tgatcgccgt tcaccgtgcg agccggaacc gcacgttgct    7860
cgatgccgaa ctcgcgcgca acaatatcgc gctggaatgg cggtatgagg tcgcgcatct    7920
gacgacggcg ctgggattga tcgatgcgca attgggtgtc gctgttatgc cccgcatggt    7980
tatgccccgc tcgggtcggt cggaggtcgt ctggcgcccc gtcgtcgcgc cggtcgtcca    8040
acgcacgatc ggcatcgttc agcgccgcac cggctcgatg caccctgccg cacagcaatt    8100
gcttgcgcgg ctccgcgcgg cctggtcgtc cgccaatctg ggcgacatcg cgtctcgcga    8160
agatggggca tcgtgacacg cgttctatgc gcctgcagca tcgatgctca cgatcattgc    8220
atttgctgag agacgaacgc gaagatacog ctgggtcaca ggatatcagt ccatcgaggc    8280
gggagagaaa tgtgtgaaag agcaccaatg ccgtggcggc cgggcgtccc ccgctgcgcc    8340
cgccacgtgg cttgcgcgga tcagcgtttc cggggggcc tccgccatcg cctggaccctt    8400 catgcttggc gcaactgcca ttcccgtggc tgcgcaaact gacgatccga agctcgttcg    8460
tcatacccag tcgggcgccg tcgagggcgt cgagggcgac gtcgagactt ttttgggaat    8520
acccttcgcg gctccgccgg tcggcgacct gcgatggcgg ccgccggctc cgccgagggc    8580
gtgggcgggc accagggacg gccgccgctt gcgcccgat tgcatcggga acgagcggct    8640
tagagagggg agccgggctg ccgggacgag cgaagactgc ctctatctga atatctggtc    8700
tcccaaacag gtcggtaagg gggggctccc cgtcatgatc tgggtttacg gcggtgggtt    8760
tagcggcggt tctggcgcgg tgccatatta tgacggctct cgctcgcgc agaagggcgt    8820 ggtggtcgtc acgttcaact atcgcgccgg gattctgggc tttcttgccc atccggcgct    8880
ttcaaaggaa agtccgaatg gcgtgtcggg caactatggt cttctcgaca tgctcgcggc    8940
gttcaaatgg gttcagaaca acataaggga gttcggcgga gaccccgaacc gtgtcacggt    9000 cttttggcgag tccgccggcg cgagcgcgct cggactgctc ctgacctcgc cgctcagtga    9060
gagcgccttc aatcaggcga tactgcaaag tccgggtctg gccaggccgc tcgccacgct    9120
ttctgaaagc gaagcgaatg ggctggagct gggagccgat atttctgctc tacggcgtgc    9180
cgatgcgggc gaattgacga agatcgcgca atcgcgaata cccatgtcgc gccagttcac    9240
caagccgcgg ccgatgggtc cgattctgga cggctatgtt ttgcgcaccc ttgacgtcga    9300
tgccttcgcc aaggggggcct tccgcaagat acccgttctg gtcggcggaa acgccgacga    9360
agggcgcgct tttacggatc gcctgccggt caaaacggtc cttgaatatc gagcctatct    9420
cacagaacaa tttggtgacg aggcggacgc atgggagcgt tgttatcccg cgaactccga    9480
cgccgacgtc cccgccgccg ttgcccgtct ttttggggat agtcagttca acaacgggat    9540
cgagctgctc tcggcagcct tcgcgaaatg gcgaacgccg ctttggagat atcgctttac    9600
gggcattcca ggagccggcc gtcgccccgc cacgcatgga gacgaaattc cctatgtctt    9660
cgcaaatctg gggccgtcgt ccgtatctat gtttgggtcg ctcgaaggcg cgccggggc    9720 gtcggacatc aaacttgcga ccgaaatgtc cgcggcctgg gtgagcttcg cggtgcacgg    9780
ggtccccgat cagggcacga aatcgcactg gccgcgcttc gagcggcgag gggagatcat    9840
gacttttggt tcgcaggttg gctctgggga aggtcttgga gtttcgccga gcaaagcctg    9900
ccaaccctca aaatagcgcc cggcctgtgc gtgcttcagc acgccgtccc gctttgcggg    9960
```

```
cgacgggctg tgccctctgc ctagaaggaa gtaagttgcg ctacgacgtc gcgataattg    10020
gaggtggcaa cgctgcattg acggcagccg tgacggcgcg tgaagcgggg gcctcggttc    10080
ttgtgatcga gcatgcgccg cgcgccatgc gcggcggcaa cagtcgtcac acacgcaata    10140
tgcgtacgat gcacgaacgt cccctgtcgc cgttgaccgg tgaatattcg gcggacgaat    10200
attggaatga tcttgtccgc gtcacggggg ggcgcaccga cgaagaactc gcgcggctcg    10260
ttatccgcaa caccaccgac gctattccct tcatgacgcg ctgcggtgtg cgtttccagc    10320
cctcgctgtc gggcacgctg agtttatcgc gaaccaacgc attcttcctt ggcggcggga    10380
aggcgcttgt aaacgcatat tacgccacgg ccgaacggct aggcgtcgat attctctatg    10440
attctgaggt gaccgagatc aaccttcagc aaggcgtcgt gcagcgtctg caattgcgca    10500
gccggggatt ccctgtcgaa gtggaagcca aggctgccat cgcctcgtcc ggaggattcc    10560
aggcaaatct tgactggctc tcaagcgcat gggggcctgc tgcggcgaac ttcatcgtac    10620
ggggcacgcc atatgcgact ggcacggtgc tcaagaacct gttggagcaa ggcgtcgcct    10680
cggtgggaga tccaacccaa tgccatgctg tcgcgatcga tgggcgagcg cccaaatacg    10740
acggcggcat cgtcacacga ctggactgcg ttcccttctc gatcgtcgtc aacaaggacg    10800
ccttgcgctt ctacgatgaa ggcgaagatg tgtggccgaa gcgttacgcc atatggggtc    10860
gcttggtggc acagcagcct gatcagatcg ctttcagcat aatcgatcgg caggccgaag    10920
acctcttcat gccgtcagtg ttccccccg tgcaagcgga cacgatcgcg ggtctggccg    10980
agaaactcgg tctgaatccc gtaaccctgg aacgcacggt ggccgaattc aacgccgcat    11040
gcgtgcccgg cgaattcggc ggccaagatc tcgacgacct ccacaccgag ggaatcgaac    11100
caaagaaatc caactgggcc cgaccgatta ttgtgccccc gttcagcgcc tatcctctcc    11160
ggcccgggat caccttcacc tatctcggcg tcaaggtaga cagccgtgcg cgggtcatca    11220
tggagacagg tgagccgaca aaaaacctgt ttgcttcggg ggaaataatg gcgggcagca    11280
ttctcggcca aggttatctc gctggatttg gaatggcgat tggtaccgta ttcggccgca    11340 tcgcggggttg ggaggccgca cgtcatgcag gattttgatc tcgtaaaaat gctgtctgac    11400
ttgccgtcgg cgccggagct ggaagccagg cgcgttatgg aggtgtgcaa cgcgtgccgc    11460
tattgcgaag ggttctgcgc ggtatttcct gcaatgacct tgcagcgtca tttcgccagc    11520
ggcgatctca gccacctcgc caatctctgc cactcgtgcc aaggttgcta ttacgcctgc    11580
caatacgccc ctccgcatga gttcggaata aacgttccaa aggcgctgtc ggagttgcgg    11640
ctcgagagct acgagcagca tgcttggccc cggccggtcg ccgctctcta tcgcaagaat    11700
gcgctcatca tttccatctt gtcggcggca tgcataaccg gcgtccttct gcttgccgcc    11760
atcttcaacg gggatgcact tttgcgcaaa cacgcatcgg tgcccggcgg cgggttttac    11820
aacgttattc cttatcaggc gatgattgcc gtcgcggcga ccacatttct ttattccgcg    11880
ctggcgctgg cgatcagtct cgttcgcttt tcgcggacga tcggtctggg aattaaggtt    11940
ctttatcagc acgtgccggt tcttcgggcg ctacgcgatg cggcgactct gcgatatctc    12000
ggcggcagcg acggcgaggg gtgtaacgac gcggacgaga cattttcgac gacccggcga    12060
aaatttcatc acgcccttgc ctatggcttc ggactttgtt tcgcggccac agccacgggc    12120
acgatctacg atcatatgtt cggctggccg gcgcccatg cgcttttcag cttgccggtc    12180
gtcctaggga ccgttggggg gatcggaatg gtcgtgggcg cgatcggcct actctggctc    12240
aagctggccg gcgaagacgc tcctcgatca ccggcactgc ttgggccgga tgttgccctg    12300
ttggtgcttc tgcttgccat agcggcaacg ggcctcctcc ttttagcggt ccgcagcacc    12360
```

```
gaagtcatgg gcgtcgcgct cgccgtccat ctcggcgtcg tcttggcctt cttttttggtg   12420 atgccataca gcaaatttgt ccacggtatc ttcaggctca cggctctcgt gcgccatcat   12480
gctgaccgcg aggcaagtaa tggcttcgcc tccagccctc ccacgaaaaa gggttaaaca   12540
atggaacata tgaagtccgt tcgcgatcgc agtagcgtca tgcagatcgt gagagtggcg   12600
agtggcaact gtctcgagca atatgatttc ttcgtttacg gcttctatgc ggcatatatt   12660
gcgagaagct ttttccgac cggcgataac gcgacatcgc tcatgctttc attggccact   12720
tttggcgctg gtttcctcat gaggcccttg ggggcgattt ttctcgggtc ctacatcgat   12780
cgcgtcgggc gtcggaaagg cctgatcgtg acactcgcga tcatggccgt cggaaccctc   12840
accattgcga tgactccaag ctatgaggca attggattac tcgcaccggt tatcgtgctc   12900
gtcgggcgac ttttgcaggg ttttttccgct ggagcagagt cgggtggcgt ctcagtgtac   12960
ttggcggaaa ttgcgtcgcc caaatcgaga ggcttcttca cctcgtggca gtctgccagc   13020
cagcaggtgg ccgtcatgat cgccgccgcg atcggtcttg cgctgcaatc aacgctttca   13080
ccggagcaaa tgaacgactg gggatggcgg gtgcccttgt tgatcggatg cttgattatc   13140
cccgtgatac tctggctgcg ccggtctctc ccggaaacga agcctatct ccacatggag   13200 cacaaggcgc attcgatcgg cgaatccctc cgcgaattgc aacagagctg ggggctgatc   13260
ttgacgggca tggcgatgtc gatcctcacg acgaccacct tttacatgat taccgcctat   13320
acgccgacat ttggcgagaa agcactcgga ctgagcccgc aagatgtcct gctggttacc   13380
atcatggtcg gcgtgtcgaa cttcctgtgg cttccgatcg ggggtgctct ctcggatcgt   13440
atcggtagaa ccccgatcct actggtcgtg ccggtcaccg ttctcgccat cgcctttccc   13500
ctgatgagct ggctcgtcgc ggcaccgaca ttcggagcgc ttgcagctgt tctgctgact   13560
ttctccgcat gctttggact ctataatggg gcgctcatcg cgagactcac cgagattatg   13620
cctcccgcca ttagaaccct tggcttctcg ctggcgttca gtctcgcgac ctcgctgttc   13680
ggcggcttca ccccattggt aagtacggcg ctaatccacg cgacgggcag caattccgcg   13740
cctgcaatct ggctctgttt tgcggctttc atcagcttcg tcggtgtggc cgcatcgacc   13800
cggctgagcc ggccaatcgc cgaaggcgcc agataggaca atcagagaat gcccgtgcgg   13860
caatgaagcg agattcgggc ggtaggtgcg ctggcggcac ttcgcgaaga gccgttgcgg   13920
acggctgaaa cgatgatggt atgaatgggc taagacatga gagcagtagt ttaccgaaat   13980
ggcgaacttg tcctgggggc ctatgctgat ccgatacccg ccgccgggca ggtgctcgtc   14040
aagaccagag catgcggcat ctgcggatct gaccttcatt tttgcgatca tgcgcaggcg   14100
tttacgaacc ttgcatcgcg ggcgggtatc gcctctatgg aagttgattt gtgtcgagac   14160
atcgttctgg ggcatgaatt ctgtggcgag attatggagt tcgggccctc tgcggatcgt   14220
cgcttcaaac ccggacagct tgtgtgctcg ctgccgctgg cgatcggtcc gaccggagcg   14280
cggacgattg gctactcgga tgagtatccc ggcgggctcg gcgaatatat ggtcctcacg   14340
gaagcgctct tgctgcctgt tccgaacggc cttccggcga cctgcgcggc gttgacggag   14400
ccgatggcgt gggatggca tgccgtcgag atcgcgcagg ttcaaccaca tcacatccct   14460
gtggtgatcg ggtgcggacc ggtcgggttg gcagtcgtcg ctgccctgaa acataagcaa   14520
gttgctccga ttattgcgtc ggatccatcg cccgatcggc gtgctcttgc tctgcggatg   14580
ggcgccgacg ccgttgtcga tccgcgcgaa gaatcaccct ttcgccaggc cgagaagatc   14640
gcacgcccgg tcggacaagg tgggggcctg tccagctcat tgctgtcaaa gtctcaaatg   14700
atattcgaat gcgtagggt gccgggcatg cttcggcatg cgatggacgg cgcgtccgac   14760
```

```
gggtccgaga tcatggtcgt tggcgcatgc atgcagccgg acgcgatcga gcccatgatc    14820
gggatgttta aagcgctcac gatcaaattc tcgcgaactt acacgggtga ggaattcgcc    14880
gcggtgcttc acatgatagg tgagggcgca ctcgacgtat ctccgctcgt taccgatgtg    14940
attggcctgt ccgatgtccc gtccgcgttt gaggctctac ggagtccagg cgcccaagca    15000
aaagtgattg tggaccccttg gcgctgagcc tgaggatgcc aagggtgcga cgttgggcat    15060
cgtcaaagaa ggcgacgttg acccggtatg tgaacatccc catattcttc cgcagctgaa    15120
gcagttggta aacatgccaa aatatgaact gtagtattgc gtcggggttc tcattgtggg    15180
gtttgccatt gtcatcgctc gcacccggcg acaaagatta gatgtacttc cgataatccg    15240
tgctctcgac ctggccttcc ttcatatatt tcaggacctc tccgaccatg cgtgcggcgc    15300
ggatcgggat cggcaggcgt tggttcatct gggtcgagtt ccagttgatc ttcgtaagag    15360
agaacacctc ctcggctaac tgcgccgcgg tactatcgca ggatcgtctc gagcgtycgc    15420
```

<210> SEQ ID NO 2
<211> LENGTH: 1182
<212> TYPE: DNA
<213> ORGANISM: Sphingopyxis sp.
<220> FEATURE:
<223> OTHER INFORMATION: Seq ID 2 (fumA)
<300> PUBLICATION INFORMATION:
<308> DATABASE ACCESSION NUMBER: FJ426269
<309> DATABASE ENTRY DATE: 2009-06-11
<313> RELEVANT RESIDUES IN SEQ ID NO: (1)..(1182)

<400> SEQUENCE: 2

```
atgcggaacg tcagcgacaa ggcgccgccc cacgagacgc tcaccgtagt cgtcgcggca      60
atgatcgttg gcacggccgc cttgatggtg cttggaatac agcccatcct tctcggcgcc     120
cttgtagagg agggggcgtat tcccgccgag gggttgggat cggcggcaac ggtggaaata     180
ctggcgatcg cggcgggaac atgcatcgga cccgttctta tgaagacggg atatctgcgg     240
gcgaaatgcg cggcactctg cttaatgctc gccgcaatca acttcggatt gacgttgccg     300
ggtttcgatt tgcccatcgt ggcttgccga gcggcagcgg gagccctgga aggtctttcg     360
ctcagcgcgg cgatcctgat catgactcat aatcggcggc cggaccggct gagcggaata     420
tttctgggcg cgcagacgat accgcaggta atatctgctt atttgctccc gacggagatt     480
attccgcgct gggggagcgc aggcggcttc acgatcctgg gcattctcgc ggcgatcgcc     540
gcgatcgcgg ctctgtgcct cgtcgatcgc gttgagctcg atccgacgac cgttaacgac     600
gacttgcagt ggtcacccgc ggcgatcgtc atttcgatgg cggcattcgt tcaattctcg     660
ggggtcggtg ccgcatggag ctatctggag cgactggctg cgcagcacgg attttcggga     720
gaaacgatcg gtatcgccat ttccgggagt ttgctttgcc aggtaggcgg ggcttggctg     780
gccgcttgga tcggtgggcg ggtcggatat cgcttcgcct taatcgctgg gagcctgctt     840
caggcgggca acgtgatcgc attggcgtg gccgatcagc caagctggtt tatttccgct     900
tcctgtgctt tcggcctgtt ctggttggcg atgcagcccct tccaaatccg cttcgcgatc     960
gcgatagata acagccggca gcttgctgta ctgctgacgc cgatcgccct cgtcgggttc    1020
agcgcggggc ccttgttgct ctctcgcttt gccggggcga ccgacttgcg ctggatcttt    1080
gtggggagtt cgaccttgtt gctggccagc gcgcttctgt atctttgcgc ttctctgttt    1140
caaccgcgcg gaaaggtgat cgctgaaacg gtggacgtat ga                       1182
```

<210> SEQ ID NO 3
<211> LENGTH: 393
<212> TYPE: PRT

<213> ORGANISM: Sphingopyxis sp.
<220> FEATURE:
<223> OTHER INFORMATION: Seq ID 3 (FumA)
<300> PUBLICATION INFORMATION:
<308> DATABASE ACCESSION NUMBER: FJ426269
<309> DATABASE ENTRY DATE: 2009-06-11
<313> RELEVANT RESIDUES IN SEQ ID NO: (1)..(393)

<400> SEQUENCE: 3

| | | | | | | | | | | | | | | | |
|---|---|---|---|---|---|---|---|---|---|---|---|---|---|---|---|
| Met | Arg | Asn | Val | Ser | Asp | Lys | Ala | Pro | Pro | His | Glu | Thr | Leu | Thr | Val |
| 1 | | | | 5 | | | | | 10 | | | | | 15 | |
| Val | Val | Ala | Ala | Met | Ile | Val | Gly | Thr | Ala | Ala | Leu | Met | Val | Leu | Gly |
| | | | 20 | | | | | 25 | | | | | 30 | | |
| Ile | Gln | Pro | Ile | Leu | Leu | Gly | Ala | Leu | Val | Glu | Glu | Gly | Arg | Ile | Pro |
| | | | 35 | | | | | 40 | | | | | 45 | | |
| Ala | Glu | Gly | Leu | Gly | Ser | Ala | Ala | Thr | Val | Glu | Ile | Leu | Ala | Ile | Ala |
| | | | 50 | | | | | 55 | | | | | 60 | | |
| Ala | Gly | Thr | Cys | Ile | Gly | Pro | Val | Leu | Met | Lys | Thr | Gly | Tyr | Leu | Arg |
| 65 | | | | | 70 | | | | | 75 | | | | | 80 |
| Ala | Lys | Cys | Ala | Ala | Leu | Cys | Leu | Met | Leu | Ala | Ala | Ile | Asn | Phe | Gly |
| | | | | 85 | | | | | 90 | | | | | 95 | |
| Leu | Thr | Leu | Pro | Gly | Phe | Asp | Leu | Pro | Ile | Val | Ala | Cys | Arg | Ala | Ala |
| | | | | 100 | | | | | 105 | | | | | 110 | |
| Ala | Gly | Ala | Leu | Glu | Gly | Leu | Ser | Leu | Ser | Ala | Ala | Ile | Leu | Ile | Met |
| | | | | 115 | | | | | 120 | | | | | 125 | |
| Thr | His | Asn | Arg | Arg | Pro | Asp | Arg | Leu | Ser | Gly | Ile | Phe | Leu | Gly | Ala |
| | 130 | | | | | 135 | | | | | 140 | | | | |
| Gln | Thr | Ile | Pro | Gln | Val | Ile | Ser | Ala | Tyr | Leu | Leu | Pro | Thr | Glu | Ile |
| 145 | | | | | 150 | | | | | 155 | | | | | 160 |
| Ile | Pro | Arg | Trp | Gly | Ser | Ala | Gly | Gly | Phe | Thr | Ile | Leu | Gly | Ile | Leu |
| | | | | 165 | | | | | 170 | | | | | 175 | |
| Ala | Ala | Ile | Ala | Ala | Ile | Ala | Ala | Leu | Cys | Leu | Val | Asp | Arg | Val | Glu |
| | | | | 180 | | | | | 185 | | | | | 190 | |
| Leu | Asp | Pro | Thr | Thr | Val | Asn | Asp | Asp | Leu | Gln | Trp | Ser | Pro | Ala | Ala |
| | | | | 195 | | | | | 200 | | | | | 205 | |
| Ile | Val | Ile | Ser | Met | Ala | Ala | Phe | Val | Gln | Phe | Ser | Gly | Val | Gly | Ala |
| | 210 | | | | | 215 | | | | | 220 | | | | |
| Ala | Trp | Ser | Tyr | Leu | Glu | Arg | Leu | Ala | Ala | Gln | His | Gly | Phe | Ser | Gly |
| 225 | | | | | 230 | | | | | 235 | | | | | 240 |
| Glu | Thr | Ile | Gly | Ile | Ala | Ile | Ser | Gly | Ser | Leu | Leu | Cys | Gln | Val | Gly |
| | | | | 245 | | | | | 250 | | | | | 255 | |
| Gly | Ala | Trp | Leu | Ala | Ala | Trp | Ile | Gly | Gly | Arg | Val | Gly | Tyr | Arg | Phe |
| | | | | 260 | | | | | 265 | | | | | 270 | |
| Ala | Leu | Ile | Ala | Gly | Ser | Leu | Leu | Gln | Ala | Gly | Asn | Val | Ile | Ala | Leu |
| | | | | 275 | | | | | 280 | | | | | 285 | |
| Ala | Val | Ala | Asp | Gln | Pro | Ser | Trp | Phe | Ile | Ser | Ala | Ser | Cys | Ala | Phe |
| | 290 | | | | | 295 | | | | | 300 | | | | |
| Gly | Leu | Phe | Trp | Leu | Ala | Met | Gln | Pro | Phe | Gln | Ile | Arg | Phe | Ala | Ile |
| 305 | | | | | 310 | | | | | 315 | | | | | 320 |
| Ala | Ile | Asp | Asn | Ser | Arg | Gln | Leu | Ala | Val | Leu | Leu | Thr | Pro | Ile | Ala |
| | | | | 325 | | | | | 330 | | | | | 335 | |
| Leu | Val | Gly | Leu | Ser | Ala | Gly | Pro | Leu | Leu | Ser | Arg | Phe | Ala | Gly | |
| | | | | 340 | | | | | 345 | | | | | 350 | |
| Ala | Thr | Asp | Leu | Arg | Trp | Ile | Phe | Val | Gly | Ser | Ser | Thr | Leu | Leu | Leu |
| | | | | 355 | | | | | 360 | | | | | 365 | |
| Ala | Ser | Ala | Leu | Leu | Tyr | Leu | Cys | Ala | Ser | Leu | Phe | Gln | Pro | Arg | Gly |

```
                    370                375                380
Lys Val Ile Ala Glu Thr Val Asp Val
385                 390

<210> SEQ ID NO 4
<211> LENGTH: 651
<212> TYPE: DNA
<213> ORGANISM: Sphingopyxis sp.
<220> FEATURE:
<223> OTHER INFORMATION: Seq ID 4 (fumB)
<300> PUBLICATION INFORMATION:
<308> DATABASE ACCESSION NUMBER: FJ426269
<309> DATABASE ENTRY DATE: 2009-06-11
<313> RELEVANT RESIDUES IN SEQ ID NO: (1)..(651)

<400> SEQUENCE: 4
atgacatcgc aggtcaagct tcgtagcgcg gcaaagcggc cgcgcagtcc taaaagcgag    60
cgaggtcttg ctcgttacga gtccttgctt gatgcgaccg acaggctgtt ggtcgatcta   120
gaccccgatc aggtcggtct ctatcagatt gcagaggaag cgggtgcctc accgtcgtcc   180
gtctatcatt tctttccgac caaggaagtg gctcatctcg ctctgatgcg ccgctatctg   240
gaggggctcc ggaatctcga cgcgatggaa gtcgacatcg ccagctcga aagctggcag   300 gacctgatga agttggatca gatcagggcg cgagactatt ataatagcca cccgcccgcc   360
ctcaagcttc tgttcggcgg atatggcggg gtcgaggcca aaagcttga cgagcgatac   420 tccgaggaaa tcgtgagctc catgtatggc agatacaacg gcattttcca tatgccgcaa   480
atggagaatg aggctctcat gttcacgatc tgcttcgcaa ttctcgacgc ggtatgggcc   540 gtctccttc gccggttcgg tgaaattacg tcggattttc ttcgggaggg gcaagcggct   600
tgcattgcct attgccgaca ctatctgccc gagcgaacgc catcagcgtg a            651

<210> SEQ ID NO 5
<211> LENGTH: 216
<212> TYPE: PRT
<213> ORGANISM: Sphingopyxis sp.
<220> FEATURE:
<223> OTHER INFORMATION: Seq ID 5 (FumB)
<300> PUBLICATION INFORMATION:
<308> DATABASE ACCESSION NUMBER: FJ426269
<309> DATABASE ENTRY DATE: 2009-06-11
<313> RELEVANT RESIDUES IN SEQ ID NO: (1)..(216)

<400> SEQUENCE: 5

Met Thr Ser Gln Val Lys Leu Arg Ser Ala Ala Lys Arg Pro Arg Ser
1               5                   10                  15

Pro Lys Ser Glu Arg Gly Leu Ala Arg Tyr Glu Ser Leu Leu Asp Ala
            20                  25                  30

Thr Asp Arg Leu Leu Val Asp Leu Asp Pro Asp Gln Val Gly Leu Tyr
        35                  40                  45

Gln Ile Ala Glu Glu Ala Gly Ala Ser Pro Ser Ser Val Tyr His Phe
    50                  55                  60

Phe Pro Thr Lys Glu Val Ala His Leu Ala Leu Met Arg Arg Tyr Leu
65                  70                  75                  80

Glu Gly Leu Arg Asn Leu Asp Ala Met Glu Val Asp Ile Gly Gln Leu
                85                  90                  95

Glu Ser Trp Gln Asp Leu Met Lys Leu Asp Gln Ile Arg Ala Arg Asp
            100                 105                 110

Tyr Tyr Asn Ser His Pro Pro Ala Leu Lys Leu Leu Phe Gly Gly Tyr
        115                 120                 125

Gly Gly Val Glu Ala Arg Lys Leu Asp Glu Arg Tyr Ser Glu Glu Ile
```

```
                130                 135                 140
Val Ser Ser Met Tyr Gly Arg Tyr Asn Gly Ile Phe His Met Pro Gln
145                 150                 155                 160

Met Glu Asn Glu Ala Leu Met Phe Thr Ile Cys Phe Ala Ile Leu Asp
                165                 170                 175

Ala Val Trp Ala Val Ser Phe Arg Arg Phe Gly Glu Ile Thr Ser Asp
            180                 185                 190

Phe Leu Arg Glu Gly Gln Ala Ala Cys Ile Ala Tyr Cys Arg His Tyr
        195                 200                 205

Leu Pro Glu Arg Thr Pro Ser Ala
    210                 215
```

<210> SEQ ID NO 6
<211> LENGTH: 945
<212> TYPE: DNA
<213> ORGANISM: Sphingopyxis sp.
<220> FEATURE:
<223> OTHER INFORMATION: Seq ID 6 (fumC)
<300> PUBLICATION INFORMATION:
<308> DATABASE ACCESSION NUMBER: FJ426269
<309> DATABASE ENTRY DATE: 2009-06-11
<313> RELEVANT RESIDUES IN SEQ ID NO: (1)..(945)

<400> SEQUENCE: 6

```
gtggccagca agttcaactg tgagttactc gatctgcgat catttgttgc ggtgtatgaa      60
acgcgaagtt ttagccacgc cgcgcggctt ctgaatcaat cgcagcccgc gctcagccgg     120
agaatccagc gcctcgagag tctcgtgggc ggtccgttgt tcgagcggac cagtcggtcg     180
cttgccgaaa cggcgctcgg caaagagttg ctcccggtcg cccaccgagc gttggaactt     240
gtcgatacgt cgctgtttgc gtcgcccaat gtccgggagt tccgctggac agacatcacg     300
attgcctgtg tacagaccgc cgccttccat gttctcccgc gagctgcgcg cttgtacatg     360
gatcaaaatc cgagggtccg actccgcatc cttgacgtgc cggcggtcga ggctgcggac     420
ctggttgcga gcggcgaggc ggagttcggc atcagcattg agagcctgtt gccatcaagc     480
ctgcggttcg atgcgctcca cgaggacccg ttcggcctgg catgccaccg aagccatccg     540
ctggcgtcgc tcgagatcct tgaatggacg caattgaaag gtgaaagcct gatcgccgtt     600
caccgtgcga gccggaaccg cacgttgctc gatgccgaac tcgcgcgcaa caatatcgcg     660
ctggaatggc ggtatgaggt cgcgcatctg acgacggcgc tgggattgat cgatgcgcaa     720
ttgggtgtcg ctgttatgcc ccgcatggtt atgccccgct cgggtcggtc ggaggtcgtc     780
tggcgccccg tcgtcgcgcc ggtcgtccaa cgcacgatcg gcatcgttca gcgccgcacc     840
ggctcgatgc accctgccgc acagcaattg cttgcgcggc tccgcgcggc ctggtcgtcc     900
gccaatctgg gcgacatcgc gtctcgcgaa gatggggcat cgtga                    945
```

<210> SEQ ID NO 7
<211> LENGTH: 314
<212> TYPE: PRT
<213> ORGANISM: Sphingopyxis sp.
<220> FEATURE:
<223> OTHER INFORMATION: Seq ID 7 (FumC)
<300> PUBLICATION INFORMATION:
<308> DATABASE ACCESSION NUMBER: FJ426269
<309> DATABASE ENTRY DATE: 2009-06-11
<313> RELEVANT RESIDUES IN SEQ ID NO: (1)..(314)

<400> SEQUENCE: 7

```
Val Ala Ser Lys Phe Asn Cys Glu Leu Leu Asp Leu Arg Ser Phe Val
1               5                   10                  15
```

```
Ala Val Tyr Glu Thr Arg Ser Phe Ser His Ala Ala Arg Leu Leu Asn
             20                  25                  30

Gln Ser Gln Pro Ala Leu Ser Arg Ile Gln Arg Leu Glu Ser Leu
         35                  40                  45

Val Gly Gly Pro Leu Phe Glu Arg Thr Ser Arg Ser Leu Ala Glu Thr
 50                  55                  60

Ala Leu Gly Lys Glu Leu Leu Pro Val Ala His Arg Ala Leu Glu Leu
 65                  70                  75                  80

Val Asp Thr Ser Leu Phe Ala Ser Pro Asn Val Arg Glu Phe Arg Trp
                 85                  90                  95

Thr Asp Ile Thr Ile Ala Cys Val Gln Thr Ala Ala Phe His Val Leu
                100                 105                 110

Pro Arg Ala Ala Arg Leu Tyr Met Asp Gln Asn Pro Arg Val Arg Leu
             115                 120                 125

Arg Ile Leu Asp Val Pro Ala Val Glu Ala Ala Asp Leu Val Ala Ser
130                 135                 140

Gly Glu Ala Glu Phe Gly Ile Ser Ile Glu Ser Leu Leu Pro Ser Ser
145                 150                 155                 160

Leu Arg Phe Asp Ala Leu His Glu Asp Pro Phe Gly Leu Ala Cys His
                165                 170                 175

Arg Ser His Pro Leu Ala Ser Leu Glu Ile Leu Glu Trp Thr Gln Leu
            180                 185                 190

Lys Gly Glu Ser Leu Ile Ala Val His Arg Ala Ser Arg Asn Arg Thr
        195                 200                 205

Leu Leu Asp Ala Glu Leu Ala Arg Asn Asn Ile Ala Leu Glu Trp Arg
210                 215                 220

Tyr Glu Val Ala His Leu Thr Thr Ala Leu Gly Leu Ile Asp Ala Gln
225                 230                 235                 240

Leu Gly Val Ala Val Met Pro Arg Met Val Met Pro Arg Ser Gly Arg
                245                 250                 255

Ser Glu Val Val Trp Arg Pro Val Val Ala Pro Val Val Gln Arg Thr
            260                 265                 270

Ile Gly Ile Val Gln Arg Arg Thr Gly Ser Met His Pro Ala Ala Gln
        275                 280                 285

Gln Leu Leu Ala Arg Leu Arg Ala Ala Trp Ser Ser Ala Asn Leu Gly
290                 295                 300

Asp Ile Ala Ser Arg Glu Asp Gly Ala Ser
305                 310

<210> SEQ ID NO 8
<211> LENGTH: 1623
<212> TYPE: DNA
<213> ORGANISM: Sphingopyxis sp.
<220> FEATURE:
<223> OTHER INFORMATION: Seq ID 8 (fumD)
<300> PUBLICATION INFORMATION:
<308> DATABASE ACCESSION NUMBER: FJ426269
<309> DATABASE ENTRY DATE: 2009-06-11
<313> RELEVANT RESIDUES IN SEQ ID NO: (1)..(1623)

<400> SEQUENCE: 8
gtgaaagagc accatgccg tggcggccgg gcgtccccg ctgcgcccgc cacgtggctt      60
gcgcggatca gcgtttccg gggggcctcc gccatcgcct ggaccttcat gcttggcgca    120
actgccattc ccgtggctgc gcaaactgac gatccgaagc tcgttcgtca tacccagtcg   180
ggcgccgtcg agggcgtcga gggcgacgtc gagactttt tgggaatacc cttcgcggct   240
ccgccggtcg gcgacctgcg atggcggccg ccggctccgc cgagggcgtg ggcgggcacc   300
```

-continued

```
agggacggcc gccgctttgc gcccgattgc atcgggaacg agcggcttag agaggggagc      360
cgggctgccg ggacgagcga agactgcctc tatctgaata tctggtctcc caaacaggtc      420
ggtaaggggg ggctccccgt catgatctgg gtttacggcg gtgggtttag cggcggttct      480
ggcgcggtgc catattatga cggctctgcg ctcgcgcaga agggcgtggt ggtcgtcacg      540
ttcaactatc gcgccgggat tctgggcttt cttgcccatc cggcgctttc aaaggaaagt      600
ccgaatggcg tgtcgggcaa ctatggtctt ctcgacatgc tcgcggcgtt caaatgggtt      660
cagaacaaca taagggagtt cggcggagac ccgaaccgtg tcacggtctt tggcgagtcc      720
gccggcgcga gcgcgctcgg actgctcctg acctcgccgc tcagtgagag cgccttcaat      780
caggcgatac tgcaaagtcc gggtctggcc aggccgctcg ccacgctttc tgaaagcgaa      840
gcgaatgggc tggagctggg agccgatatt tctgctctac ggcgtgccga tgcgggcgaa      900
ttgacgaaga tcgcgcaatc gcgaataccc atgtcgcgcc agttcaccaa gccgcggccg      960
atgggtccga ttctggacgg ctatgttttg cgcacccttg acgtcgatgc cttcgccaag     1020
ggggccttcc gcaagatacc cgttctggtc ggcggaaacg ccgacgaagg cgcgcttttt     1080
acggatcgcc tgccggtcaa aacggtccct gaatatcgag cctatctcac agaacaattt     1140
ggtgacgagg cggacgcatg ggagcgttgt tatcccgcga actccgacgc cgacgtcccc     1200
gccgccgttg cccgtctttt tggggatagt cagttcaaca acgggatcga gctgctctcg     1260
gcagccttcg cgaaatggcg aacgccgctt tggagatatc gctttacggg cattccagga     1320 gccgccgtc gccccgccac gcatggagac gaaattccct atgtcttcgc aaatctgggg     1380
ccgtcgtccg tatctatgtt tgggtcgctc gaaggcggcg ccggggcgtc ggacatcaaa     1440
cttgcgaccg aaatgtccgc ggcctggtg agcttcgcgg tgcacggggt ccccgatcag     1500
ggcacgaaat cgcactggcc gcgcttcgag cggcgagggg agatcatgac tttttggttcg     1560 caggttggct ctggggaagg tcttggagtt tcgccgagca aagcctgcca accctcaaaa     1620
tag                                                                    1623
```

<210> SEQ ID NO 9
<211> LENGTH: 540
<212> TYPE: PRT
<213> ORGANISM: Sphingopyxis sp.
<220> FEATURE:
<223> OTHER INFORMATION: Seq ID 9 (FumD)
<300> PUBLICATION INFORMATION:
<308> DATABASE ACCESSION NUMBER: FJ426269
<309> DATABASE ENTRY DATE: 2009-06-11
<313> RELEVANT RESIDUES IN SEQ ID NO: (1)..(540)

<400> SEQUENCE: 9

Val Lys Glu His Gln Cys Arg Gly Gly Arg Ala Ser Pro Ala Ala Pro
1               5                   10                  15

Ala Thr Trp Leu Ala Arg Ile Ser Val Ser Arg Gly Ala Ser Ala Ile
            20                  25                  30

Ala Trp Thr Phe Met Leu Gly Ala Thr Ala Ile Pro Val Ala Ala Gln
        35                  40                  45

Thr Asp Asp Pro Lys Leu Val Arg His Thr Gln Ser Gly Ala Val Glu
    50                  55                  60

Gly Val Glu Gly Asp Val Glu Thr Phe Leu Gly Ile Pro Phe Ala Ala
65                  70                  75                  80

Pro Pro Val Gly Asp Leu Arg Trp Arg Pro Ala Pro Pro Arg Ala
                85                  90                  95

Trp Ala Gly Thr Arg Asp Gly Arg Arg Phe Ala Pro Asp Cys Ile Gly

-continued

```
               100                 105                 110
Asn Glu Arg Leu Arg Glu Gly Ser Arg Ala Ala Gly Thr Ser Glu Asp
        115                 120                 125
Cys Leu Tyr Leu Asn Ile Trp Ser Pro Lys Gln Val Gly Lys Gly Gly
        130                 135                 140
Leu Pro Val Met Ile Trp Val Tyr Gly Gly Phe Ser Gly Gly Ser
145                 150                 155                 160
Gly Ala Val Pro Tyr Tyr Asp Gly Ser Ala Leu Ala Gln Lys Gly Val
                165                 170                 175
Val Val Val Thr Phe Asn Tyr Arg Ala Gly Ile Leu Gly Phe Leu Ala
                180                 185                 190
His Pro Ala Leu Ser Lys Glu Ser Pro Asn Gly Val Ser Gly Asn Tyr
                195                 200                 205
Gly Leu Leu Asp Met Leu Ala Ala Phe Lys Trp Val Gln Asn Asn Ile
                210                 215                 220
Arg Glu Phe Gly Gly Asp Pro Asn Arg Val Thr Val Phe Gly Glu Ser
225                 230                 235                 240
Ala Gly Ala Ser Ala Leu Gly Leu Leu Leu Thr Ser Pro Leu Ser Glu
                245                 250                 255
Ser Ala Phe Asn Gln Ala Ile Leu Gln Ser Pro Gly Leu Ala Arg Pro
                260                 265                 270
Leu Ala Thr Leu Ser Glu Ser Glu Ala Asn Gly Leu Glu Leu Gly Ala
                275                 280                 285
Asp Ile Ser Ala Leu Arg Arg Ala Asp Ala Gly Glu Leu Thr Lys Ile
                290                 295                 300
Ala Gln Ser Arg Ile Pro Met Ser Arg Gln Phe Thr Lys Pro Arg Pro
305                 310                 315                 320
Met Gly Pro Ile Leu Asp Gly Tyr Val Leu Arg Thr Leu Asp Val Asp
                325                 330                 335
Ala Phe Ala Lys Gly Ala Phe Arg Lys Ile Pro Val Leu Val Gly Gly
                340                 345                 350
Asn Ala Asp Glu Gly Arg Ala Phe Thr Asp Arg Leu Pro Val Lys Thr
                355                 360                 365
Val Leu Glu Tyr Arg Ala Tyr Leu Thr Glu Gln Phe Gly Asp Glu Ala
                370                 375                 380
Asp Ala Trp Glu Arg Cys Tyr Pro Ala Asn Ser Asp Ala Asp Val Pro
385                 390                 395                 400
Ala Ala Val Ala Arg Leu Phe Gly Asp Ser Gln Phe Asn Asn Gly Ile
                405                 410                 415
Glu Leu Leu Ser Ala Ala Phe Ala Lys Trp Arg Thr Pro Leu Trp Arg
                420                 425                 430
Tyr Arg Phe Thr Gly Ile Pro Gly Ala Gly Arg Arg Pro Ala Thr His
                435                 440                 445
Gly Asp Glu Ile Pro Tyr Val Phe Ala Asn Leu Gly Pro Ser Ser Val
                450                 455                 460
Ser Met Phe Gly Ser Leu Glu Gly Gly Ala Gly Ala Ser Asp Ile Lys
465                 470                 475                 480
Leu Ala Thr Glu Met Ser Ala Ala Trp Val Ser Phe Ala Val His Gly
                485                 490                 495
Val Pro Asp Gln Gly Thr Lys Ser His Trp Pro Arg Phe Glu Arg Arg
                500                 505                 510
Gly Glu Ile Met Thr Phe Gly Ser Gln Val Gly Ser Gly Glu Gly Leu
                515                 520                 525
```

Gly Val Ser Pro Ser Lys Ala Cys Gln Pro Ser Lys
    530                 535                 540

<210> SEQ ID NO 10
<211> LENGTH: 1503
<212> TYPE: DNA
<213> ORGANISM: Sphingopyxis sp.
<220> FEATURE:
<223> OTHER INFORMATION: Seq ID 10 (fumE)
<300> PUBLICATION INFORMATION:
<308> DATABASE ACCESSION NUMBER: FJ426269
<309> DATABASE ENTRY DATE: 2009-06-11
<313> RELEVANT RESIDUES IN SEQ ID NO: (1)..(1503)

<400> SEQUENCE: 10

| | | |
|---|---|---|
| ttggagtttc gccgagcaaa gcctgccaac cctcaaaata gcgcccggcc tgtgcgtgct | 60 |
| tcagcacgcc gtcccgcttt gcgggcgacg ggctgtgccc tctgcctaga aggaagtaag | 120 |
| ttgcgctacg acgtcgcgat aattggaggt ggcaacgctg cattgacggc agccgtgacg | 180 |
| gcgcgtgaag cggggggcctc ggttcttgtg atcgagcatg cgccgcgcgc catgcgcggc | 240 |
| ggcaacagtc gtcacacacg caatatgcgt acgatgcacg aacgtcccct gtcgccgttg | 300 |
| accggtgaat attcggcgga cgaatattgg aatgatcttg tccgcgtcac gggggggcgc | 360 |
| accgacgaag aactcgcgcg gctcgttatc cgcaacacca ccgacgctat tcccttcatg | 420 |
| acgcgctgcg gtgtgcgttt ccagccctcg ctgtcgggca cgctgagttt atcgcgaacc | 480 |
| aacgcattct tccttggcgg cgggaaggcg cttgtaaacg catattacgc cacggccgaa | 540 |
| cggctaggcg tcgatattct ctatgattct gaggtgaccg agatcaacct tcagcaaggc | 600 |
| gtcgtgcagc gtctgcaatt gcgcagccgg ggattccctg tcgaagtgga agccaaggct | 660 |
| gccatcgcct cgtccggagg attccaggca aatcttgact ggctctcaag cgcatggggg | 720 |
| cctgctgcgg cgaacttcat cgtacggggc acgccatatg cgactggcac ggtgctcaag | 780 |
| aacctgttgg agcaaggcgt cgcctcggtg ggagatccaa cccaatgcca tgctgtcgcg | 840 |
| atcgatgggc gagcgcccaa atacgacggc ggcatcgtca cacgactgga ctgcgttccc | 900 |
| ttctcgatcg tcgtcaacaa ggacgccttg cgcttctacg atgaaggcga agatgtgtgg | 960 |
| ccgaagcgtt acgccatatg gggtcgcttg gtggcacagc agcctgatca gatcgctttc | 1020 |
| agcataatcg atcggcaggc cgaagacctc ttcatgccgt cagtgttccc ccccgtgcaa | 1080 |
| gcggacacga tcgcgggtct ggccgagaaa ctcggtctga atcccgtaac cctggaacgc | 1140 |
| acggtggccg aattcaacgc cgcatgcgtg cccggcgaat tcggcggcca agatctcgac | 1200 |
| gacctccaca ccgagggaat cgaaccaaag aaatccaact gggcccgacc gattattgtg | 1260 |
| cccccgttca gcgcctatcc tctccggccc gggatcacct tcacctatct cggcgtcaag | 1320 |
| gtagacagcc gtgcgcgggt catcatggag acaggtgagc cgacaaaaaa cctgtttgct | 1380 |
| tcggggaaa taatggcggg cagcattctc ggccaaggtt atctcgctgg attggaatg | 1440 |
| gcgattggta ccgtattcgg ccgcatcgcg ggttgggagg ccgcacgtca tgcaggattt | 1500 |
| tga | 1503 |

<210> SEQ ID NO 11
<211> LENGTH: 500
<212> TYPE: PRT
<213> ORGANISM: Sphingopyxis sp.
<220> FEATURE:
<223> OTHER INFORMATION: Seq ID 11 (FumE)
<300> PUBLICATION INFORMATION:
<308> DATABASE ACCESSION NUMBER: FJ426269
<309> DATABASE ENTRY DATE: 2009-06-11
<313> RELEVANT RESIDUES IN SEQ ID NO: (1)..(500)

```
<400> SEQUENCE: 11

Leu Glu Phe Arg Arg Ala Lys Pro Ala Asn Pro Gln Asn Ser Ala Arg
1               5                   10                  15

Pro Val Arg Ala Ser Ala Arg Arg Pro Ala Leu Arg Ala Thr Gly Cys
            20                  25                  30

Ala Leu Cys Leu Glu Gly Ser Lys Leu Arg Tyr Asp Val Ala Ile Ile
        35                  40                  45

Gly Gly Gly Asn Ala Ala Leu Thr Ala Ala Val Thr Ala Arg Glu Ala
    50                  55                  60

Gly Ala Ser Val Leu Val Ile Glu His Ala Pro Arg Ala Met Arg Gly
65                  70                  75                  80

Gly Asn Ser Arg His Thr Arg Asn Met Arg Thr Met His Glu Arg Pro
                85                  90                  95

Leu Ser Pro Leu Thr Gly Glu Tyr Ser Ala Asp Glu Tyr Trp Asn Asp
            100                 105                 110

Leu Val Arg Val Thr Gly Gly Arg Thr Asp Glu Leu Ala Arg Leu
            115                 120                 125

Val Ile Arg Asn Thr Thr Asp Ala Ile Pro Phe Met Thr Arg Cys Gly
130                 135                 140

Val Arg Phe Gln Pro Ser Leu Ser Gly Thr Leu Ser Leu Ser Arg Thr
145                 150                 155                 160

Asn Ala Phe Phe Leu Gly Gly Gly Lys Ala Leu Val Asn Ala Tyr Tyr
                165                 170                 175

Ala Thr Ala Glu Arg Leu Gly Val Asp Ile Leu Tyr Asp Ser Glu Val
            180                 185                 190

Thr Glu Ile Asn Leu Gln Gln Gly Val Val Gln Arg Leu Gln Leu Arg
            195                 200                 205

Ser Arg Gly Phe Pro Val Glu Val Glu Ala Lys Ala Ala Ile Ala Ser
210                 215                 220

Ser Gly Gly Phe Gln Ala Asn Leu Asp Trp Leu Ser Ser Ala Trp Gly
225                 230                 235                 240

Pro Ala Ala Ala Asn Phe Ile Val Arg Gly Thr Pro Tyr Ala Thr Gly
                245                 250                 255

Thr Val Leu Lys Asn Leu Leu Glu Gln Gly Val Ala Ser Val Gly Asp
            260                 265                 270

Pro Thr Gln Cys His Ala Val Ala Ile Asp Gly Arg Ala Pro Lys Tyr
            275                 280                 285

Asp Gly Gly Ile Val Thr Arg Leu Asp Cys Val Pro Phe Ser Ile Val
290                 295                 300

Val Asn Lys Asp Ala Leu Arg Phe Tyr Asp Glu Gly Glu Asp Val Trp
305                 310                 315                 320

Pro Lys Arg Tyr Ala Ile Trp Gly Arg Leu Val Ala Gln Gln Pro Asp
                325                 330                 335

Gln Ile Ala Phe Ser Ile Ile Asp Arg Gln Ala Glu Asp Leu Phe Met
            340                 345                 350

Pro Ser Val Phe Pro Pro Val Gln Ala Asp Thr Ile Ala Gly Leu Ala
            355                 360                 365

Glu Lys Leu Gly Leu Asn Pro Val Thr Leu Glu Arg Thr Val Ala Glu
370                 375                 380

Phe Asn Ala Ala Cys Val Pro Gly Glu Phe Gly Gln Asp Leu Asp
385                 390                 395                 400

Asp Leu His Thr Glu Gly Ile Glu Pro Lys Lys Ser Asn Trp Ala Arg
                405                 410                 415
```

```
Pro Ile Ile Val Pro Pro Phe Ser Ala Tyr Pro Leu Arg Pro Gly Ile
            420                 425                 430

Thr Phe Thr Tyr Leu Gly Val Lys Val Asp Ser Arg Ala Arg Val Ile
            435                 440                 445

Met Glu Thr Gly Glu Pro Thr Lys Asn Leu Phe Ala Ser Gly Glu Ile
            450                 455                 460

Met Ala Gly Ser Ile Leu Gly Gln Gly Tyr Leu Ala Gly Phe Gly Met
465                 470                 475                 480

Ala Ile Gly Thr Val Phe Gly Arg Ile Ala Gly Trp Glu Ala Ala Arg
                485                 490                 495

His Ala Gly Phe
            500

<210> SEQ ID NO 12
<211> LENGTH: 1173
<212> TYPE: DNA
<213> ORGANISM: Sphingopyxis sp.
<220> FEATURE:
<223> OTHER INFORMATION: Seq ID 12 (fumF)
<300> PUBLICATION INFORMATION:
<308> DATABASE ACCESSION NUMBER: FJ426269
<309> DATABASE ENTRY DATE: 2009-06-11
<313> RELEVANT RESIDUES IN SEQ ID NO: (1)..(1173)

<400> SEQUENCE: 12
atgcaggatt tgatctcgt aaaaatgctg tctgacttgc cgtcggcgcc ggagctggaa      60
gccaggcgcg ttatggaggt gtgcaacgcg tgccgctatt gcgaagggtt ctgcgcggta     120
tttcctgcaa tgaccttgca gcgtcatttc gccagcggcg atctcagcca cctcgccaat     180
ctctgccact cgtgccaagg ttgctattac gcctgccaat acgcccctcc gcatgagttc     240
ggaataaacg ttccaaaggc gctgtcggag ttgcggctcg agagctacga gcagcatgct     300
tggccccggc cggtcgccgc tctctatcgc aagaatgcgc tcatcatttc catcttgtcg     360
gcggcatgca taaccggcgt ccttctgctt gccgccatct caacggggga tgcactttt      420 gcgaaacacg catcggtgcc cggcggcggg ttttacaacg ttattcctta tcaggcgatg     480
attgccgtcg cggcgaccac atttctttat ccgcgctgg cgctggcgat cagtctcgtt      540
cgcttttcgc ggacgatcgg tctgggaatt aaggttcttt atcagcacgt gccggttctt     600
cgggcgctac gcgatgcggc gactctgcga tatctcggcg gcagcgacgg cgaggggtgt     660
aacgacgcgg acgagacatt ttcgacgacc cggcgaaaat tcatcacgc ccttgcctat      720 ggcttcggac tttgtttcgc ggccacagcc acgggcacga tctacgatca tatgttcggc     780
tggccggcgc cctatgcgct tttcagcttg ccggtcgtcc tagggaccgt tgggggggatc    840 ggaatggtcg tgggcgcgat cggcctactc tggctcaagc tggccggcga agacgctcct     900
cgatcaccgg cactgcttgg gccggatgtt gccctgttgg tgcttctgct tgccatagcg     960
gcaacgggcc tcctccttt agcggtccgc agcaccgaag tcatgggcgt cgcgctcgcc     1020
gtccatctcg gcgtcgtctt ggccttcttt ttggtgatgc catacagcaa atttgtccac    1080
ggtatcttca ggctcacggc tctcgtgcgc catcatgctg accgcgaggc aagtaatggc    1140
ttcgcctcca gccctcccac gaaaaagggt taa                                  1173

<210> SEQ ID NO 13
<211> LENGTH: 390
<212> TYPE: PRT
<213> ORGANISM: Sphingopyxis sp.
<220> FEATURE:
<223> OTHER INFORMATION: Seq ID 13 (FumF)
```

```
<300> PUBLICATION INFORMATION:
<308> DATABASE ACCESSION NUMBER: FJ426269
<309> DATABASE ENTRY DATE: 2009-06-11
<313> RELEVANT RESIDUES IN SEQ ID NO: (1)..(390)

<400> SEQUENCE: 13

Met Gln Asp Phe Asp Leu Val Lys Met Leu Ser Asp Leu Pro Ser Ala
1               5                   10                  15

Pro Glu Leu Glu Ala Arg Arg Val Met Glu Val Cys Asn Ala Cys Arg
            20                  25                  30

Tyr Cys Glu Gly Phe Cys Ala Val Phe Pro Ala Met Thr Leu Gln Arg
        35                  40                  45

His Phe Ala Ser Gly Asp Leu Ser His Leu Ala Asn Leu Cys His Ser
    50                  55                  60

Cys Gln Gly Cys Tyr Tyr Ala Cys Gln Tyr Ala Pro Pro His Glu Phe
65                  70                  75                  80

Gly Ile Asn Val Pro Lys Ala Leu Ser Glu Leu Arg Leu Glu Ser Tyr
                85                  90                  95

Glu Gln His Ala Trp Pro Arg Pro Val Ala Ala Leu Tyr Arg Lys Asn
            100                 105                 110

Ala Leu Ile Ile Ser Ile Leu Ser Ala Ala Cys Ile Thr Gly Val Leu
        115                 120                 125

Leu Leu Ala Ala Ile Phe Asn Gly Asp Ala Leu Phe Ala Lys His Ala
    130                 135                 140

Ser Val Pro Gly Gly Gly Phe Tyr Asn Val Ile Pro Tyr Gln Ala Met
145                 150                 155                 160

Ile Ala Val Ala Ala Thr Thr Phe Leu Tyr Ser Leu Ala Leu Ala
                165                 170                 175

Ile Ser Leu Val Arg Phe Ser Arg Thr Ile Gly Leu Gly Ile Lys Val
            180                 185                 190

Leu Tyr Gln His Val Pro Val Leu Arg Ala Leu Arg Asp Ala Ala Thr
        195                 200                 205

Leu Arg Tyr Leu Gly Gly Ser Asp Gly Glu Gly Cys Asn Asp Ala Asp
    210                 215                 220

Glu Thr Phe Ser Thr Thr Arg Arg Lys Phe His His Ala Leu Ala Tyr
225                 230                 235                 240

Gly Phe Gly Leu Cys Phe Ala Ala Thr Ala Thr Gly Thr Ile Tyr Asp
                245                 250                 255

His Met Phe Gly Trp Pro Ala Pro Tyr Ala Leu Phe Ser Leu Pro Val
            260                 265                 270

Val Leu Gly Thr Val Gly Gly Ile Gly Met Val Val Gly Ala Ile Gly
        275                 280                 285

Leu Leu Trp Leu Lys Leu Ala Gly Glu Asp Ala Pro Arg Ser Pro Ala
    290                 295                 300

Leu Leu Gly Pro Asp Val Ala Leu Leu Val Leu Leu Ala Ile Ala
305                 310                 315                 320

Ala Thr Gly Leu Leu Leu Leu Ala Val Arg Ser Thr Glu Val Met Gly
                325                 330                 335

Val Ala Leu Ala Val His Leu Gly Val Val Leu Ala Phe Phe Leu Val
            340                 345                 350

Met Pro Tyr Ser Lys Phe Val His Gly Ile Phe Arg Leu Thr Ala Leu
        355                 360                 365

Val Arg His His Ala Asp Arg Glu Ala Ser Asn Gly Phe Ala Ser Ser
    370                 375                 380

Pro Pro Thr Lys Lys Gly
```

-continued

<210> SEQ ID NO 14
<211> LENGTH: 1296
<212> TYPE: DNA
<213> ORGANISM: Sphingopyxis sp.
<220> FEATURE:
<223> OTHER INFORMATION: Seq ID 14 (fumG)
<300> PUBLICATION INFORMATION:
<308> DATABASE ACCESSION NUMBER: FJ426269
<309> DATABASE ENTRY DATE: 2009-06-11
<313> RELEVANT RESIDUES IN SEQ ID NO: (1)..(1296)

<400> SEQUENCE: 14

```
atggaacata tgaagtccgt tcgcgatcgc agtagcgtca tgcagatcgt gagagtggcg      60
agtggcaact gtctcgagca atatgatttc ttcgtttacg cttctatgc ggcatatatt     120
gcgagaagct ttttccgac cggcgataac gcgacatcgc tcatgctttc attggccact     180
tttggcgctg gttcctcat gaggcccttg ggggcgattt ttctcgggtc ctacatcgat     240
cgcgtcgggc gtcggaaagg cctgatcgtg acactcgcga tcatggccgt cggaaccctc     300
accattgcga tgactccaag ctatgaggca attggattac tcgcaccggt tatcgtgctc     360
gtcgggcgac ttttgcaggg ttttttccgct ggagcagagt cgggtggcgt ctcagtgtac     420
ttggcggaaa ttgcgtcgcc caaatcgaga ggcttcttca cctcgtggca gtctgccagc     480
cagcaggtgg ccgtcatgat cgccgccgcg atcggtcttg cgctgcaatc aacgctttca     540
ccggagcaaa tgaacgactg gggatggcgg gtgcccttgt tgatcggatg cttgattatc     600
cccgtgatac tctggctgcg ccggtctctc ccggaaacga aagcctatct ccacatggag     660
cacaaggcgc attcgatcgg cgaatccctc gcgaattgc aacagagctg ggggctgatc     720
ttgacgggca tggcgatgtc gatcctcacg acgaccacct tttacatgat taccgcctat     780
acgccgacat ttggcgagaa agcactcgga ctgagcccgc aagatgtcct gctggttacc     840
atcatggtcg gcgtgtcgaa cttcctgtgg cttccgatcg ggggtgctct ctcggatcgt     900
atcggtagaa ccccgatcct actggtcgtg ccggtcaccg ttctcgccat cgcctttccc     960
ctgatgagct ggctcgtcgc ggcaccgaca ttcggagcgc ttgcagctgt tctgctgact    1020
ttctccgcat gctttggact ctataatggg gcgctcatcg cgagactcac cgagattatg    1080
cctccccgcca ttagaaccct tggcttctcg ctggcgttca gtctcgcgac ctcgctgttc    1140
ggcggcttca ccccattggt aagtacggcg ctaatccacg cgacgggcag caattccgcg    1200
cctgcaatct ggctctgttt tgcggctttc atcagcttcg tcggtgtggc cgcatcgacc    1260
cggctgagcc ggccaatcgc cgaaggcgcc agatag                              1296
```

<210> SEQ ID NO 15
<211> LENGTH: 431
<212> TYPE: PRT
<213> ORGANISM: Sphingopyxis sp.
<220> FEATURE:
<223> OTHER INFORMATION: Seq ID 15 (FumG)
<300> PUBLICATION INFORMATION:
<308> DATABASE ACCESSION NUMBER: FJ426269
<309> DATABASE ENTRY DATE: 2009-06-11
<313> RELEVANT RESIDUES IN SEQ ID NO: (1)..(431)

<400> SEQUENCE: 15

Met Glu His Met Lys Ser Val Arg Asp Arg Ser Val Met Gln Ile
1               5                   10                  15
Val Arg Val Ala Ser Gly Asn Cys Leu Glu Gln Tyr Asp Phe Phe Val
                20                  25                  30

Tyr Gly Phe Tyr Ala Ala Tyr Ile Ala Arg Ser Phe Phe Pro Thr Gly
            35                  40                  45

Asp Asn Ala Thr Ser Leu Met Leu Ser Leu Ala Thr Phe Gly Ala Gly
 50                  55                  60

Phe Leu Met Arg Pro Leu Gly Ala Ile Phe Leu Gly Ser Tyr Ile Asp
 65                  70                  75                  80

Arg Val Gly Arg Lys Gly Leu Ile Val Thr Leu Ala Ile Met Ala
                85                  90                  95

Val Gly Thr Leu Thr Ile Ala Met Thr Pro Ser Tyr Glu Ala Ile Gly
            100                 105                 110

Leu Leu Ala Pro Val Ile Val Leu Val Gly Arg Leu Leu Gln Gly Phe
            115                 120                 125

Ser Ala Gly Ala Glu Ser Gly Gly Val Ser Val Tyr Leu Ala Glu Ile
    130                 135                 140

Ala Ser Pro Lys Ser Arg Gly Phe Phe Thr Ser Trp Gln Ser Ala Ser
145                 150                 155                 160

Gln Gln Val Ala Val Met Ile Ala Ala Ala Ile Gly Leu Ala Leu Gln
                165                 170                 175

Ser Thr Leu Ser Pro Glu Gln Met Asn Asp Trp Gly Trp Arg Val Pro
            180                 185                 190

Leu Leu Ile Gly Cys Leu Ile Ile Pro Val Ile Leu Trp Leu Arg Arg
            195                 200                 205

Ser Leu Pro Glu Thr Lys Ala Tyr Leu His Met Glu His Lys Ala His
    210                 215                 220

Ser Ile Gly Glu Ser Leu Arg Glu Leu Gln Gln Ser Trp Gly Leu Ile
225                 230                 235                 240

Leu Thr Gly Met Ala Met Ser Ile Leu Thr Thr Thr Phe Tyr Met
                245                 250                 255

Ile Thr Ala Tyr Thr Pro Thr Phe Gly Glu Lys Ala Leu Gly Leu Ser
                260                 265                 270

Pro Gln Asp Val Leu Leu Val Thr Ile Met Val Gly Val Ser Asn Phe
            275                 280                 285

Leu Trp Leu Pro Ile Gly Gly Ala Leu Ser Asp Arg Ile Gly Arg Thr
    290                 295                 300

Pro Ile Leu Leu Val Val Pro Val Thr Val Leu Ala Ile Ala Phe Pro
305                 310                 315                 320

Leu Met Ser Trp Leu Val Ala Ala Pro Thr Phe Gly Ala Leu Ala Ala
                325                 330                 335

Val Leu Leu Thr Phe Ser Ala Cys Phe Gly Leu Tyr Asn Gly Ala Leu
            340                 345                 350

Ile Ala Arg Leu Thr Glu Ile Met Pro Pro Ala Ile Arg Thr Leu Gly
            355                 360                 365

Phe Ser Leu Ala Phe Ser Leu Ala Thr Ser Leu Phe Gly Gly Phe Thr
    370                 375                 380

Pro Leu Val Ser Thr Ala Leu Ile His Ala Thr Gly Ser Asn Ser Ala
385                 390                 395                 400

Pro Ala Ile Trp Leu Cys Phe Ala Phe Ile Ser Phe Val Gly Val
                405                 410                 415

Ala Ala Ser Thr Arg Leu Ser Arg Pro Ile Ala Glu Gly Ala Arg
            420                 425                 430

<210> SEQ ID NO 16
<211> LENGTH: 1071
<212> TYPE: DNA
<213> ORGANISM: Sphingopyxis sp.

<220> FEATURE:
<223> OTHER INFORMATION: Seq ID 16 (fumH)
<300> PUBLICATION INFORMATION:
<308> DATABASE ACCESSION NUMBER: FJ426269
<309> DATABASE ENTRY DATE: 2009-06-11
<313> RELEVANT RESIDUES IN SEQ ID NO: (1)..(1071)

<400> SEQUENCE: 16

```
atgagagcag tagtttaccg aaatggcgaa cttgtcctgg gggcctatgc tgatccgata      60
cccgccgccg ggcaggtgct cgtcaagacc agagcatgcg gcatctgcgg atctgacctt    120
cattttgcg atcatgcgca ggcgtttacg aaccttgcat cgcgggcggg tatcgcctct     180
atggaagttg atttgtgtcg agacatcgtt ctggggcatg aattctgtgg cgagattatg    240
gagttcgggc cctctgcgga tcgtcgcttc aaacccggac agcttgtgtg ctcgctgccg    300
ctggcgatcg gtccgaccgg agcgcggacg attggctact cggatgagta tcccggcggg    360
ctcggcgaat atatggtcct cacggaagcg ctcttgctgc ctgttccgaa cggccttccg    420
gcgacctgcg cggcgttgac ggagccgatg gcggtgggat ggcatgccgt cgagatcgcg    480
caggttcaac cacatcacat ccctgtggtg atcgggtgcg accggtcgg gttggcagtc    540
gtcgctgccc tgaaacataa gcaagttgct ccgattattg cgtcggatcc atcgcccgat    600
cggcgtgctc ttgctctgcg gatgggcgcc gacgccgttg tcgatccgcg cgaagaatca    660
cccttcgcc aggccgagaa gatcgcacgc ccggtcggac aaggtggggc cctgtccagc    720
tcattgctgt caaagtctca aatgatattc gaatgcgtag gggtgccggg catgcttcgg    780
catgcgatgg acggcgcgtc cgacgggtcc gagatcatgg tcgttggcgc atgcatgcag    840
ccggacgcga tcgagcccat gatcgggatg tttaaagcgc tcacgatcaa attctcgcga    900
acttacacgg gtgaggaatt cgccgcggtg cttcacatga taggtgaggg cgcactcgac    960
gtatctccgc tcgttaccga tgtgattggc ctgtccgatg tcccgtccgc gtttgaggct   1020
ctacggagtc caggcgccca agcaaaagtg attgtggacc cttggcgctg a            1071
```

<210> SEQ ID NO 17
<211> LENGTH: 356
<212> TYPE: PRT
<213> ORGANISM: Sphingopyxis sp.
<220> FEATURE:
<223> OTHER INFORMATION: Seq ID 17 (FumH)
<300> PUBLICATION INFORMATION:
<308> DATABASE ACCESSION NUMBER: FJ426269
<309> DATABASE ENTRY DATE: 2009-06-11
<313> RELEVANT RESIDUES IN SEQ ID NO: (1)..(356)

<400> SEQUENCE: 17

```
Met Arg Ala Val Val Tyr Arg Asn Gly Glu Leu Val Leu Gly Ala Tyr
1               5                   10                  15

Ala Asp Pro Ile Pro Ala Ala Gly Gln Val Leu Val Lys Thr Arg Ala
            20                  25                  30

Cys Gly Ile Cys Gly Ser Asp Leu His Phe Cys Asp His Ala Gln Ala
        35                  40                  45

Phe Thr Asn Leu Ala Ser Arg Ala Gly Ile Ala Ser Met Glu Val Asp
    50                  55                  60

Leu Cys Arg Asp Ile Val Leu Gly His Glu Phe Cys Gly Glu Ile Met
65                  70                  75                  80

Glu Phe Gly Pro Ser Ala Asp Arg Arg Phe Lys Pro Gly Gln Leu Val
                85                  90                  95

Cys Ser Leu Pro Leu Ala Ile Gly Pro Thr Gly Ala Arg Thr Ile Gly
            100                 105                 110
```

```
          Tyr Ser Asp Glu Tyr Pro Gly Gly Leu Gly Glu Tyr Met Val Leu Thr
              115                 120                 125

Glu Ala Leu Leu Pro Val Pro Asn Gly Leu Pro Ala Thr Cys Ala
          130                 135                 140

Ala Leu Thr Glu Pro Met Ala Val Gly Trp His Ala Val Glu Ile Ala
145                 150                 155                 160

Gln Val Gln Pro His His Ile Pro Val Val Ile Gly Cys Gly Pro Val
                165                 170                 175

Gly Leu Ala Val Val Ala Ala Leu Lys His Lys Gln Val Ala Pro Ile
            180                 185                 190

Ile Ala Ser Asp Pro Ser Pro Asp Arg Arg Ala Leu Ala Leu Arg Met
        195                 200                 205

Gly Ala Asp Ala Val Val Asp Pro Arg Glu Glu Ser Pro Phe Arg Gln
    210                 215                 220

Ala Glu Lys Ile Ala Arg Pro Val Gly Gln Gly Gly Ala Leu Ser Ser
225                 230                 235                 240

Ser Leu Leu Ser Lys Ser Gln Met Ile Phe Glu Cys Val Gly Val Pro
                245                 250                 255

Gly Met Leu Arg His Ala Met Asp Gly Ala Ser Asp Gly Ser Glu Ile
            260                 265                 270

Met Val Val Gly Ala Cys Met Gln Pro Asp Ala Ile Glu Pro Met Ile
        275                 280                 285

Gly Met Phe Lys Ala Leu Thr Ile Lys Phe Ser Arg Thr Tyr Thr Gly
    290                 295                 300

Glu Glu Phe Ala Ala Val Leu His Met Ile Gly Glu Gly Ala Leu Asp
305                 310                 315                 320

Val Ser Pro Leu Val Thr Asp Val Ile Gly Leu Ser Asp Val Pro Ser
                325                 330                 335

Ala Phe Glu Ala Leu Arg Ser Pro Gly Ala Gln Ala Lys Val Ile Val
            340                 345                 350

Asp Pro Trp Arg
        355
```

<210> SEQ ID NO 18
<211> LENGTH: 1269
<212> TYPE: DNA
<213> ORGANISM: Sphingopyxis sp.
<220> FEATURE:
<223> OTHER INFORMATION: Seq ID 18 (fumI)
<300> PUBLICATION INFORMATION:
<308> DATABASE ACCESSION NUMBER: FJ426269
<309> DATABASE ENTRY DATE: 2009-06-11
<313> RELEVANT RESIDUES IN SEQ ID NO: (1)..(1269)

<400> SEQUENCE: 18

```
atggcgaacg gaacaaggca gaaagatctc agagaacgcg ccgaacgggt cattccgggc      60
gggatgtacg ccacgagtc gacacggttg ctgccgccag aattccccca gttcttcagg     120
cgcgcgctgg gggcacgaat tgggacgcc gacgagcagc cctatatcga ctatatgtgc     180
gcgtatgggc caaatttgct cggttaccgg caatccgaaa tcgaagccgc ggctgatgcg     240
cagcgacttc tcggcgacac catgaccggt ccttcggaga tcatggtcaa cctcgccgaa     300
gcctttgtgg catggtccg tcatgcggat tgggcgatgt tctgcaaaaa tggcagcgat     360
gccacctcaa cggcgatggt tctcgcgcgt gcccatacgg ggcgcaaaac catattatgc     420
gccaaaggcg cctatcatgg cgcttccccg tggaacactc gcatactgc gggattctc     480 gcttccgatc gcgtgcatgt cgcatattat acctataacg acgcccaaag cttatcggac     540
```

```
gcgttcaagg cgcacgatgg cgatattgcg gctgtctttg ccacaccttt ccgacacgaa    600
gtatttgagg accaggccct cgcccagctt gagttcgcgc gcaccgctcg aaaatgttgt    660
gacgagaccg gtgcgcttct ggtcgttgac gatgtgcgcg caggtttccg ggtggcgcgc    720
gattgcagct ggacgcattt gggtatcgaa cccgatctca gttgctgggg aaaatgcttt    780
gcgaatggct atccgatctc cgccctgctg ggctcgaaca aggcgcgcga tgcggcgcgg    840
gatatatttg tgaccggctc cttctggttc tctgcggtac cgatggcggc cgcgatcgaa    900
accctcagga tcattcgaga gacgccttat ctcgaaacgc tgatcgccag cggcgccgcc    960
ctgcgggcag gcctggaggc acagtctcag cgccatggtc ttgagttgaa gcagacgggc   1020
ccggcgcaga tgccgcaaat attctttgcg gacgatcccg attttcggat cggctatgcg   1080
tgggccgcgg cgtgcctgaa gggcggcgtc tatgttcatc cctatcacaa tatgtttctc   1140
tctgcggccc atacagttga cgatgtaacg gagaccctcg aggcgacgga tcgcgcgttc   1200
agcgcggtcc tcagagattt tgcgtctctc cagcctcatc ccatttttaat gcaactcgcc   1260 ggtgcttga                                                            1269
```

<210> SEQ ID NO 19
<211> LENGTH: 422
<212> TYPE: PRT
<213> ORGANISM: Sphingopyxis sp.
<220> FEATURE:
<223> OTHER INFORMATION: Seq ID 19 (FumI)
<300> PUBLICATION INFORMATION:
<308> DATABASE ACCESSION NUMBER: FJ426269
<309> DATABASE ENTRY DATE: 2009-06-11
<313> RELEVANT RESIDUES IN SEQ ID NO: (1)..(422)

<400> SEQUENCE: 19

```
Met Ala Asn Gly Thr Arg Gln Lys Asp Leu Arg Glu Arg Ala Glu Arg
1               5                  10                  15

Val Ile Pro Gly Gly Met Tyr Gly His Glu Ser Thr Arg Leu Leu Pro
            20                  25                  30

Pro Glu Phe Pro Gln Phe Phe Arg Arg Ala Leu Gly Ala Arg Ile Trp
        35                  40                  45

Asp Ala Asp Glu Gln Pro Tyr Ile Asp Tyr Met Cys Ala Tyr Gly Pro
    50                  55                  60

Asn Leu Leu Gly Tyr Arg Gln Ser Glu Ile Glu Ala Ala Asp Ala
65                  70                  75                  80

Gln Arg Leu Leu Gly Asp Thr Met Thr Gly Pro Ser Glu Ile Met Val
                85                  90                  95

Asn Leu Ala Glu Ala Phe Val Gly Met Val Arg His Ala Asp Trp Ala
            100                 105                 110

Met Phe Cys Lys Asn Gly Ser Asp Ala Thr Ser Thr Ala Met Val Leu
        115                 120                 125

Ala Arg Ala His Thr Gly Arg Lys Thr Ile Leu Cys Ala Lys Gly Ala
    130                 135                 140

Tyr His Gly Ala Ser Pro Trp Asn Thr Pro His Thr Ala Gly Ile Leu
145                 150                 155                 160

Ala Ser Asp Arg Val His Val Ala Tyr Tyr Thr Tyr Asn Asp Ala Gln
                165                 170                 175

Ser Leu Ser Asp Ala Phe Lys Ala His Asp Gly Asp Ile Ala Ala Val
            180                 185                 190

Phe Ala Thr Pro Phe Arg His Glu Val Phe Glu Asp Gln Ala Leu Ala
        195                 200                 205

Gln Leu Glu Phe Ala Arg Thr Ala Arg Lys Cys Cys Asp Glu Thr Gly
```

```
                210                 215                 220
Ala Leu Leu Val Val Asp Asp Val Arg Ala Gly Phe Arg Val Ala Arg
225                 230                 235                 240

Asp Cys Ser Trp Thr His Leu Gly Ile Glu Pro Asp Leu Ser Cys Trp
            245                 250                 255

Gly Lys Cys Phe Ala Asn Gly Tyr Pro Ile Ser Ala Leu Leu Gly Ser
        260                 265                 270

Asn Lys Ala Arg Asp Ala Ala Arg Asp Ile Phe Val Thr Gly Ser Phe
    275                 280                 285

Trp Phe Ser Ala Val Pro Met Ala Ala Ala Ile Glu Thr Leu Arg Ile
290                 295                 300

Ile Arg Glu Thr Pro Tyr Leu Glu Thr Leu Ile Ala Ser Gly Ala Ala
305                 310                 315                 320

Leu Arg Ala Gly Leu Glu Ala Gln Ser Gln Arg His Gly Leu Glu Leu
            325                 330                 335

Lys Gln Thr Gly Pro Ala Gln Met Pro Gln Ile Phe Phe Ala Asp Asp
        340                 345                 350

Pro Asp Phe Arg Ile Gly Tyr Ala Trp Ala Ala Ala Cys Leu Lys Gly
    355                 360                 365

Gly Val Tyr Val His Pro Tyr His Asn Met Phe Leu Ser Ala Ala His
370                 375                 380

Thr Val Asp Asp Val Thr Glu Thr Leu Glu Ala Thr Asp Arg Ala Phe
385                 390                 395                 400

Ser Ala Val Leu Arg Asp Phe Ala Ser Leu Gln Pro His Pro Ile Leu
            405                 410                 415

Met Gln Leu Ala Gly Ala
        420

<210> SEQ ID NO 20
<211> LENGTH: 2835
<212> TYPE: DNA
<213> ORGANISM: Sphingopyxis sp.
<220> FEATURE:
<223> OTHER INFORMATION: Seq ID 20 (fumJ)
<300> PUBLICATION INFORMATION:
<308> DATABASE ACCESSION NUMBER: FJ426269
<309> DATABASE ENTRY DATE: 2009-06-11
<313> RELEVANT RESIDUES IN SEQ ID NO: (1)..(2835)

<400> SEQUENCE: 20
atgtatcgga agttcagaat cgaaaagccc ggcaaggcaa atagtttgct cggcgcagta      60
gcgctcggca ccctcgcatt tcctgtctct gccagtgctc aggatagcga tcccgcatcg     120
ataggtcagc cggacgaagc ggacacggac cggggaacga gcgaaatcgt cgtgaccggc     180
agccgcctcc agaacggctt caattcgccg acgccggtta cagccgtatc cagcgagcag     240
ttgaaggagg catctccgac caaccttgcc gacgcactca accagctgcc cgtgttcaac     300
gacagcttga agacctccaa ccctggcacg acacccggaa cggggaacag cggtcagaac     360
ctgctcaaca tgcgcggcct cgggtcaaac cggaacctcg tcctgctgaa cggcaaccgt     420
ttcgtcgcga ccaatttcac aggctcggtc gatatcaacg tgctgccgca ggcgttggtc     480
aagcgcgtcg atgtcgtgac gggcggcgcc tcggccgcct acggttccga tgccgtttcg     540
ggcgtcatca acttcgtgct cgacgaagat ctggaaggca tcagggccga gctccagtcg     600
ggtgttttcaa cccgcggcga cctcccgtcc tacggcggtt cgatcgcctt cggcacttcg     660
tttgccgacg accggttgca cttgctcggc agcttcgaat attttcgaca ggacggaatc     720
cgggccgatg aagcaacggg tcgccgctgg ttcgacatcg ccgccggcca atatcccgtg     780
```

```
cccggcgcta cgacaggcgt cacggtcgtg cccgatattc gcagttctcg cggatcctac    840
ggcggacttg tcacgtccgg ccctctgaaa ggcatcgcgt ttttgcccgg aggagtccta    900
gggaccttcg actacgggaa ttttacgagc tcgtcgttcc agagcggcgg cgatggaccg    960
cgcgtgaata tcggcttcgc cccggatcag cttcgctaca acgcgttcct acgcgccgca   1020
tatgatgtgt ccgacactgt gcaggtgtat gcggagggca cctatgctta ttcccacacc   1080
aacctgggtg cattcgtaat atcgcatgtc ggtggctcga ataatttccg gatcttccgt   1140
gataacgcct tccttccggc tccactcgcg acgctcatgg acagaaatgc ccaggcttcg   1200
atcgttgtcg gtcgcttctc aagcgacttt cccttggtcg aaatcgagaa tttcgcaaag   1260
gtctaccgcg cgctgccgg cttccgggca gacattggca atggctggaa actcgatggc   1320
tcggcctcct ttggccttac ggacctcgag cttcgtgaaa acaatctcac catcaaccgc   1380
aatctctacg ccgccgtcga tgcggtccgc gatcccgcgg gcaatatcgt ctgccgttca   1440
acactggccg gcctcgacca agattgcgtg ccgctcaatc tcttcggcac aggctcgccg   1500
agcgcgtcgg ccatcgacta tgtcaccgct gatggcgtcg ctcagctgag gcttgagcaa   1560
tatgtggcgg gactcacgat ttccggcgac ctcggcgata gcctgtcgtt cggcgcgggc   1620
ccggtctcgg tcgccgctgg tatcgaatat cgcaaggaga aggcccggca ggaaaccgac   1680
gcgatatcgc aggcgacgac ctcgatcacg ggaatcaggg gggctccggc ggcgcaggca   1740
ggtcggcctg gaggcttcaa tctctacaac ccacttccct tctcgggaag ctatgacatc   1800
aaggaaggtt ttgtcgaaat cggcgtcccg attctgaagg acagcgcgct gggacgttcg   1860
ctgaacttaa acggcgccgt ccgatatgcc gattacagcc agtccggtgg agtaacaacc   1920
tggaagctgg gcgagaata tgagccgatc gacggcctca ggttccgcgc gacccgttcg   1980
cgagatatcc gcgggccaag ccttgtcgag ctattcgacc ccggccgtca ggcgacgctc   2040
aattcaattt atgccggaca ggctgtgcag acgcggttct ttaccgccgg caacgcggat   2100
ttgcgccctg aaaaggcgga cgtccttaca ttcggcgcgg tgctacgccc cgccttcgtg   2160
ccggggtttc agttttcggt cgatcgctat gtggtgaagg tgaagggcgc gatcgatttc   2220
ctccttcccc agcaggaaat cgacgcgtgc gatgcaggaa acaccttctt ctgcgacctc   2280
ataacggaga atccggacgg caccatcaca gtgacgggtc ccaatctcaa cctggctgtc   2340
cagaaagcgg cgggaattga cttcgaggcc tattactcac gccccgtcgg cggcggcacg   2400
ttcagtcttc gtgcgctggc aacgcaccat acctctgcct atcgcatcgc gaccggctcg   2460
gcgcccatcc gttcgctcgg acaaccggac acgccaaaat ggtcggccaa cttccaggcg   2520
cgatattcga ccgacgattg ggcgcttctc gtgcagcagc gcttcatcgc agcatcggtg   2580
ttcaatgccg acaatgtgga gggcgtcgat acgaatttga accacgctcc ggcggtttgg   2640
tacaccgacg cgacattgac cttcgacatc gcggcttttg gccagaagca gcagctgttt   2700
ctatcggtca ataatttgtt cgaccgagat ccgccaatag cgacgaacga ccccagcagt   2760
ttttccagcc cgaccagctc tgcctatgat ccggtcggcc gctattttaa tgtcggggtc   2820
cgtttccgga tctga                                                    2835
```

<210> SEQ ID NO 21
<211> LENGTH: 944
<212> TYPE: PRT
<213> ORGANISM: Sphingopyxis sp.
<220> FEATURE:
<223> OTHER INFORMATION: Seq ID 21 (FumJ)
<300> PUBLICATION INFORMATION:
<308> DATABASE ACCESSION NUMBER: FJ426269

<309> DATABASE ENTRY DATE: 2009-06-11
<313> RELEVANT RESIDUES IN SEQ ID NO: (1)..(944)

<400> SEQUENCE: 21

```
Met Tyr Arg Lys Phe Arg Ile Glu Lys Pro Gly Lys Ala Asn Ser Leu
1               5                   10                  15

Leu Gly Ala Val Ala Leu Gly Thr Leu Ala Phe Pro Val Ser Ala Ser
            20                  25                  30

Ala Gln Asp Ser Asp Pro Ala Ser Ile Gly Gln Pro Asp Glu Ala Asp
        35                  40                  45

Thr Asp Arg Gly Thr Ser Glu Ile Val Val Thr Gly Ser Arg Leu Gln
    50                  55                  60

Asn Gly Phe Asn Ser Pro Thr Pro Val Thr Ala Val Ser Ser Glu Gln
65                  70                  75                  80

Leu Lys Glu Ala Ser Pro Thr Asn Leu Ala Asp Ala Leu Asn Gln Leu
                85                  90                  95

Pro Val Phe Asn Asp Ser Leu Lys Thr Ser Asn Pro Gly Thr Thr Pro
            100                 105                 110

Gly Thr Gly Asn Ser Gly Gln Asn Leu Leu Asn Met Arg Gly Leu Gly
        115                 120                 125

Ser Asn Arg Asn Leu Val Leu Leu Asn Gly Asn Arg Phe Val Ala Thr
    130                 135                 140

Asn Phe Thr Gly Ser Val Asp Ile Asn Val Leu Pro Gln Ala Leu Val
145                 150                 155                 160

Lys Arg Val Asp Val Val Thr Gly Gly Ala Ser Ala Ala Tyr Gly Ser
                165                 170                 175

Asp Ala Val Ser Gly Val Ile Asn Phe Val Leu Asp Glu Asp Leu Glu
            180                 185                 190

Gly Ile Arg Ala Glu Leu Gln Ser Gly Val Ser Thr Arg Gly Asp Leu
        195                 200                 205

Pro Ser Tyr Gly Gly Ser Ile Ala Phe Gly Thr Ser Phe Ala Asp Asp
    210                 215                 220

Arg Leu His Leu Leu Gly Ser Phe Glu Tyr Phe Arg Gln Asp Gly Ile
225                 230                 235                 240

Arg Ala Asp Glu Ala Thr Gly Arg Arg Trp Phe Asp Ile Ala Ala Gly
                245                 250                 255

Gln Tyr Pro Val Pro Gly Ala Thr Thr Gly Val Thr Val Val Pro Asp
            260                 265                 270

Ile Arg Ser Ser Arg Gly Ser Tyr Gly Gly Leu Val Thr Ser Gly Pro
        275                 280                 285

Leu Lys Gly Ile Ala Phe Leu Pro Gly Gly Val Leu Gly Thr Phe Asp
    290                 295                 300

Tyr Gly Asn Phe Thr Ser Ser Phe Gln Ser Gly Gly Asp Gly Pro
305                 310                 315                 320

Arg Val Asn Ile Gly Phe Ala Pro Asp Gln Leu Arg Tyr Asn Ala Phe
                325                 330                 335

Leu Arg Ala Ala Tyr Asp Val Ser Asp Thr Val Gln Val Tyr Ala Glu
            340                 345                 350

Gly Thr Tyr Ala Tyr Ser His Thr Asn Leu Gly Ala Phe Val Ile Ser
        355                 360                 365

His Val Gly Gly Ser Asn Asn Phe Arg Ile Phe Arg Asp Asn Ala Phe
    370                 375                 380

Leu Pro Ala Pro Leu Ala Thr Leu Met Asp Arg Asn Ala Gln Ala Ser
385                 390                 395                 400
```

-continued

Ile Val Val Gly Arg Phe Ser Ser Asp Phe Pro Leu Val Glu Ile Glu
            405                 410                 415

Asn Phe Ala Lys Val Tyr Arg Gly Ala Ala Gly Phe Arg Ala Asp Ile
        420                 425                 430

Gly Asn Gly Trp Lys Leu Asp Gly Ser Ala Ser Phe Gly Leu Thr Asp
        435                 440                 445

Leu Glu Leu Arg Glu Asn Asn Leu Thr Ile Asn Arg Asn Leu Tyr Ala
    450                 455                 460

Ala Val Asp Ala Val Arg Asp Pro Ala Gly Asn Ile Val Cys Arg Ser
465                 470                 475                 480

Thr Leu Ala Gly Leu Asp Gln Asp Cys Val Pro Leu Asn Leu Phe Gly
            485                 490                 495

Thr Gly Ser Pro Ser Ala Ser Ala Ile Asp Tyr Val Thr Ala Asp Gly
            500                 505                 510

Val Ala Gln Leu Arg Leu Glu Gln Tyr Val Ala Gly Leu Thr Ile Ser
        515                 520                 525

Gly Asp Leu Gly Asp Ser Leu Ser Phe Gly Ala Gly Pro Val Ser Val
        530                 535                 540

Ala Ala Gly Ile Glu Tyr Arg Lys Glu Lys Ala Arg Gln Glu Thr Asp
545                 550                 555                 560

Ala Ile Ser Gln Ala Thr Thr Ser Ile Thr Gly Ile Arg Gly Ala Pro
            565                 570                 575

Ala Ala Gln Ala Gly Arg Pro Gly Gly Phe Asn Leu Tyr Asn Pro Leu
        580                 585                 590

Pro Phe Ser Gly Ser Tyr Asp Ile Lys Glu Gly Phe Val Glu Ile Gly
        595                 600                 605

Val Pro Ile Leu Lys Asp Ser Ala Leu Gly Arg Ser Leu Asn Leu Asn
    610                 615                 620

Gly Ala Val Arg Tyr Ala Asp Tyr Ser Gln Ser Gly Val Thr Thr
625                 630                 635                 640

Trp Lys Leu Gly Gly Glu Tyr Glu Pro Ile Asp Gly Leu Arg Phe Arg
            645                 650                 655

Ala Thr Arg Ser Arg Asp Ile Arg Gly Pro Ser Leu Val Glu Leu Phe
            660                 665                 670

Asp Pro Gly Arg Gln Ala Thr Leu Asn Ser Ile Tyr Gly Gly Gln Ala
        675                 680                 685

Val Gln Thr Arg Phe Phe Thr Ala Gly Asn Ala Asp Leu Arg Pro Glu
        690                 695                 700

Lys Ala Asp Val Leu Thr Phe Gly Ala Val Leu Arg Pro Ala Phe Val
705                 710                 715                 720

Pro Gly Phe Gln Phe Ser Val Asp Arg Tyr Val Val Lys Val Lys Gly
            725                 730                 735

Ala Ile Asp Phe Leu Leu Pro Gln Gln Glu Ile Asp Ala Cys Asp Ala
        740                 745                 750

Gly Asn Thr Phe Phe Cys Asp Leu Ile Thr Glu Asn Pro Asp Gly Thr
        755                 760                 765

Ile Thr Val Thr Gly Pro Asn Leu Asn Leu Ala Val Gln Lys Ala Ala
    770                 775                 780

Gly Ile Asp Phe Glu Ala Tyr Tyr Ser Arg Pro Val Gly Gly Gly Thr
785                 790                 795                 800

Phe Ser Leu Arg Ala Leu Ala Thr His His Thr Ser Ala Tyr Arg Ile
            805                 810                 815

Ala Thr Gly Ser Ala Pro Ile Arg Ser Leu Gly Gln Pro Asp Thr Pro
            820                 825                 830

```
Lys Trp Ser Ala Asn Phe Gln Ala Arg Tyr Ser Thr Asp Asp Trp Ala
            835                 840                 845

Leu Leu Val Gln Gln Arg Phe Ile Ala Ala Ser Val Phe Asn Ala Asp
    850                 855                 860

Asn Val Glu Gly Val Asp Thr Asn Leu Asn His Ala Pro Ala Val Trp
865                 870                 875                 880

Tyr Thr Asp Ala Thr Leu Thr Phe Asp Ile Ala Ala Phe Gly Gln Lys
                885                 890                 895

Gln Gln Leu Phe Leu Ser Val Asn Asn Leu Phe Asp Arg Asp Pro Pro
            900                 905                 910

Ile Ala Thr Asn Asp Pro Ser Ser Phe Ser Ser Pro Thr Ser Ser Ala
        915                 920                 925

Tyr Asp Pro Val Gly Arg Tyr Phe Asn Val Gly Val Arg Phe Arg Ile
    930                 935                 940

<210> SEQ ID NO 22
<211> LENGTH: 417
<212> TYPE: DNA
<213> ORGANISM: Sphingopyxis sp.
<220> FEATURE:
<223> OTHER INFORMATION: Seq ID 22 (fumK)
<300> PUBLICATION INFORMATION:
<308> DATABASE ACCESSION NUMBER: FJ426269
<309> DATABASE ENTRY DATE: 2009-06-11
<313> RELEVANT RESIDUES IN SEQ ID NO: (1)..(417)

<400> SEQUENCE: 22
atgcgcctca cgggcggaga attattggca cgatgtttgg ccgtcgaagg cgtccggtat      60
gtcttcggcc tcatgtcgcc ggaggtggat ccgctcctgg ctgcgctcga agacaatggg     120
atattgttcg tcccggtgcg gcacgaggcc gccgcagcct atatgccga gggcatttac     180 aagaccaccg acaggtcgc cgcgattgtc acgaatccgg gtcccggtac ggcaaacctt     240
ctgcctggag tcgtgacggc acgccacgaa ggggttccct cgtcgcaat aacgtcccag     300 catcaacttg gtgtcgttta tccctgcacg ccaaaaacct ttcagggaca agaccagatc     360
gacctctttc gacccgcggt taaatggggc gcacccatct tcgcctggaa ccggatt       417

<210> SEQ ID NO 23
<211> LENGTH: 139
<212> TYPE: PRT
<213> ORGANISM: Sphingopyxis sp.
<220> FEATURE:
<223> OTHER INFORMATION: Seq ID 23 (FumK)
<300> PUBLICATION INFORMATION:
<308> DATABASE ACCESSION NUMBER: FJ426269
<309> DATABASE ENTRY DATE: 2009-06-11
<313> RELEVANT RESIDUES IN SEQ ID NO: (1)..(139)

<400> SEQUENCE: 23

Met Arg Leu Thr Gly Gly Glu Leu Leu Ala Arg Cys Leu Ala Val Glu
1               5                   10                  15

Gly Val Arg Tyr Val Phe Gly Leu Met Ser Pro Glu Val Asp Pro Leu
            20                  25                  30

Leu Ala Ala Leu Glu Asp Asn Gly Ile Leu Phe Val Pro Val Arg His
        35                  40                  45

Glu Ala Ala Ala Tyr Met Ala Glu Gly Ile Tyr Lys Thr Thr Gly
    50                  55                  60

Gln Val Ala Ala Ile Val Thr Asn Pro Gly Pro Gly Thr Ala Asn Leu
65                  70                  75                  80

Leu Pro Gly Val Val Thr Ala Arg His Glu Gly Val Pro Phe Val Ala
```

```
                85                  90                  95
Ile Thr Ser Gln His Gln Leu Gly Val Val Tyr Pro Cys Thr Pro Lys
            100                 105                 110

Thr Phe Gln Gly Gln Asp Gln Ile Asp Leu Phe Arg Pro Ala Val Lys
        115                 120                 125

Trp Gly Ala Pro Ile Phe Ala Trp Asn Arg Ile
    130                 135

<210> SEQ ID NO 24
<211> LENGTH: 1272
<212> TYPE: DNA
<213> ORGANISM: Caulobacter sp.
<220> FEATURE:
<223> OTHER INFORMATION: Seq ID 24
<300> PUBLICATION INFORMATION:
<308> DATABASE ACCESSION NUMBER: FJ426269
<309> DATABASE ENTRY DATE: 2009-06-11
<313> RELEVANT RESIDUES IN SEQ ID NO: (1)..(1272)

<400> SEQUENCE: 24
atggaattga gccgccaacg agaccaggcc ttgagggagc gcgcccaagc ggtgatcccg      60
ggcgggatgt acggtcacga gtcgacctat ctgatgcccg agggcacgcc acagttcttc     120
agtcgcggca aggcgcccg actttgggac gccgacggca cgagtatgt cgattacatg       180 tgcgcctatg gccccaacct gctgggttac ggcttcgaac ccgtcgaagc ggccgccgca     240
gcccagcaag cccggggcga taccctgacc gggccgtcgg aggtgatggt gcagttggcg     300
gaagacttcg tcgcgcaaat cagccacgcg gactgggcca tgttctgcaa gaacggcaca     360
gacgccacct caatggcgat ggtcatcgcg cgcgcacaca ccggccggaa gacgatcctc     420
tgcgcgaaag cgccctatca tggggccgcg ccttggtgca cgccgatcct ggccggaacg     480
ctaccggagg atcgcgcctt tgtagtctac tacgactaca atgacgccca agcctcgtc      540 gacgccttcg aggcccatca ggacgacgtc gcggcgatct cgccacccc tcaccgtcac      600 gaggtgttca gcgaccagat cgatcctgat ccggaatatg cggccagcgt gcgggcgctc     660
tgcgacaaga gcggcgccct gctcgtcgtc gacgaagttc gagccgggtt caggatcgcg     720
cgcgactgca gctgggccaa gatcggcgtc gctccggatc tgagcacctg ggcaagtgc      780 ttcgccaacg gctatccgat ctcggcggtc ctaggggggcg aaaaggtgcg cagcgcggca    840
aaggccgtct acgtcaccgg ctcgttctgg ttctcggcca cgcccatggc cgcagccgtc    900
gaaaccctga gcaaatccg cgagaccgac tatctcgagc ggatcaacgc ggccgggacc     960
cgcctgcgcg agggcctgca gcagcaggct gctcacaacg gctttacgtt gcgccaaacg    1020
gggcccgtct ccatgcccca agtcctcttc gaggaagatc ccgattttcg ggtcggctac    1080
ggctgggttc gcgaatgcct gaagcgaggg gtgtacttca gccccctacca taacatgttc   1140 ctgtcggcgg cccatagcga ggcggacctg ccaagaccc ttgcggctac cggcgacgcc    1200
ttcgtcgagc tacgcgccaa gcttccgagc ctagaaatcc accaaccccct cctcgccctg   1260 agagcggcct aa                                                        1272

<210> SEQ ID NO 25
<211> LENGTH: 423
<212> TYPE: PRT
<213> ORGANISM: Caulobacter sp.
<220> FEATURE:
<223> OTHER INFORMATION: Seq  ID 25
<300> PUBLICATION INFORMATION:
<308> DATABASE ACCESSION NUMBER: FJ426269
<309> DATABASE ENTRY DATE: 2009-06-11
<313> RELEVANT RESIDUES IN SEQ ID NO: (1)..(423)
```

<400> SEQUENCE: 25

```
Met Glu Leu Ser Arg Gln Arg Asp Gln Ala Leu Arg Glu Arg Ala Gln
1               5                   10                  15

Ala Val Ile Pro Gly Gly Met Tyr Gly His Glu Ser Thr Tyr Leu Met
            20                  25                  30

Pro Glu Gly Thr Pro Gln Phe Phe Ser Arg Gly Lys Gly Ala Arg Leu
        35                  40                  45

Trp Asp Ala Asp Gly Asn Glu Tyr Val Asp Tyr Met Cys Ala Tyr Gly
    50                  55                  60

Pro Asn Leu Leu Gly Tyr Gly Phe Glu Pro Val Glu Ala Ala Ala Ala
65                  70                  75                  80

Ala Gln Gln Ala Arg Gly Asp Thr Leu Thr Gly Pro Ser Glu Val Met
                85                  90                  95

Val Gln Leu Ala Glu Asp Phe Val Ala Gln Ile Ser His Ala Asp Trp
            100                 105                 110

Ala Met Phe Cys Lys Asn Gly Thr Asp Ala Thr Ser Met Ala Met Val
        115                 120                 125

Ile Ala Arg Ala His Thr Gly Arg Lys Thr Ile Leu Cys Ala Lys Gly
130                 135                 140

Ala Tyr His Gly Ala Ala Pro Trp Cys Thr Pro Ile Leu Ala Gly Thr
145                 150                 155                 160

Leu Pro Glu Asp Arg Ala Phe Val Val Tyr Tyr Asp Tyr Asn Asp Ala
                165                 170                 175

Gln Ser Leu Val Asp Ala Phe Glu Ala His Gln Asp Asp Val Ala Ala
            180                 185                 190

Ile Phe Ala Thr Pro His Arg His Glu Val Phe Ser Asp Gln Ile Asp
        195                 200                 205

Pro Asp Pro Glu Tyr Ala Ala Ser Val Arg Ala Leu Cys Asp Lys Ser
    210                 215                 220

Gly Ala Leu Leu Val Val Asp Glu Val Arg Ala Gly Phe Arg Ile Ala
225                 230                 235                 240

Arg Asp Cys Ser Trp Ala Lys Ile Gly Val Ala Pro Asp Leu Ser Thr
                245                 250                 255

Trp Gly Lys Cys Phe Ala Asn Gly Tyr Pro Ile Ser Ala Val Leu Gly
            260                 265                 270

Gly Glu Lys Val Arg Ser Ala Ala Lys Ala Val Tyr Val Thr Gly Ser
        275                 280                 285

Phe Trp Phe Ser Ala Thr Pro Met Ala Ala Ala Val Glu Thr Leu Lys
290                 295                 300

Gln Ile Arg Glu Thr Asp Tyr Leu Glu Arg Ile Asn Ala Ala Gly Thr
305                 310                 315                 320

Arg Leu Arg Glu Gly Leu Gln Gln Ala Ala His Asn Gly Phe Thr
                325                 330                 335

Leu Arg Gln Thr Gly Pro Val Ser Met Pro Gln Val Leu Phe Glu Glu
            340                 345                 350

Asp Pro Asp Phe Arg Val Gly Tyr Gly Trp Val Arg Glu Cys Leu Lys
        355                 360                 365

Arg Gly Val Tyr Phe Ser Pro Tyr His Asn Met Phe Leu Ser Ala Ala
    370                 375                 380

His Ser Glu Ala Asp Leu Ala Lys Thr Leu Ala Ala Thr Gly Asp Ala
385                 390                 395                 400

Phe Val Glu Leu Arg Ala Lys Leu Pro Ser Leu Glu Ile His Gln Pro
                405                 410                 415
```

```
Leu Leu Ala Leu Arg Ala Ala
            420
```

METHOD FOR THE PRODUCTION OF AN ADDITIVE FOR THE ENZYMATIC DECOMPOSITION OF MYCOTOXINS, ADDITIVE, AND USE THEREOF

This is a national stage of PCT/AT09/000364 filed Sep. 18, 2009 and published in German, which claims the priority of Austria number GM 501/2008 filed Sep. 18, 2008, hereby incorporated by reference.

The present invention relates to a method for producing an additive for the enzymatic degradation of fumonisins, an additive for the enzymatic degradation of fumonisins, in vegetable raw materials and mixtures containing vegetable raw materials, as well as the use of genes.

Mycotoxins very frequently occur on agricultural vegetable products and, depending on the type of mycotoxins, inflict severe economic damage, in particular, in the foods produced from agricultural products and even in animals and humans fed with such foods, said damage being extremely manifold. Numerous methods have already been developed, trying to detoxify or degrade, or render harmless, such mycotoxins in order to inhibit any damage caused by mycotoxins in the fields of animal and human nutrition, animal breeding, food and feed processing and the like.

Known mycotoxins comprise a plurality of structurally interrelated mycotoxins such as, for instance, fumonisins, among which fumonisin B1 is the most frequently occurring toxin of the group. There are, however, numerous derivatives and related molecules which are also known to exhibit noxious effects in humans and animals. Thus, it is known that fumonisins impair the sphingolipid metabolism by interacting with the enzyme ceramide synthase. Sphingolipids not only are components of cell membranes, but also play an important role as signal and messenger molecules in many elementary cellular processes like cell growth, cell migration and cell binding, in inflammatory processes and intracellular transport procedures. Due to this impairment of the sphingolipid metabolism, fumonisins have been made responsible for the toxic effects on various animal species and also humans. It could, thus, demonstrated that fumonisins have cancerogenic effects in rodents, and, based on epidemiologic data, they have been associated with esophageal cancer and neural tube defects in humans. They have been held responsible for the typical toxicosis caused by pulmonary edemas, for instance, in various animal species such as, e.g., swine. In this context, fumonisins constitute an almost ubiquitous contamination source on various cereal crops, in particular corn as well as nuts and vegetables, and this strongly negative effect relating to the health of humans and animals is not to be neglected.

The microbial degradation of fumonisins has already been described in EP-A 1 860 954, according to which microorganisms are used to detoxify fumonisins and fumonisin derivatives by adding to feeds detoxifying bacteria or yeasts selected from precisely defined strains for detoxifying fumonisins.

Catabolic metabolic paths for the biological degradation of fumonisins and the genes and enzymes responsible therefor have already been described too. Thus, EP 0 988 383, for instance, describes fumonisin-detoxifying compositions and methods, wherein the fumonisin-degrading enzymes used are above all produced in transgenic plants in which the detoxification of fumonisins is effected using an amine oxidase that requires molecular oxygen for its enzymatic activity.

Moreover, WO 2004/085624 describes transaminases, deaminsases and aminomutases as well as compositions and methods for the enzymatic detoxification to detoxify, in particular, aminated toxins, e.g. fumonisins. In this context, polypeptides possessing deaminase activity are used for detoxification.

From WO 00/04158, the use of fumonisin-degrading amine oxidases in the production of foods or feeds and in the processing of vegetable raw materials has become known.

Hitherto known methods, however, have in common that, in order to detoxify mycotoxins, they require molecular oxygen for the described catabolic metabolic paths, yet the amine oxidases, which are particularly required, cannot work under oxygen-independent conditions. The use of such genes and enzymes for the detoxification of feeds, for instance in the digestive tracts of animals, is not possible because of the substantially oxygen-free environment in the digestive tracts of animals, the known genes and enzymes thus exhibiting no activity.

The invention aims to provide a method for producing an additive for the enzymatic degradation of mycotoxins, by which it is feasible to safely and reliably degrade to toxicologically harmless substances, or detoxify, fumonisins.

To solve these objects, the method according to the invention is conducted in a manner that at least one nucleic acid sequence of genes corresponding to sequences ID Nos. 1, 2, 4, 6, 8, 10, 12, 14, 16, 18, 20, 22 and 24 is provided, the at least one nucleic acid sequence is expressed in prokaryotic or eukaryotic host cells, and at least one thus prepared enzyme corresponding to sequences ID Nos. 3, 5, 7, 9, 11, 13, 15, 17, 19, 21, 23 and 25, optionally along with a cosubstrate, are used in a vegetable raw material. By providing at least one nucleic acid sequence of genes corresponding to sequences ID Nos. 1, 2, 4, 6, 8, 10, 12, 14, 16, 18, 20, 22 and 24, it is feasible to clone and express specific fumonisin- or mycotoxin-degrading genes, the expression being, for instance, conducted in E. coli and Pichia pastoris using standard processes, by which expression enzymes corresponding to sequences ID Nos. 3, 5, 7, 9, 11, 13, 15, 17, 19, 21, 23 and 25 will be obtained, wherein the at least one enzyme is optionally used along with a cosubstrate on a raw material to be treated. An additive produced according to such a method, on the one hand, allows for to completely and reliably degrade, for instance, mycotoxins directly on raw materials, with the specific enzymes produced by this method catalyzing the degradation of fumonisins and intermediates of the degradation path, and, on the other hand, allows for to degrade mycotoxins, for instance directly during the production of bioethanol in the mash for the production of alcohol, or to degrade and render harmless mycotoxins even during the production of foods directly in the production process.

Vegetable raw materials in this context include cereals or cereal products, grasses, fruits or vegetables and intermediate products containing these substances for the production of foods and feeds such as, for instance, silage, fruit mash or the like.

Additives in this context are especially feed additives, food additives as well as additives for the production of bioethanol.

A method of this type further enables to maintain the sphingolipid metabolism impaired by the interaction of fumonisins with the enzyme ceramide synthase while, at the same, biologically degrading the fumonisins to non-toxic substances. Finally, technological detoxification applications will be achieved since this method is also applicable on a larger technical scale, thus enabling the safe and reliable production of mycotoxin-free products by the method according to the invention.

The nucleic acid sequences used in the method according to the invention, and the enzymes expressed in prokaryotic and eukaryotic host cells by said nucleic acid sequences and catalytically acting in an oxygen-independent environment, are listed below.

```
Nucleic acids
Sequences:
>Seq ID 1 (fum (fumonisin catabolism) gene cluster, 15,420 bp)
TGTCGGCGATCRGTAAACTTCTACCGTGGTCCTCGTTCGCCCACAKCATACATCACAGACRTCGGGATTTCCAACTGAAC

GGGTCCCGGCCTGCCGGCCCACATTTCCCGGAACGCCATATGGGTGATTTCGACAATCCGGTTCCAGGCGAAGATGGGTG

CGCCCCATTTAACCGCGGGTCGAAAGAGGTCGATCTGGTCTTGTCCCTGAAAGGTTTTTGGCGTGCAGGGATAAACGACA

CCAAGTTGATGCTGGGACGTTATTGCGACGAAGGGAACCCCTTCGTGGCGTGCCGTCACGACTCCAGGCAGAAGGTTTGC

CGTACCGGGACCCGGATTCGTGACAATCGCGGCGACCTGTCCGGTGGTCTTGTAAATGCCCTCGGCCATATAGGCTGCGG

CGGCCTCGTGCCGCACCGGGACGAACAATATCCCATTGTCTTCGAGCGCAGCCAGGAGCGGATCCACCTCCGGCGACATG

AGGCCGAAGACATACCGGACGCCTTCGACGGCCAAACATCGTGCCAATAATTCTCCGCCCGTGAGGCGCATGACGATCTC

CAGTACGAAAGGTGAGTGCCCAGGTTCCGGCACATTCGCTGTGGTTAGTTGATGCGCTGATCGGCCAACCGACTGAGTGG

AGTTGGATGGCCGCACCTTACCCTGTCGCGCATAACTCTCAGATCCGGAAACGGACCCCGACATTAAAATAGCGGCCGAC

CGGATCATAGGCAGAGCTGGTCGGGCTGGAAAAACTGCTGGGGTCGTTCGTCGCTATTGGCGGATCTCGGTCGAACAAAT

TATTGACCGATAGAAACAGCTGCTGCTTCTGGCCAAAAGCCGCGATGTCGAAGGTCAATGTCGCGTCGGTGTACCAAACC

GCCGGAGCGTGGTTCAAATTCGTATCGACGCCCTCCACATTGTCGGCATTGAACACCGATGCTGCGATGAAGCGCTGCTG

CACGAGAAGCGCCCAATCGTCGGTCGAATATCGCGCCTGGAAGTTGGCCGACCATTTTGGCGTGTCCGGTTGTCCGAGCG

AACGGATGGGCGCCGAGCCGGTCGCGATGCGATAGGCAGAGGTATGGTGCGTTGCCAGCGCACGAAGACTGAACGTGCCG

CCGCCGACGGGCGTGAGTAATAGGCCTCGAAGTCAATTCCCGCCGCTTTCTGGACAGCCAGGTTGAGATTGGGACCCGT

CACTGTGATGGTGCCGTCCGGATTCTCCGTTATGAGGTCGCAGAAGAAGGTGTTTCCTGCATCGCACGCGTCGATTTCCT

GCTGGGGAAGGAGGAAATCGATCGCGCCCTTCACCTTCACCACATAGCGATCGACCGAAAACTGAAACCCCGGCACGAAG

GCGGGGCGTAGCACCGCGCCGAATGTAAGGACGTCCGCCTTTTCAGGGCGCAAATCCGCGTTGCCGGCGGTAAAGAACCG

CGTCTGCACAGCCTGTCCGCCATAAATTGAATTGAGCGTCGCCTGACGGCCGGGGTCGAATAGCTCGACAAGGCTTGGCC

CGCGGATATCTCGCGAACGGGTCGCGCGGAACCTGAGGCCGTCGATCGGCTCATATTCTCCGCCCAGCTTCCAGGTTGTT

ACTCCACCGGACTGGCTGTAATCGGCATATCGGACGGCGCCGTTTAAGTTCAGCGAACGTCCCAGCGCGCTGTCCTTCAG

AATCGGGACGCCGATTTCGACAAAACCTTCCTTGATGTCATAGCTTCCCGAGAAGGGAAGTGGGTTGTAGAGATTGAAGC

CTCCAGGCCGACCTGCCTGCGCCGCCGGAGCCCCCCTGATTCCCGTGATCGAGGTCGTCGCCTGCGATATCGCGTCGGTT

TCCTGCCGGGCCTTCTCCTTGCGATATTCGATACCAGCGGCGACCGAGACCGGGCCCGCGCCGAACGACAGGCTATCGCC

GAGGTCGCCGGAAATCGTGAGTCCCGCCACATATTGCTCAAGCCTCAGCTGAGCGACGCCATCAGCGGTGACATAGTCGA

TGGCCGACGCGCTCGGCGAGCCTGTGCCGAAGAGATTGAGCGGCACGCAATCTTGGTCGAGGCCGGCCAGTGTTGAACGG

CAGACGATATTGCCCGCGGGATCGCGGACCGCATCGACGGCGGCGTAGAGATTGCGGTTGATGGTGAGATTGTTTTCACG

AAGCTCGAGGTCCGTAAGGCCAAAGGAGGCCGAGCCATCGAGTTTCCAGCCATTGCCAATGTCTGCCCGGAAGCCGGCAG

CGCCGCGGTAGACCTTTGCGAAATTCTCGATTTCGACCAAGGGAAAGTCGCTTGAGAAGCGACCGACAACGATCGAAGCC

TGGGCATTTCTGTCCATGAGCGTCGCGAGTGGAGCCGGAAGGAAGGCGTTATCACGGAAGATCCGGAAATTATTCGAGCC

ACCGACATGCGATATTACGAATGCACCCAGGTTGGTGTGGGAATAAGCATAGGTGCCCTCCGCATACACCTGCACAGTGT

CGGACACATCATATGCGGCGCGTAGGAACGCGTTGTAGCGAAGCTGATCCGGGGCGAAGCCGATATTCACGCGCGGTCCA

TCGCCGCCGCTCTGGAACGACGAGCTCGTAAAATTCCCGTAGTCGAAGGTCCCTAGGACTCCTCCGGGCAAAAACGCGAT

GCCTTTCAGAGGGCCGGACGTGACAAGTCCGCCGTAGGATCGCGAGAACTGCGAATATCGGGCACGACCGTGACGCCTG

TCGTAGCGCCGGGCACGGGATATTGGCCGGCGGCGATGTCGAACCAGCGGCGACCCGTTGCTTCATCGGCCCGGATTCCG

TCCTGTCGAAAATATTCGAAGCTGCCGAGCAAGTGCAACCGGTCGTCGGCAAACGAAGTGCCGAAGGCGATCGAACCGCC

GTAGGACGGGAGGTCGCCGCGGGTTGAAACACCCGACTGGAGCTCGGCCCTGATGCCTTCCAGATCTTCGTCGAGCACGA

AGTTGATGACGCCCGAAACGGCATCGGAACCGTAGGCGGCCGAGGCGCCGCCCGTCACGACATCGACGCGCTTGACCAAC

GCCTGCGGCAGCACGTTGATATCGACCGAGCCTGTGAAATTGGTCGCGACGAAACGGTTGCCGTTCAGCAGGACGAGGTT
```

-continued

CCGGTTTGACCCGAGGCCGCGCATGTTGAGCAGGTTCTGACCGCTGTTCCCCGTTCCGGGTGTCGTGCCAGGGTTGGAGG
TCTTCAAGCTGTCGTTGAACACGGGCAGCTGGTTGAGTGCGTCGGCAAGGTTGGTCGGAGATGCCTCCTTCAACTGCTCG
CTGGATACGGCTGTAACCGGCGTCGGCGAATTGAAGCCGTTCTGGAGGCGGCTGCCGGTCACGACGATTTCGCTCGTTCC
CCGGTCCGTGTCCGCTTCGTCCGGCTGACCTATCGATGCGGGATCGCTATCCTGAGCACTGGCAGAGACAGGAAATGCGA
GGGTGCCGAGCGCTACTGCGCCGAGCAAACTATTTGCCTTGCCGGGCTTTTCGATTCTGAACTTCCGATACATCTGCAGT
CCCTCCCGAATTGATAGGGACTCCGTTTGAGTCCCCTTGTTTCTTGACGCCGCCGTCGCTCACCACGGTCCGGTCGGAGG
CTAAGCGTCGGGCCTAAGGACCCGCAATTTGAACATCAAATGCAATGATCGGAGGCTTCATTGCACTTCGCGCATAGACC
GGCGCGGTAGCTGAAAGTGCCAATAATCAGGGATTTTGCTGAACAGTTGCGGCATGACGTCCGGCATCGGCCACGCGGTT
GGCGGCATCGACGTGGCTTTCGCGTCGCCGCCCCTCAAGCACCGGCGAGTTGCATTAAAATGGGATGAGGCTGGAGAGAC
GCAAAATCTCTGAGGACCGCGCTGAACGCGCGATCCGTCGCCTCGAGGGTCTCCGTTACATCGTCAACTGTATGGGCCGC
AGAGAGAAACATATTGTGATAGGGATGAACATAGACGCCGCCCTTCAGGCACGCCGCGGCCCACGCATAGCCGATCCGAA
AATCGGGATCGTCCGCAAAGAATATTTGCGGCATCTGCGCCGGGCCCGTCTGCTTCAACTCAAGACCATGGCGCTGAGAC
TGTGCCTCCAGGCCTGCCCGCAGGGCGGCGCCGCTGGCGATCAGCGTTTCGAGATAAGGCGTCTCTCGAATGATCCTGAG
GGTTTCGATCGCGGCCGCCATCGGTACCGCAGAGAACCAGAAGGAGCCGGTCACAAATATATCCCGCGCCGCATCGCGCG
CCTTGTTCGAGCCCAGCAGGGCGGAGATCGGATAGCCATTCGCAAAGCATTTTCCCCAGCAACTGAGATCGGGTTCGATA
CCCAAATGCGTCCAGCTGCAATCGCGCGCCACCCGGAAACCTGCGCGCACATCGTCAACGACCAGAAGCGCACCGGTCTC
GTCACAACATTTTCGAGCGGTGCGCGCGAACTCAAGCTGGGCGAGGGCCTGGTCCTCAAATACTTCGTGTCGGAAAGGTG
TGGCAAAGACAGCCGCAATATCGCCATCGTGCGCCTTGAACGCGTCCGATAAGCTTTGGGCGTCGTTATAGGTATAATAT
GCGACATGCACGCGATCGGAAGCGAGAATCCCGGCAGTATGCGGAGTGTTCCACGGGGAAGCGCCATGATAGGCGCCTTT
GGCGCATAATATGGTTTTGCGCCCCGTATGGGCACGCGCGAGAACCATCGCCGTTGAGGTGGCATCGCTGCCATTTTTGC
AGAACATCGCCCAATCCGCATGACGGACCATGCCCACAAAGGCTTCGGCGAGGTTGACCATGATCTCCGAAGGACCGGTC
ATGGTGTCGCCGAGAAGTCGCTGCGCATCAGCCGCGGCTTCGATTTCGGATTGCCGGTAACCGAGCAAATTTGGCCCATA
CGCGCACATATAGTCGATATAGGGCTGCTCGTCGGCGTCCCAAATTCGTGCCCCAGCGCGCGCCTGAAGAACTGGGGGA
ATTCTGGCGGCAGCAACCGTGTCGACTCGTGGCCGTACATCCCGCCCGGAATGACCCGTTCGGCGCGTTCTCTGAGATCT
TTCTGCCTTGTTCCGTTCGCCATAATGCACCTCTCGCGATAAATAATGGGTAAAAATCCACGAAATTCAACGATTCGTGA
TCTGAAAGAGATATATCTTGTAATATACTGTATAATTATACACAATGCGCAATCGGACGACGGGATAGCGGGGCAGGGAG
GACGGGGAAATCTATGCGGAACGTCAGCGACAAGGCGCCGCCCCACGAGACGCTCACCGTAGTCGTCGCGGCAATGATCG
TTGGCACGGCCGCCTTGATGGTGCTTGGAATACAGCCCATCCTTCTCGGCGCCCTTGTAGAGGAGGGCGTATTCCCGCC
GAGGGGTTGGGATCGGCGGCAACGGTGGAAATACTGGCGATCGCGGCGGGAACATGCATCGGACCCGTTCTTATGAAGAC
GGGATATCTGCGGGCGAAATGCGCGGCACTCTGCTTAATGCTCGCCGCAATCAACTTCGGATTGACGTTGCCGGGTTTCG
ATTTGCCCATCGTGGCTTGCCGAGCGGCAGCGGGAGCCCTGGAAGGTCTTTCGCTCAGCGCGGCGATCCTGATCATGACT
CATAATCGGCGGCCGGACCGGCTGAGCGGAATATTTCTGGGCGCGCAGACGATACCGCAGGTAATATCTGCTTATTTGCT
CCCGACGGAGATTATTCCGCGCTGGGGGAGCGCAGGCGGCTTCACGATCCTGGGCATTCTCGCGGCGATCGCCGCGATCG
CGGCTCTGTGCCTCGTCGATCGCGTTGAGCTCGATCCGACGACCGTTAACGACGACTTGCAGTGGTCACCCGCGGCGATC
GTCATTTCGATGGCGGCATTCGTTCAATTCTCGGGGGTCGGTGCCGCATGGAGCTATCTGGAGCGACTGGCTGCGCAGCA
CGGATTTTCGGGAGAAACGATCGGTATCGCCATTTCCGGGAGTTTGCTTTGCCAGGTAGGCGGGGCTTGGCTGGCCGCTT
GGATCGGTGGGCGGGTCGGATATCGCTTCGCCTTAATCGCTGGGAGCCTGCTTCAGGCGGGCAACGTGATCGCATTGGCG
GTGGCCGATCAGCCAAGCTGGTTTATTTCCGCTTCCTGTGCTTTCGGCCTGTTCTGGTTGGCGATGCAGCCCTTCCAAAT
CCGCTTCGCGATCGCGATAGATAACAGCCGGCAGCTTGCTGTACTGCTGACGCCGATCGCCCTCGTCGGGTTGAGCGCGG
GGCCCTTGTTGCTCTCTCGCTTTGCCGGGGCGACCGACTTGCGCTGGATCTTTGTGGGGAGTTCGACCTTGTTGCTGGCC
AGCGCGCTTCTGTATCTTTGCGCTTCTCTGTTTCAACCGCGCGGAAAGGTGATCGCTGAAACGGTGGACGTATGAAAAAG

-continued

```
ACGGATCGGGGTTCGCGATGACATCGCAGGTCAAGCTTCGTAGCGCGGCAAAGCGGCCGCGCAGTCCTAAAAGCGAGCGA
GGTCTTGCTCGTTACGAGTCCTTGCTTGATGCGACCGACAGGCTGTTGGTCGATCTAGACCCCGATCAGGTCGGTCTCTA
TCAGATTGCAGAGGAAGCGGGTGCCTCACCGTCGTCCGTCTATCATTTCTTTCCGACCAAGGAAGTGGCTCATCTCGCTC
TGATGCGCCGCTATCTGGAGGGGCTCCGGAATCTCGACGCGATGGAAGTCGACATCGGCCAGCTCGAAAGCTGGCAGGAC
CTGATGAAGTTGGATCAGATCAGGGCGCGAGACTATTATAATAGCCACCCGCCCGCCCTCAAGCTTCTGTTCGGCGGATA
TGGCGGGGTCGAGGCCAGAAAGCTTGACGAGCGATACTCCGAGGAAATCGTGAGCTCCATGTATGGCAGATACAACGGCA
TTTTCCATATGCCGCAAATGGAGAATGAGGCTCTCATGTTCACGATCTGCTTCGCAATTCTCGACGCGGTATGGGCCGTC
TCCTTTCGCCGGTTCGGTGAAATTACGTCGGATTTTCTTCGGGAGGGGCAAGCGGCTTGCATTGCCTATTGCCGACACTA
TCTGCCCGAGCGAACGCCATCAGCGTGAATCCGTTCAACGATATGCAGGAATGTCCGTTGCGTTGAGTTCGGTTCTGAGT
TCGGTCGGTTAGGAGGCCCCGCGATAAACCAACGCTCTTCTGTCGAAGGGATGTCGCCTGGTTCGACCAGGCCCTGCGAA
GTCAGCCGCAATCAACGAGGCAGATGTCAACGTGGCCAGCAAGTTCAACTGTGAGTTACTCGATCTGCGATCATTTGTTG
CGGTGTATGAAACGCGAAGTTTTAGCCACGCCGCGCGGCTTCTGAATCAATCGCAGCCCGCGCTCAGCCGGAGAATCCAG
CGCCTCGAGAGTCTCGTGGGCGGTCCGTTGTTCGAGCGGACCAGTCGGTCGCTTGCCGAAACGGCGCTCGGCAAAGAGTT
GCTCCCGGTCGCCCACCGAGCGTTGGAACTTGTCGATACGTCGCTGTTTGCGTCGCCCAATGTCCGGGAGTTCCGCTGGA
CAGACATCACGATTGCCTGTGTACAGACCGCCGCCTTCCATGTTCTCCCGCGAGCTGCGCGCTTGTACATGGATCAAAAT
CCGAGGGTCCGACTCCGCATCCTTGACGTGCCGGCGGTCGAGGCTGCGGACCTGGTTGCGAGCGGCGAGGCGGAGTTCGG
CATCAGCATTGAGAGCCTGTTGCCATCAAGCCTGCGGTTCGATGCGCTCCACGAGGACCCGTTCGGCCTGGCATGCCACC
GAAGCCATCCGCTGGCGTCGCTCGAGATCCTTGAATGGACGCAATTGAAAGGTGAAAGCCTGATCGCCGTTCACCGTGCG
AGCCGGAACCGCACGTTGCTCGATGCCGAACTCGCGCGCAACAATATCGCGCTGGAATGGCGGTATGAGGTCGCGCATCT
GACGACGGCGCTGGGATTGATCGATGCGCAATTGGGTGTCGCTGTTATGCCCCGCATGGTTATGCCCCGCTCGGGTCGGT
CGGAGGTCGTCTGGCGCCCCGTCGTCGCGCCGGTCGTCCAACGCACGATCGGCATCGTTCAGCGCCGCACCGGCTCGATG
CACCCTGCCGCACAGCAATTGCTTGCGCGGCTCCGCGCGGCCTGGTCGTCCGCCAATCTGGGCGACATCGCGTCTCGCGA
AGATGGGGCATCGTGACACGCGTTCTATGCGCCTGCAGCATCGATGCTCACGATCATTGCATTTGCTGAGAGACGAACGC
GAAGATACCGCTGGGTCACAGGATATCAGTCCATCGAGGCGGGAGAGAAATGTGTGAAAGAGCACCAATGCCGTGGCGGC
CGGGCGTCCCCCGCTGCGCCCGCCACGTGGCTTGCGCGGATCAGCGTTTCCCGGGGGGCCTCCGCCATCGCCTGGACCTT
CATGCTTGGCGCAACTGCCATTCCCGTGGCTGCGCAAACTGACGATCCGAAGCTCGTTCGTCATACCCAGTCGGGCGCCG
TCGAGGGCGTCGAGGGCGACGTCGAGACTTTTTTGGGAATACCCTTCGCGGCTCCGCCGGTCGGCGACCTGCGATGGCGG
CCGCCGGCTCCGCCGAGGGCGTGGGCGGGCACCAGGGACGGCCGCCGCTTTGCGCCCGATTGCATCGGGAACGAGCGGCT
TAGAGAGGGGAGCCGGGCTGCCGGGACGAGCGAAGACTGCCTCTATCTGAATATCTGGTCTCCCAAACAGGTCGGTAAGG
GGGGGCTCCCCGTCATGATCTGGGTTTACGGCGGTGGGTTTAGCGGCGGTTCTGGCGCGGTGCCATATTATGACGGCTCT
GCGCTCGCGCAGAAGGGCGTGGTGGTCGTCACGTTCAACTATCGCGCCGGGATTCTGGGCTTTCTTGCCCATCCGGCGCT
TTCAAAGGAAAGTCCGAATGGCGTGTCGGGCAACTATGGTCTTCTCGACATGCTCGCGGCGTTCAAATGGGTTCAGAACA
ACATAAGGGAGTTCGGCGGAGACCCGAACCGTGTCACGGTCTTTGGCGAGTCCGCCGGCGCGAGCGCGCTCGGACTGCTC
CTGACCTCGCCGCTCAGTGAGAGCGCCTTCAATCAGGCGATACTGCAAAGTCCGGGTCTGGCCAGGCCGCTCGCCACGCT
TTCTGAAAGCGAAGCGAATGGGCTGGAGCTGGGAGCCGATATTTCTGCTCTACGGCGTGCCGATGCGGGCGAATTGACGA
AGATCGCGCAATCGCGAATACCCATGTCGCGCCAGTTCACCAAGCCGCGGCCGATGGGTCCGATTCTGGACGGCTATGTT
TTGCGCACCCTTGACGTCGATGCCTTCGCCAAGGGGGCCTTCCGCAAGATACCCGTTCTGGTCGGCGGAAACGCCGACGA
AGGGCGCGCTTTTACGGATCGCCTGCCGGTCAAAACGGTCCTTGAATATCGAGCCTATCTCACAGAACAATTTGGTGACG
AGGCGGACGCATGGGAGCGTTGTTATCCCGCGAACTCCGACGCCGACGTCCCCGCCGCCGTTGCCCGTCTTTTTGGGGAT
AGTCAGTTCAACAACGGGATCGAGCTGCTCTCGGCAGCCTTCGCGAAATGGCGAACGCCGCTTTGGAGATATCGCTTTAC
```

-continued

```
GGGCATTCCAGGAGCCGGCCGTCGCCCCGCCACGCATGGAGACGAAATTCCCTATGTCTTCGCAAATCTGGGGCCGTCGT
CCGTATCTATGTTTGGGTCGCTCGAAGGCGGCGCCGGGGCGTCGGACATCAAACTTGCGACCGAAATGTCCGCGGCCTGG
GTGAGCTTCGCGGTGCACGGGGTCCCCGATCAGGGCACGAAATCGCACTGGCCGCGCTTCGAGCGGCGAGGGGAGATCAT
GACTTTTGGTTCGCAGGTTGGCTCTGGGGAAGGTCTTGGAGTTTCGCCGAGCAAAGCCTGCCAACCCTCAAAATAGCGCC
CGGCCTGTGCGTGCTTCAGCACGCCGTCCCGCTTTGCGGGCGACGGGCTGTGCCCTCTGCCTAGAAGGAAGTAAGTTGCG
CTACGACGTCGCGATAATTGGAGGTGGCAACGCTGCATTGACGGCAGCCGTGACGGCGCGTGAAGCGGGGGCCTCGGTTC
TTGTGATCGAGCATGCGCCGCGCGCCATGCGCGGCGGCAACAGTCGTCACACACGCAATATGCGTACGATGCACGAACGT
CCCCTGTCGCCGTTGACCGGTGAATATTCGGCGGACGAATATTGGAATGATCTTGTCCGCGTCACGGGGGGGCGCACCGA
CGAAGAACTCGCGCGGCTCGTTATCCGCAACACCACCGACGCTATTCCCTTCATGACGCGCTGCGGTGTGCGTTTCCAGC
CCTCGCTGTCGGGCACGCTGAGTTTATCGCGAACCAACGCATTCTTCCTTGGCGGCGGGAAGGCGCTTGTAAACGCATAT
TACGCCACGGCCGAACGGCTAGGCGTCGATATTCTCTATGATTCTGAGGTGACCGAGATCAACCTTCAGCAAGGCGTCGT
GCAGCGTCTGCAATTGCGCAGCCGGGGATTCCCTGTCGAAGTGGAAGCCAAGGCTGCCATCGCCTCGTCCGGAGGATTCC
AGGCAAATCTTGACTGGCTCTCAAGCGCATGGGGCCTGCTGCGGCGAACTTCATCGTACGGGGCACGCCATATGCGACT
GGCACGGTGCTCAAGAACCTGTTGGAGCAAGGCGTCGCCTCGGTGGGAGATCCAACCCAATGCCATGCTGTCGCGATCGA
TGGGCGAGCGCCCAAATACGACGGCGGCATCGTCACACGACTGGACTGCGTTCCCTTCTCGATCGTCGTCAACAAGGACG
CCTTGCGCTTCTACGATGAAGGCGAAGATGTGTGGCCGAAGCGTTACGCCATATGGGGTCGCTTGGTGGCACAGCAGCCT
GATCAGATCGCTTTCAGCATAATCGATCGGCAGGCCGAAGACCTCTTCATGCCGTCAGTGTTCCCCCCCGTGCAAGCGGA
CACGATCGCGGGTCTGGCCGAGAAACTCGGTCTGAATCCCGTAACCCTGGAACGCACGGTGGCCGAATTCAACGCCGCAT
GCGTGCCCGGCGAATTCGGCGCCAAGATCTCGACGACCTCCACACCGAGGGAATCGAACCAAAGAAATCCAACTGGGCC
CGACCGATTATTGTGCCCCCGTTCAGCGCCTATCCTCTCCGGCCCGGGATCACCTTCACCTATCTCGGCGTCAAGGTAGA
CAGCCGTGCGCGGGTCATCATGGAGACAGGTGAGCCGACAAAAAACCTGTTTGCTTCGGGGGAAATAATGGCGGCAGCA
TTCTCGGCCAAGGTTATCTCGCTGGATTTGGAATGGCGATTGGTACCGTATTCGGCCGCATCGCGGGTTGGGAGGCCGCA
CGTCATGCAGGATTTTGATCTCGTAAAAATGCTGTCTGACTTGCCGTCGGCGCCGGAGCTGGAAGCCAGGCGCGTTATGG
AGGTGTGCAACGCGTGCCGCTATTGCGAAGGGTTCTGCGCGGTATTTCCTGCAATGACCTTGCAGCGTCATTTCGCCAGC
GGCGATCTCAGCCACCTCGCCAATCTCTGCCACTCGTGCCAAGGTTGCTATTACGCCTGCCAATACGCCCCTCCGCATGA
GTTCGGAATAAACGTTCCAAAGGCGCTGTCGGAGTTGCGGCTCGAGAGCTACGAGCAGCATGCTTGGCCCCGGCCGGTCG
CCGCTCTCTATCGCAAGAATGCGCTCATCATTTCCATCTTGTCGGCGGCATGCATAACCGGCGTCCTTCTGCTTGCCGCC
ATCTTCAACGGGGATGCACTTTTCGCGAAACACGCATCGGTGCCCGGCGGCGGGTTTTACAACGTTATTCCTTATCAGGC
GATGATTGCCGTCGCGGCGACCACATTTCTTTATTCCGCGCTGGCGCTGGCGATCAGTCTCGTTCGCTTTTCGCGGACGA
TCGGTCTGGGAATTAAGGTTCTTTATCAGCACGTGCCGGTTCTTCGGGCGCTACGCGATGCGGCGACTCTGCGATATCTC
GGCGGCAGCGACGGCGAGGGGTGTAACGACGCGGACGAGACATTTTCGACGACCCGGCGAAAATTTCATCACGCCCTTGC
CTATGGCTTCGGACTTTGTTTCGCGGCCACAGCCACGGGCACGATCTACGATCATATGTTCGGCTGGCCGGCGCCCTATG
CGCTTTTCAGCTTGCCGGTCGTCCTAGGGACCGTTGGGGGGATCGGAATGGTCGTGGGCGCGATCGGCCTACTCTGGCTC
AAGCTGGCCGGCGAAGACGCTCCTCGATCACCGGCACTGCTTGGGCCGGATGTTGCCCTGTTGGTGCTTCTGCTTGCCAT
AGCGGCAACGGGCCTCCTCCTTTTAGCGGTCCGCAGCACCGAAGTCATGGGCGTCGCGCTCGCCGTCCATCTCGGCGTCG
TCTTGGCCTTCTTTTTGGTGATGCCATACAGCAAATTTGTCCACGGTATCTTCAGGCTCACGGCTCTCGTGCGCCATCAT
GCTGACCGCGAGGCAAGTAATGGCTTCGCCTCCAGCCCTCCCACGAAAAAGGGTTAAACAATGGAACATATGAAGTCCGT
TCGCGATCGCAGTAGCGTCATGCAGATCGTGAGAGTGGCGAGTGGCAACTGTCTCGAGCAATATGATTTCTTCGTTTACG
GCTTCTATGCGGCATATATTGCGAGAAGCTTTTTTCCGACCGGCGATAACGCGACATCGCTCATGCTTTCATTGGCCACT
TTTGGCGCTGGTTTCCTCATGAGGCCCTTGGGGGCGATTTTTCTCGGGTCCTACATCGATCGCGTCGGGCGTCGGAAAGG
CCTGATCGTGACACTCGCGATCATGGCCGTCGGAACCCTCACCATTGCGATGACTCCAAGCTATGAGGCAATTGGATTAC
```

-continued

```
TCGCACCGGTTATCGTGCTCGTCGGGCGACTTTTGCAGGGTTTTTCCGCTGGAGCAGAGTCGGGTGGCGTCTCAGTGTAC
TTGGCGGAAATTGCGTCGCCCAAATCGAGAGGCTTCTTCACCTCGTGGCAGTCTGCCAGCCAGCAGGTGGCCGTCATGAT
CGCCGCCGCGATCGGTCTTGCGCTGCAATCAACGCTTTCACCGGAGCAAATGAACGACTGGGGATGGCGGGTGCCCTTGT
TGATCGGATGCTTGATTATCCCCGTGATACTCTGGCTGCGCCGGTCTCTCCCGGAAACGAAAGCCTATCTCCACATGGAG
CACAAGGCGCATTCGATCGGCGAATCCCTCCGCGAATTGCAACAGAGCTGGGGGCTGATCTTGACGGGCATGGCGATGTC
GATCCTCACGACGACCACCTTTTACATGATTACCGCCTATACGCCGACATTTGGCGAGAAAGCACTCGGACTGAGCCCGC
AAGATGTCCTGCTGGTTACCATCATGGTCGGCGTGTCGAACTTCCTGTGGCTTCCGATCGGGGTGCTCTCTCGGATCGT
ATCGGTAGAACCCCGATCCTACTGGTCGTGCCGGTCACCGTTCTCGCCATCGCCTTTCCCCTGATGAGCTGGCTCGTCGC
GGCACCGACATTCGGAGCGCTTGCAGCTGTTCTGCTGACTTTCTCCGCATGCTTTGGACTCTATAATGGGGCGCTCATCG
CGAGACTCACCGAGATTATGCCTCCCGCCATTAGAACCCTTGGCTTCTCGCTGGCGTTCAGTCTCGCGACCTCGCTGTTC
GGCGGCTTCACCCCATTGGTAAGTACGGCGCTAATCCACGCGACGGGCAGCAATTCCGCGCCTGCAATCTGGCTCTGTTT
TGCGGCTTTCATCAGCTTCGTCGGTGTGGCCGCATCGACCCGGCTGAGCCGGCCAATCGCCGAAGGCGCCAGATAGGACA
ATCAGAGAATGCCCGTGCGGCAATGAAGCGAGATTCGGGCGGTAGGTGCGCTGGCGGCACTTCGCGAAGAGCCGTTGCGG
ACGGCTGAAACGATGATGGTATGAATGGGCTAAGACATGAGAGCAGTAGTTTACCGAAATGGCGAACTTGTCCTGGGGGC
CTATGCTGATCCGATACCCGCCGCCGGGCAGGTGCTCGTCAAGACCAGAGCATGCGGCATCTGCGGATCTGACCTTCATT
TTTGCGATCATGCGCAGGCGTTTACGAACCTTGCATCGCGGGCGGGTATCGCCTCTATGGAAGTTGATTTGTGTCGAGAC
ATCGTTCTGGGGCATGAATTCTGTGGCGAGATTATGGAGTTCGGGCCCTCTGCGGATCGTCGCTTCAAACCCGGACAGCT
TGTGTGCTCGCTGCCGCTGGCGATCGGTCCGACCGGAGCGCGGACGATTGGCTACTCGGATGAGTATCCGGCGGGCTCG
GCGAATATATGGTCCTCACGGAAGCGCTCTTGCTGCCTGTTCCGAACGGCCTTCCGGCGACCTGCGCGGCGTTGACGGAG
CCGATGGCGGTGGGATGGCATGCCGTCGAGATCGCGCAGGTTCAACCACATCACATCCCTGTGGTGATCGGGTGCGGACC
GGTCGGGTTGGCAGTCGTCGCTGCCCTGAAACATAAGCAAGTTGCTCCGATTATTGCGTCGGATCCATCGCCCGATCGGC
GTGCTCTTGCTCTGCGGATGGGCGCCGACGCCGTTGTCGATCCGCGCGAAGAATCACCCTTTCGCCAGGCCGAGAAGATC
GCACGCCCGGTCGGACAAGGTGGGGCCCTGTCCAGCTCATTGCTGTCAAAGTCTCAAATGATATTCGAATGCGTAGGGGT
GCCGGGCATGCTTCGGCATGCGATGGACGGCGCGTCCGACGGGTCCGAGATCATGGTCGTTGGCGCATGCATGCAGCCGG
ACGCGATCGAGCCCATGATCGGGATGTTTAAAGCGCTCACGATCAAATTCTCGCGAACTTACACGGGTGAGGAATTCGCC
GCGGTGCTTCACATGATAGGTGAGGGCGCACTCGACGTATCTCCGCTCGTTACCGATGTGATTGGCCTGTCCGATGTCCC
GTCCGCGTTTGAGGCTCTACGGAGTCCAGGCGCCCAAGCAAAAGTGATTGTGGACCCTTGGCGCTGAGCCTGAGGATGCC
AAGGGTGCGACGTTGGGCATCGTCAAAGAAGGCGACGTTGACCCGGTATGTGAACATCCCCATATTCTTCCGCAGCTGAA
GCAGTTGGTAAACATGCCAAAATATGAACTGTAGTATTGCGTCGGGGTTCTCATTGTGGGGTTTGCCATTGTCATCGCTC
GCACCCGGCGACAAAGATTAGATGTACTTCCGATAATCCGTGCTCTCGACCTGGCCTTCCTTCATATATTTCAGGACCTC
TCCGACCATGCGTGCGGCGCGATCGGATCGGCAGGCGTTGTTCATCTGGGTCGAGTTCCAGTTGATCTTCGTAAGAG
AGAACACCTCCTCGGCTAACTGCGCCGCGGTACTATCGCAGGATCGTCTCGAGCGTYCGC

>Seq ID 2 (fumA)
ATGCGGAACGTCAGCGACAAGGCGCCGCCCCACGAGACGCTCACCGTAGTCGTCGCGGCAATGATCGTTGGCACGGCCGC
CTTGATGGTGCTTGGAATACAGCCCATCCTTCTCGGCGCCCTTGTAGAGGAGGGGCGTATTCCCGCCGAGGGGTTGGGAT
CGGCGGCAACGGTGGAAATACTGGCGATCGCGGCGGGAACATGCATCGGACCCGTTCTTATGAAGACGGGATATCTGCGG
GCGAAATGCGCGGCACTCTGCTTAATGCTCGCCGCAATCAACTTCGGATTGACGTTGCCGGGTTTCGATTTGCCCATCGT
GGCTTGCCGAGCGGCAGCGGGAGCCCTGGAAGGTCTTTCGCTCAGCGCGGCGATCCTGATCATGACTCATAATCGGCGGC
CGGACCGGCTGAGCGGAATATTTCTGGGCGCGCAGACGATACCGCAGGTAATATCTGCTTATTTGCTCCCGACGGAGATT
ATTCCGCGCTGGGGGAGCGCAGGCGGCTTCACGATCCTGGGCATTCTCGCGGCGATCGCCGCGATCGCGGCTCTGTGCCT
CGTCGATCGCGTTGAGCTCGATCCGACGACCGTTAACGACGACTTGCAGTGGTCACCCGCGGCGATCGTCATTTCGATGG
```

-continued

CGGCATTCGTTCAATTCTCGGGGGTCGGTGCCGCATGGAGCTATCTGGAGCGACTGGCTGCGCAGCACGGATTTTCGGGA

GAAACGATCGGTATCGCCATTTCCGGGAGTTTGCTTTGCCAGGTAGGCGGGCTTGGCTGGCCGCTTGGATCGGTGGGCG

GGTCGGATATCGCTTCGCCTTAATCGCTGGGAGCCTGCTTCAGGCGGGCAACGTGATCGCATTGGCGGTGGCCGATCAGC

CAAGCTGGTTTATTTCCGCTTCCTGTGCTTTCGGCCTGTTCTGGTTGGCGATGCAGCCCTTCCAAATCCGCTTCGCGATC

GCGATAGATAACAGCCGGCAGCTTGCTGTACTGCTGACGCCGATCGCCCTCGTCGGGTTGAGCGCGGGGCCCTTGTTGCT

CTCTCGCTTTGCCGGGGCGACCGACTTGCGCTGGATCTTTGTGGGGAGTTCGACCTTGTTGCTGGCCAGCGCGCTTCTGT

ATCTTTGCGCTTCTCTGTTTCAACCGCGCGGAAAGGTGATCGCTGAAACGGTGGACGTA

>Seq ID 4 (fumB)
ATGACATCGCAGGTCAAGCTTCGTAGCGCGGCAAAGCGGCCGCGCAGTCCTAAAAGCGAGCGAGGTCTTGCTCGTTACGA

GTCCTTGCTTGATGCGACCGACAGGCTGTTGGTCGATCTAGACCCCGATCAGGTCGGTCTCTATCAGATTGCAGAGGAAG

CGGGTGCCTCACCGTCGTCCGTCTATCATTTCTTTCCGACCAAGGAAGTGGCTCATCTCGCTCTGATGCGCCGCTATCTG

GAGGGGCTCCGGAATCTCGACGCGATGGAAGTCGACATCGGCCAGCTCGAAAGCTGGCAGGACCTGATGAAGTTGGATCA

GATCAGGGCGCGAGACTATTATAATAGCCACCCGCCCGCCCTCAAGCTTCTGTTCGGCGGATATGGCGGGGTCGAGGCCA

GAAAGCTTGACGAGCGATACTCCGAGGAAATCGTGAGCTCCATGTATGGCAGATACAACGGCATTTTCCATATGCCGCAA

ATGGAGAATGAGGCTCTCATGTTCACGATCTGCTTCGCAATTCTCGACGCGGTATGGGCCGTCTCCTTTCGCCGGTTCGG

TGAAATTACGTCGGATTTTCTTCGGGAGGGGCAAGCGGCTTGCATTGCCTATTGCCGACACTATCTGCCCGAGCGAACGC

CATCAGCGTGA

>Seq ID 6 (fumC)
GTGGCCAGCAAGTTCAACTGTGAGTTACTCGATCTGCGATCATTTGTTGCGGTGTATGAAACGCGAAGTTTTAGCCACGC

CGCGCGGCTTCTGAATCAATCGCAGCCCGCGCTCAGCCGGAGAATCCAGCGCCTCGAGAGTCTCGTGGGCGGTCCGTTGT

TCGAGCGGACCAGTCGGTCGCTTGCCGAAACGGCGCTCGGCAAAGAGTTGCTCCCGGTCGCCCACCGAGCGTTGGAACTT

GTCGATACGTCGCTGTTTGCGTCGCCCAATGTCCGGGAGTTCCGCTGGACAGACATCACGATTGCCTGTGTACAGACCGC

CGCCTTCCATGTTCTCCCGCGAGCTGCGCGCTTGTACATGGATCAAAATCCGAGGGTCCGACTCCGCATCCTTGACGTGC

CGGCGGTCGAGGCTGCGGACCTGGTTGCGAGCGGCGAGGCGGAGTTCGGCATCAGCATTGAGAGCCTGTTGCCATCAAGC

CTGCGGTTCGATGCGCTCCACGAGGACCCGTTCGGCCTGGCATGCCACCGAAGCCATCCGCTGGCGTCGCTCGAGATCCT

TGAATGGACGCAATTGAAAGGTGAAAGCCTGATCGCCGTTCACCGTGCGAGCCGGAACCGCACGTTGCTCGATGCCGAAC

TCGCGCGCAACAATATCGCGCTGGAATGGCGGTATGAGGTCGCGCATCTGACGACGGCGCTGGGATTGATCGATGCGCAA

TTGGGTGTCGCTGTTATGCCCCGCATGGTTATGCCCCGCTCGGGTCGGTCGGAGGTCGTCTGGCGCCCCGTCGTCGCGCC

GGTCGTCCAACGCACGATCGGCATCGTTCAGCGCCGCACCGGCTCGATGCACCCTGCCGCACAGCAATTGCTTGCGCGGC

TCCGCGCGGCCTGGTCGTCCGCCAATCTGGGCGACATCGCGTCTCGCGAAGATGGGGCATCGTGA

>Seq ID 8 (fumD)
GTGAAAGAGCACCAATGCCGTGGCGGCCGGGCGTCCCCCGCTGCGCCCGCCACGTGGCTTGCGCGGATCAGCGTTTCCCG

GGGGGCCTCCGCCATCGCCTGGACCTTCATGCTTGGCGCAACTGCCATTCCCGTGGCTGCGCAAACTGACGATCCGAAGC

TCGTTCGTCATACCCAGTCGGGCGCCGTCGAGGGCGTCGAGGGCGACGTCGAGACTTTTTTGGGAATACCCTTCGCGGCT

CCGCCGGTCGGCGACCTGCGATGGCGGCCGCCGGCTCCGCCGAGGGCGTGGGCGGGCACCAGGGACGGCCGCCGCTTTGC

GCCCGATTGCATCGGGAACGAGCGGCTTAGAGAGGGGAGCCGGGCTGCCGGGACGAGCGAAGACTGCCTCTATCTGAATA

TCTGGTCTCCCAAACAGGTCGGTAAGGGGGGGCTCCCCGTCATGATCTGGGTTTACGGCGGTGGGTTTAGCGGCGGTTCT

GGCGCGGTGCCATATTATGACGGCTCTGCGCTCGCGCAGAAGGGCGTGGTGGTCGTCACGTTCAACTATCGCGCCGGGAT

TCTGGGCTTTCTTGCCCATCCGGCGCTTTCAAAGGAAAGTCCGAATGGCGTGTCGGGCAACTATGGTCTTCTCGACATGC

TCGCGGCGTTCAAATGGGTTCAGAACAACATAAGGGAGTTCGGCGGAGACCCGAACCGTGTCACGGTCTTTGGCGAGTCC

GCCGGCGCGAGCGCGCTCGGACTGCTCCTGACCTCGCCGCTCAGTGAGAGCGCCTTCAATCAGGCGATACTGCAAAGTCC

GGGTCTGGCCAGGCCGCTCGCCACGCTTTCTGAAAGCGAAGCGAATGGGCTGGAGCTGGGAGCCGATATTTCTGCTCTAC

-continued

GGCGTGCCGATGCGGGCGAATTGACGAAGATCGCGCAATCGCGAATACCCATGTCGCGCCAGTTCACCAAGCCGCGGCCG

ATGGGTCCGATTCTGGACGGCTATGTTTTGCGCACCCTTGACGTCGATGCCTTCGCCAAGGGGGCCTTCCGCAAGATACC

CGTTCTGGTCGGCGGAAACGCCGACGAAGGGCGCGCTTTTACGGATCGCCTGCCGGTCAAAACGGTCCTTGAATATCGAG

CCTATCTCACAGAACAATTTGGTGACGAGGCGGACGCATGGGAGCGTTGTTATCCCGCGAACTCCGACGCCGACGTCCCC

GCCGCCGTTGCCCGTCTTTTTGGGGATAGTCAGTTCAACAACGGGATCGAGCTGCTCTCGGCAGCCTTCGCGAAATGGCG

AACGCCGCTTTGGAGATATCGCTTTACGGGCATTCCAGGAGCCGGCCGTCGCCCCGCCACGCATGGAGACGAAATTCCCT

ATGTCTTCGCAAATCTGGGGCCGTCGTCCGTATCTATGTTTGGGTCGCTCGAAGGCGGCGCCGGGGCGTCGGACATCAAA

CTTGCGACCGAAATGTCCGCGGCCTGGGTGAGCTTCGCGGTGCACGGGGTCCCCGATCAGGGCACGAAATCGCACTGGCC

GCGCTTCGAGCGGCGAGGGGAGATCATGACTTTTGGTTCGCAGGTTGGCTCTGGGGAAGGTCTTGGAGTTTCGCCGAGCA

AAGCCTGCCAACCCTCAAAATAG

>Seq ID 10 (fumE)
TTGGAGTTTCGCCGAGCAAAGCCTGCCAACCCTCAAAATAGCGCCCGGCCTGTGCGTGCTTCAGCACGCCGTCCCGCTTT

GCGGGCGACGGGCTGTGCCCTCTGCCTAGAAGGAAGTAAGTTGCGCTACGACGTCGCGATAATTGGAGGTGGCAACGCTG

CATTGACGGCAGCCGTGACGGCGCGTGAAGCGGGGGCCTCGGTTCTTGTGATCGAGCATGCGCCGCGCGCCATGCGCGGC

GGCAACAGTCGTCACACACGCAATATGCGTACGATGCACGAACGTCCCCTGTCGCCGTTGACCGGTGAATATTCGGCGGA

CGAATATTGGAATGATCTTGTCCGCGTCACGGGGGGCGCACCGACGAAGAACTCGCGCGGCTCGTTATCCGCAACACCA

CCGACGCTATTCCCTTCATGACGCGCTGCGGTGTGCGTTTCCAGCCCTCGCTGTCGGGCACGCTGAGTTTATCGCGAACC

AACGCATTCTTCCTTGGCGGCGGGAAGGCGCTTGTAAACGCATATTACGCCACGGCCGAACGGCTAGGCGTCGATATTCT

CTATGATTCTGAGGTGACCGAGATCAACCTTCAGCAAGGCGTCGTGCAGCGTCTGCAATTGCGCAGCCGGGGATTCCCTG

TCGAAGTGGAAGCCAAGGCTGCCATCGCCTCGTCCGGAGGATTCCAGGCAAATCTTGACTGGCTCTCAAGCGCATGGGGG

CCTGCTGCGGCGAACTTCATCGTACGGGGCACGCCATATGCGACTGGCACGGTGCTCAAGAACCTGTTGGAGCAAGGCGT

CGCCTCGGTGGGAGATCCAACCCAATGCCATGCTGTCGCGATCGATGGGCGAGCGCCCAAATACGACGGCGGCATCGTCA

CACGACTGGACTGCGTTCCCTTCTCGATCGTCGTCAACAAGGACGCCTTGCGCTTCTACGATGAAGGCGAAGATGTGTGG

CCGAAGCGTTACGCCATATGGGGTCGCTTGGTGGCACAGCAGCCTGATCAGATCGCTTTCAGCATAATCGATCGGCAGGC

CGAAGACCTCTTCATGCCGTCAGTGTTCCCCCCCGTGCAAGCGGACACGATCGCGGGTCTGGCCGAGAAACTCGGTCTGA

ATCCCGTAACCCTGGAACGCACGGTGGCCGAATTCAACGCCGCATGCGTGCCCGGCGAATTCGGCGGCCAAGATCTCGAC

GACCTCCACACCGAGGGAATCGAACCAAAGAAATCCAACTGGGCCCGACCGATTATTGTGCCCCCGTTCAGCGCCTATCC

TCTCCGGCCCGGGATCACCTTCACCTATCTCGGCGTCAAGGTAGACAGCCGTGCGCGGGTCATCATGGAGACAGGTGAGC

CGACAAAAAACCTGTTTGCTTCGGGGGAAATAATGGCGGGCAGCATTCTCGGCCAAGGTTATCTCGCTGGATTTGGAATG

GCGATTGGTACCGTATTCGGCCGCATCGCGGGTTGGGAGGCCGCACGTCATGCAGGATTTTGA

>Seq ID 12 (fumF)
ATGCAGGATTTTGATCTCGTAAAAATGCTGTCTGACTTGCCGTCGGCGCCGGAGCTGGAAGCCAGGCGCGTTATGGAGGT

GTGCAACGCGTGCCGCTATTGCGAAGGGTTCTGCGCGGTATTTCCTGCAATGACCTTGCAGCGTCATTTCGCCAGCGGCG

ATCTCAGCCACCTCGCCAATCTCTGCCACTCGTGCCAAGGTTGCTATTACGCCTGCCAATACGCCCCTCCGCATGAGTTC

GGAATAAACGTTCCAAAGGCGCTGTCGGAGTTGCGGCTCGAGAGCTACGAGCAGCATGCTTGGCCCCGGCCGGTCGCCGC

TCTCTATCGCAAGAATGCGCTCATCATTTCCATCTTGTCGGCGGCATGCATAACCGGCGTCCTTCTGCTTGCCGCCATCT

TCAACGGGGATGCACTTTTCGCGAAACACGCATCGGTGCCCGGCGGCGGGTTTTACAACGTTATTCCTTATCAGGCGATG

ATTGCCGTCGCGGCGACCACATTTCTTTATTCCGCGCTGGCGCTGGCGATCAGTCTCGTTCGCTTTTCGCGGACGATCGG

TCTGGGAATTAAGGTTCTTTATCAGCACGTGCCGGTTCTTCGGGCGCTACGCGATGCGGCGACTCTGCGATATCTCGGCG

GCAGCGACGGCGAGGGGTGTAACGACGCGGACGAGACATTTTCGACGACCCGGCGAAAATTTCATCACGCCCTTGCCTAT

GGCTTCGGACTTTGTTTCGCGGCCACAGCCACGGGCACGATCTACGATCATATGTTCGGCTGGCCGGCGCCCTATGCGCT

-continued
```
TTTCAGCTTGCCGGTCGTCCTAGGGACCGTTGGGGGGATCGGAATGGTCGTGGGCGCGATCGGCCTACTCTGGCTCAAGC

TGGCCGGCGAAGACGCTCCTCGATCACCGGCACTGCTTGGGCCGGATGTTGCCCTGTTGGTGCTTCTGCTTGCCATAGCG

GCAACGGGCCTCCTCCTTTTAGCGGTCCGCAGCACCGAAGTCATGGGCGTCGCGCTCGCCGTCCATCTCGGCGTCGTCTT

GGCCTTCTTTTTGGTGATGCCATACAGCAAATTTGTCCACGGTATCTTCAGGCTCACGGCTCTCGTGCGCCATCATGCTG

ACCGCGAGGCAAGTAATGGCTTCGCCTCCAGCCCTCCCACGAAAAAGGGTTAA

>Seq ID 14 (fumG)
ATGGAACATATGAAGTCCGTTCGCGATCGCAGTAGCGTCATGCAGATCGTGAGAGTGGCGAGTGGCAACTGTCTCGAGCA

ATATGATTTCTTCGTTTACGGCTTCTATGCGGCATATATTGCGAGAAGCTTTTTTCCGACCGGCGATAACGCGACATCGC

TCATGCTTTCATTGGCCACTTTTGGCGCTGGTTTCCTCATGAGGCCCTTGGGGGCGATTTTTCTCGGGTCCTACATCGAT

CGCGTCGGGCGTCGGAAAGGCCTGATCGTGACACTCGCGATCATGGCCGTCGGAACCCTCACCATTGCGATGACTCCAAG

CTATGAGGCAATTGGATTACTCGCACCGGTTATCGTGCTCGTCGGGCGACTTTTGCAGGGTTTTTCCGCTGGAGCAGAGT

CGGGTGGCGTCTCAGTGTACTTGGCGGAAATTGCGTCGCCCAAATCGAGAGGCTTCTTCACCTCGTGGCAGTCTGCCAGC

CAGCAGGTGGCCGTCATGATCGCCGCCGCGATCGGTCTTGCGCTGCAATCAACGCTTTCACCGGAGCAAATGAACGACTG

GGGATGGCGGGTGCCCTTGTTGATCGGATGCTTGATTATCCCCGTGATACTCTGGCTGCGCCGGTCTCTCCCGGAAACGA

AAGCCTATCTCCACATGGAGCACAAGGCGCATTCGATCGGCGAATCCCTCCGCGAATTGCAACAGAGCTGGGGGCTGATC

TTGACGGGCATGGCGATGTCGATCCTCACGACGACCACCTTTTACATGATTACCGCCTATACGCCGACATTTGGCGAGAA

AGCACTCGGACTGAGCCCGCAAGATGTCCTGCTGGTTACCATCATGGTCGGCGTGTCGAACTTCCTGTGGCTTCCGATCG

GGGGTGCTCTCTCGGATCGTATCGGTAGAACCCCGATCCTACTGGTCGTGCCGGTCACCGTTCTCGCCATCGCCTTTCCC

CTGATGAGCTGGCTCGTCGCGGCACCGACATTCGGAGCGCTTGCAGCTGTTCTGCTGACTTTCTCCGCATGCTTTGGACT

CTATAATGGGGCGCTCATCGCGAGACTCACCGAGATTATGCCTCCCGCCATTAGAACCCTTGGCTTCTCGCTGGCGTTCA

GTCTCGCGACCTCGCTGTTCGGCGGCTTCACCCCATTGGTAAGTACGGCGCTAATCCACGCGACGGGCAGCAATTCCGCG

CCTGCAATCTGGCTCTGTTTTGCGGCTTTCATCAGCTTCGTCGGTGTGGCCGCATCGACCCGGCTGAGCCGGCCAATCGC

CGAAGGCGCCAGATAG

>Seq ID 16 (fumH)
ATGAGAGCAGTAGTTTACCGAAATGGCGAACTTGTCCTGGGGGCCTATGCTGATCCGATACCCGCCGCCGGGCAGGTGCT

CGTCAAGACCAGAGCATGCGGCATCTGCGGATCTGACCTTCATTTTTGCGATCATGCGCAGGCGTTTACGAACCTTGCAT

CGCGGGCGGGTATCGCCTCTATGGAAGTTGATTTGTGTCGAGACATCGTTCTGGGGCATGAATTCTGTGGCGAGATTATG

GAGTTCGGGCCCTCTGCGGATCGTCGCTTCAAACCCGGACAGCTTGTGTGCTCGCTGCCGCTGGCGATCGGTCCGACCGG

AGCGCGGACGATTGGCTACTCGGATGAGTATCCCGGCGGGCTCGGCGAATATATGGTCCTCACGGAAGCGCTCTTGCTGC

CTGTTCCGAACGGCCTTCCGGCGACCTGCGCGGCGTTGACGGAGCCGATGGCGGTGGGATGGCATGCCGTCGAGATCGCG

CAGGTTCAACCACATCACATCCCTGTGGTGATCGGGTGCGGACCGGTCGGGTTGGCAGTCGTCGCTGCCCTGAAACATAA

GCAAGTTGCTCCGATTATTGCGTCGGATCCATCGCCCGATCGGCGTGCTCTTGCTCTGCGGATGGGCGCCGACGCCGTTG

TCGATCCGCGCGAAGAATCACCCTTTCGCCAGGCCGAGAAGATCGCACGCCCGGTCGGACAAGGTGGGGCCCTGTCCAGC

TCATTGCTGTCAAAGTCTCAAATGATATTCGAATGCGTAGGGGTGCCGGGCATGCTTCGGCATGCGATGGACGGCGCGTC

CGACGGGTCCGAGATCATGGTCGTTGGCGCATGCATGCAGCCGGACGCGATCGAGCCCATGATCGGGATGTTTAAAGCGC

TCACGATCAAATTCTCGCGAACTTACACGGGTGAGGAATTCGCCGCGGTGCTTCACATGATAGGTGAGGGCGCACTCGAC

GTATCTCCGCTCGTTACCGATGTGATTGGCCTGTCCGATGTCCCGTCCGCGTTTGAGGCTCTACGGAGTCCAGGCGCCCA

AGCAAAAGTGATTGTGGACCCTTGGCGCTGA

>Seq ID 18 (fumI)
ATGGCGAACGGAACAAGGCAGAAAGATCTCAGAGAACGCGCCGAACGGGTCATTCCGGGCGGGATGTACGGCCACGAGTCGACACG GTTGCTGCCGCCAGAATTCCCCCAGTTCTTCAGGCGCGCGCTGGGGGCACGAATTTGGGACGCCGACGAGCAGCCCTATATCGACT ATATGTGCGCGTATGGGCCAAATTTGCTCGGTTACCGGCAATCCGAAATCGAAGCCGCGGCTGATGCGCAGCGACTTCTCGGCGAC
```

```
ACCATGACCGGTCCTTCGGAGATCATGGTCAACCTCGCCGAAGCCTTTGTGGGCATGGTCCGTCATGCGGATTGGGCGATGTTCTG
CAAAAATGGCAGCGATGCCACCTCAACGGCGATGGTTCTCGCGCGTGCCCATACGGGGCGCAAAACCATATTATGCGCCAAAGGCG
CCTATCATGGCGCTTCCCCGTGGAACACTCCGCATACTGCCGGGATTCTCGCTTCCGATCGCGTGCATGTCGCATATTATACCTAT
AACGACGCCCAAAGCTTATCGGACGCGTTCAAGGCGCACGATGGCGATATTGCGGCTGTCTTTGCCACACCTTTCCGACACGAAGT
ATTTGAGGACCAGGCCCTCGCCCAGCTTGAGTTCGCGCGCACCGCTCGAAAATGTTGTGACGAGACCGGTGCGCTTCTGGTCGTTG
ACGATGTGCGCGCAGGTTTCCGGGTGGCGCGCGATTGCAGCTGGACGCATTTGGGTATCGAACCCGATCTCAGTTGCTGGGGAAAA
TGCTTTGCGAATGGCTATCCGATCTCCGCCCTGCTGGGCTCGAACAAGGCGCGCGATGCGGCGCGGGATATATTTGTGACCGGCTC
CTTCTGGTTCTCTGCGGTACCGATGGCGGCCGCGATCGAAACCCTCAGGATCATTCGAGAGACGCCTTATCTCGAAACGCTGATCG
CCAGCGGCGCCGCCCTGCGGGCAGGCCTGGAGGCACAGTCTCAGCGCCATGGTCTTGAGTTGAAGCAGACGGGCCCGGCGCAGATG
CCGCAAATATTCTTTGCGGACGATCCCGATTTTCGGATCGGCTATGCGTGGGCCGCGGCGTGCCTGAAGGGCGGCGTCTATGTTCA
TCCCTATCACAATATGTTTCTCTGCGGCCCATACAGTTGACGATGTAACGGAGACCCTCGAGGCGACGGATCGCGCGTTCAGCG
CGGTCCTCAGAGATTTTGCGTCTCTCCAGCCTCATCCCATTTTAATGCAACTCGCCGGTGCTTGA

>Seq ID 20 (fumJ)
ATGTATCGGAAGTTCAGAATCGAAAAGCCCGGCAAGGCAAATAGTTTGCTCGGCGCAGTAGCGCTCGGCACCCTCGCATTTCCTGT
CTCTGCCAGTGCTCAGGATAGCGATCCCGCATCGATAGGTCAGCCGGACGAAGCGGACACGGACCGGGGAACGAGCGAAATCGTCG
TGACCGGCAGCCGCCTCCAGAACGGCTTCAATTCGCCGACGCCGGTTACAGCCGTATCCAGCGAGCAGTTGAAGGAGGCATCTCCG
ACCAACCTTGCCGACGCACTCAACCAGCTGCCCGTGTTCAACGACAGCTTGAAGACCTCCAACCCTGGCACGACACCCGGAACGGG
GAACAGCGGTCAGAACCTGCTCAACATGCGCGGCCTCGGGTCAAACCGGAACCTCGTCCTGCTGAACGGCAACCGTTTCGTCGCGA
CCAATTTCACAGGCTCGGTCGATATCAACGTGCTGCCGCAGGCGTTGGTCAAGCGCGTCGATGTCGTGACGGGCGGCGCCTCGGCC
GCCTACGGTTCCGATGCCGTTTCGGGCGTCATCAACTTCGTGCTCGACGAAGATCTGGAAGGCATCAGGGCCGAGCTCCAGTCGGG
TGTTTCAACCCGCGGCGACCTCCCGTCCTACGGCGGTTCGATCGCCTTCGGCACTTCGTTTGCCGACGACCGGTTGCACTTGCTCG
GCAGCTTCGAATATTTTCGACAGGACGGAATCCGGGCCGATGAAGCAACGGGTCGCCGCTGGTTCGACATCGCCGCCGGCCAATAT
CCCGTGCCCGGCGCTACGACAGGCGTCACGGTCGTGCCCGATATTCGCAGTTCTCGCGGATCCTACGGCGGACTTGTCACGTCCGG
CCCTCTGAAAGGCATCGCGTTTTTGCCCGGAGGAGTCCTAGGGACCTTCGACTACGGGAATTTTACGAGCTCGTCGTTCCAGAGCG
GCGGCGATGGACCGCGCGTGAATATCGGCTTCGCCCCGGATCAGCTTCGCTACAACGCGTTCCTACGCGCCGCATATGATGTGTCC
GACACTGTGCAGGTGTATGCGGAGGGCACCTATGCTTATTCCCACACCAACCTGGGTGCATTCGTAATATCGCATGTCGGTGGCTC
GAATAATTTCCGGATCTTCCGTGATAACGCCTTCCTTCCGGCTCCACTCGCGACGCTCATGGACAGAAATGCCCAGGCTTCGATCG
TTGTCGGTCGCTTCTCAAGCGACTTTCCCTTGGTCGAAATCGAGAATTTCGCAAAGGTCTACCGCGCGCTGCCGGCTTCCGGGCA
GACATTGGCAATGGCTGGAAACTCGATGGCTCGGCCTCCTTTGGCCTTACGGACCTCGAGCTTCGTGAAAACAATCTCACCATCAA
CCGCAATCTCTACGCCGCCGTCGATGCGGTCCGCGATCCCGCGGGCAATATCGTCTGCCGTTCAACACTGGCCGCCTCGACCAAG
ATTGCGTGCCGCTCAATCTCTTCGGCACAGGCTCGCCGAGCGCGTCGGCCATCGACTATGTCACCGCTGATGGCGTCGCTCAGCTG
AGGCTTGAGCAATATGTGGCGGGACTCACGATTTCCGGCGACCTCGGCGATAGCCTGTCGTTCGGCGCGGGCCCGGTCTCGGTCGC
CGCTGGTATCGAATATCGCAAGGAGAAGGCCCGGCAGGAAACCGACGCGATATCGCAGGCGACGACCTCGATCACGGGAATCAGGG
GGGCTCCGGCGGCGCAGGCAGGTCGGCCTGGAGGCTTCAATCTCTACAACCCACTTCCCTTCTCGGGAAGCTATGACATCAAGGAA
GGTTTTGTCGAAATCGGCGTCCCGATTCTGAAGGACAGCGCGCTGGGACGTTCGCTGAACTTAAACGGCGCCGTCCGATATGCCGA
TTACAGCCAGTCCGGTGGAGTAACAACCTGGAAGCTGGGCGGAGAATATGAGCCGATCGACGGCCTCAGGTTCCGCGCGACCCGTT
CGCGAGATATCCGCGGGCCAAGCCTTGTCGAGCTATTCGACCCCGGCCGTCAGGCGACGCTCAATTCAATTTATGGCGGACAGGCT
GTGCAGACGCGGTTCTTTACCGCCGGCAACGCGGATTTGCGCCCTGAAAAGGCGGACGTCCTTACATTCGGCGCGGTGCTACGCCC
CGCCTTCGTGCCGGGGTTTCAGTTTTCGGTCGATCGCTATGTGGTGAAGGTGAAGGGCGCGATCGATTTCCTCCTTCCCCAGCAGG
AAATCGACGCGTGCGATGCAGGAAACACCTTCTTCTGCGACCTCATAACGGAGAATCCGGACGGCACCATCACAGTGACGGGTCCC
AATCTCAACCTGGCTGTCCAGAAAGCGGCGGGAATTGACTTCGAGGCCTATTACTCACGCCCCGTCGGCGGCGGCACGTTCAGTCT
```

```
TCGTGCGCTGGCAACGCACCATACCTCTGCCTATCGCATCGCGACCGGCTCGGCGCCCATCCGTTCGCTCGGACAACCGGACACGC

CAAAATGGTCGGCCAACTTCCAGGCGCGATATTCGACCGACGATTGGGCGCTTCTCGTGCAGCAGCGCTTCATCGCAGCATCGGTG

TTCAATGCCGACAATGTGGAGGGCGTCGATACGAATTTGAACCACGCTCCGGCGGTTTGGTACACCGACGCGACATTGACCTTCGA

CATCGCGGCTTTTGGCCAGAAGCAGCAGCTGTTTCTATCGGTCAATAATTTGTTCGACCGAGATCCGCCAATAGCGACGAACGACC

CCAGCAGTTTTTCCAGCCCGACCAGCTCTGCCTATGATCCGGTCGGCCGCTATTTTAATGTCGGGGTCCGTTTCCGGATCTGA
```

>Seq ID 22 (fumK) not complete
```
ATGCGCCTCACGGGCGGAGAATTATTGGCACGATGTTTGGCCGTCGAAGGCGTCCGGTATGTCTTCGGCCTCATGTCGCCGGAGGT GGATCCGCTCCTGGCTGCGCTCGAAGACAATGGGATATTGTTCGTCCCGGTGCGGCACGAGGCCGCCGCAGCCTATATGGCCGAGG GCATTTACAAGACCACCGGACAGGTCGCCGCGATTGTCACGAATCCGGGTCCCGGTACGGCAAACCTTCTGCCTGGAGTCGTGACG GCACGCCACGAAGGGGTTCCCTTCGTCGCAATAACGTCCCAGCATCAACTTGGTGTCGTTTATCCCTGCACGCCAAAAACCTTTCA GGGACAAGACCAGATCGACCTCTTTCGACCCGCGGTTAAATGGGGCGCACCCATCTTCGCCTGGAACCGGATTGTCGAAATCACCC ATATGGCGTTCCGGGAAATGTGGGCCGGCAGGCCGGGACCCGTTCAGTTGGAAATCCCGARGTCTGTGATGTATGKTGTGGGCGAA

CGAGGACCACGGTAGAAGTTTACRGATCGCCGACA . . .
```

>Seq ID 24
```
ATGGAATTGAGCCGCCAACGAGACCAGGCCTTGAGGGAGCGCGCCCAAGCGGTGATCCCGGGCGGGATGTACGGTCACGAGTCGAC

CTATCTGATGCCCGAGGGCACGCCACAGTTCTTCAGTCGCGGCAAAGGCGCCCGACTTTGGGACGCCGACGGCAACGAGTATGTCG

ATTACATGTGCGCCTATGGCCCCAACCTGCTGGGTTACGGCTTCGAACCCGTCGAAGCGGCCGCCGCAGCCCAGCAAGCCCGGGGC

GATACCCTGACCGGCCGTCGGAGGTGATGGTGCAGTTGGCGGAAGACTTCGTCGCGCAAATCAGCCACGCGGACTGGGCCATGTT

CTGCAAGAACGGCACAGACGCCACCTCAATGGCGATGGTCATCGCGCGCGCACACACCGGCCGGAAGACGATCCTCTGCGCGAAAG

GCGCCTATCATGGGCCGCGCCTTGGTGCACGCCGATCCTGGCCGGAACGCTACCGGAGGATCGCGCCTTTGTAGTCTACTACGAC

TACAATGACGCCCAAAGCCTCGTCGACGCCTTCGAGGCCCATCAGGACGACGTCGCGGCGATCTTCGCCACCCCTCACCGTCACGA

GGTGTTCAGCGACCAGATCGATCCTGATCCGGAATATGCGGCCAGCGTGCGGGCGCTCTGCGACAAGAGCGGCGCCCTGCTCGTCG

TCGACGAAGTTCGAGCCGGGTTCAGGATCGCGCGCGACTGCAGCTGGGCCAAGATCGGCGTCGCTCCGGATCTGAGCACCTGGGGC

AAGTGCTTCGCCAACGGCTATCCGATCTCGGCGGTCCTAGGGGGCGAAAAGGTGCGCAGCGCGGCAAAGGCCGTCTACGTCACCGG

CTCGTTCTGGTTCTCGGCCACGCCCATGGCCGCAGCCGTCGAAACCCTGAAGCAAATCCGCGAGACCGACTATCTCGAGCGGATCA

ACGCGGCCGGGACCCGCCTGCGCGAGGGCCTGCAGCAGCAGGCTGCTCACAACGGCTTTACGTTGCGCCAAACGGGGCCCGTCTCC

ATGCCCCAAGTCCTCTTCGAGGAAGATCCCGATTTTCGGGTCGGCTACGGCTGGGTTCGCGAATGCCTGAAGCGAGGGGTGTACTT

CAGCCCCTACCATAACATGTTCCTGTCGGCGGCCCATAGCGAGGCGGACCTGGCCAAGACCCTTGCGGCTACCGGCGACGCCTTCG

TCGAGCTACGCGCCAAGCTTCCGAGCCTAGAAATCCACCAACCCCTCCTCGCCCTGAGAGCGGCCTAA
```

Enzymes
Sequences:
>Seq ID 3 (FumA)
```
MRNVSDKAPPHETLTVVVAAMIVGTAALMVLGIQPILLGALVEEGRIPAEGLGSAATVEI

LAIAAGTCIGPVLMKTGYLRAKCAALCLMLAAINFGLTLPGFDLPIVACRAAAGALEGLS

LSAAILIMTHNRRPDRLSGIFLGAQTIPQVISAYLLPTEIIPRWGSAGGFTILGILAAIA

AIAALCLVDRVELDPTTVNDDLQWSPAAIVISMAAFVQFSGVGAAWSYLERLAAQHGFSG

ETIGIAISGSLLCQVGGAWLAAWIGGRVGYRFALIAGSLLQAGNVIALAVADQPSWFISA

SCAFGLFWLAMQPFQIRFAIAIDNSRQLAVLLTPIALVGLSAGPLLLSRFAGATDLRWIF

VGSSTLLLASALLYLCASLFQPRGKVIAETVDV
```

>Seq ID 5 (FumB)
```
MTSQVKLRSAAKRPRSPKSERGLARYESLLDATDRLLVDLDPDQVGLYQIAEEEAGASPSS

VYHFFPTKEVAHLALMRRYLEGLRNLDAMEVDIGQLESWQDLMKLDQIRARDYYNSHPPA

LKLLFGGYGGVEARKLDERYSEEIVSSMYGRYNGIFHMPQMENEALMFTICFAILDAVWA

VSFRRFGEITSDFLREGQAACIAYCRHYLPERTPSA
```

>Seq ID 7 (FumC)
VASKFNCELLDLRSFVAVYETRSFSHAARLLNQSQPALSRRIQRLESLVGGPLFERTSRS
LAETALGKELLPVAHRALELVDTSLFASPNVREFRWTDITIACVQTAAFHVLPRAARLYM
DQNPRVRLRILDVPAVEAADLVASGEAEFGISIESLLPSSLRFDALHEDPFGLACHRSHP
LASLEILEWTQLKGESLIAVHRASRNRTLLDAELARNNIALEWRYEVAHLTTALGLIDAQ
LGVAVMPRMVMPRSGRSEVVWRPVVAPVVQRTIGIVQRRTGSMHPAAQQLLARLRAAWSS
ANLGDIASREDGAS

>Seq ID 9 (FumD)
VKEHQCRGGRASPAAPATWLARISVSRGASAIAWTFMLGATAIPVAAQTDDPKLVRHTQS
GAVEGVEGDVETFLGIPFAAPPVGDLRWRPPAPPRAWAGTRDGRRFAPDCIGNERLREGS
RAAGTSEDCLYLNIWSPKQVGKGGLPVMIWVYGGGFSGGSGAVPYYDGSALAQKGVVVVT
FNYRAGILGFLAHPALSKESPNGVSGNYGLLDMLAAFKWVQNNIREFGGDPNRVTVFGES
AGASALGLLLTSPLSESAFNQAILQSPGLARPLATLSESEANGLELGADISALRRADAGE
LTKIAQSRIPMSRQFTKPRPMGPILDGYVLRTLDVDAFAKGAFRKIPVLVGGNADEGRAF
TDRLPVKTVLEYRAYLTEQFGDEADAWERCYPANSDADVPAAVARLFGDSQFNNGIELLS
AAFAKWRTPLWRYRFTGIPGAGRRPATHGDEIPYVFANLGPSSVSMFGSLEGGAGASDIK
LATEMSAAWVSFAVHGVPDQGTKSHWPRFERRGEIMTFGSQVGSGEGLGVSPSKACQPSK

>Seq ID 11 (FumE)
LEFRRAKPANPQNSARPVRASARRPALRATGCALCLEGSKLRYDVAIIGGGNAALTAAVT
AREAGASVLVIEHAPRAMRGGNSRHTRNMRTMHERPLSPLTGEYSADEYWNDLVRVTGGR
TDEELARLVIRNTTDAIPFMTRCGVRFQPSLSGTLSLSRTNAFFLGGGKALVNAYYATAE
RLGVDILYDSEVTEINLQQGVVQRLQLRSRGFPVEVEAKAAIASSGGFQANLDWLSSAWG
PAAANFIVRGTPYATGTVLKNLLEQGVASVGDPTQCHAVAIDGRAPKYDGGIVTRLDCVP
FSIVVNKDALRFYDEGEDVWPKRYAIWGRLVAQQPDQIAFSIIDRQAEDLFMPSVFPPVQ
ADTIAGLAEKLGLNPVTLERTVAEFNAACVPGEFGGQDLDDLHTEGIEPKKSNWARPIIV
PPFSAYPLRPGITFTYLGVKVDSRARVIMETGEPTKNLFASGEIMAGSILGQGYLAGFGM
AIGTVFGRIAGWEAARHAGF

>Seq ID 13 (FumF)
MQDFDLVKMLSDLPSAPELEARRVMEVCNACRYCEGFCAVFPAMTLQRHFASGDLSHLAN
LCHSCQGCYYACQYAPPHEFGINVPKALSELRLESYEQHAWPRPVAALYRKNALIISILS
AACITGVLLLAAIFNGDALFAKHASVPGGGFYNVIPYQAMIAVAATTFLYSALALAISLV
RFSRTIGLGIKVLYQHVPVLRALRDAATLRYLGGSDGEGCNDADETFSTTRRKFHHALAY
GFGLCFAATATGTIYDHMFGWPAPYALFSLPVVLGTVGGIGMVVGAIGLLWLKLAGEDAP
RSPALLGPDVALLVLLLAIAATGLLLLAVRSTEVMGVALAVHLGVVLAFFLVMPYSKFVH
GIFRLTALVRHHADREASNGFASSPPTKKG

>Seq ID 15 (FumG)
MEHMKSVRDRSSVMQIVRVASGNCLEQYDFFVYGFYAAYIARSFFPTGDNATSLMLSLAT
FGAGFLMRPLGAIFLGSYIDRVGRRKGLIVTLAIMAVGTLTIAMTPSYEAIGLLAPVIVL
VGRLLQGFSAGAESGGVSVYLAEIASPKSRGFFTSWQSASQQVAVMIAAAIGLALQSTLS
PEQMNDWGWRVPLLIGCLIIPVILWLRRSLPETKAYLHMEHKAHSIGESLRELQQSWGLI
LTGMAMSILTTTTFYMITAYTPTFGEKALGLSPQDVLLVTIMVGVSNFLWLPIGGALSDR
IGRTPILLVVPVTVLAIAFPLMSWLVAAPTFGALAAVLLTFSACFGLYNGALIARLTEIM
PPAIRTLGFSLAFSLATSLFGGFTPLVSTALIHATGSNSAPAIWLCFAAFISFVGVAAST

RLSRPIAEGAR

>Seq ID 17 (FumH)
MRAVVYRNGELVLGAYADPIPAAGQVLVKTRACGICGSDLHFCDHAQAFTNLASRAGIAS

MEVDLCRDIVLGHEFCGEIMEFGPSADRRFKPGQLVCSLPLAIGPTGARTIGYSDEYPGG

LGEYMVLTEALLLPVPNGLPATCAALTEPMAVGWHAVEIAQVQPHHIPVVIGCGPVGLAV

VAALKHKQVAPIIASDPSPDRRALALRMGADAVVDPREESPFRQAEKIARPVGQGGALSS

SLLSKSQMIFECVGVPGMLRHAMDGASDGSEIMVVGACMQPDAIEPMIGMFKALTIKFSR

TYTGEEFAAVLHMIGEGALDVSPLVTDVIGLSDVPSAFEALRSPGAQAKVIVDPWR

>Seq ID 19 (FumI)
MANGTRQKDLRERAERVIPGGMYGHESTRLLPPEFPQFFRRALGARIWDADEQPYIDYMC

AYGPNLLGYRQSEIEAAADAQRLLGDTMTGPSEIMVNLAEAFVGMVRHADWAMFCKNGSD

ATSTAMVLARAHTGRKTILCAKGAYHGASPWNTPHTAGILASDRVHVAYYTYNDAQSLSD

AFKAHDGDIAAVFATPFRHEVFEDQALAQLEFARTARKCCDETGALLVVDDVRAGFRVAR

DCSWTHLGIEPDLSCWGKCFANGYPISALLGSNKARDAARDIFVTGSFWFSAVPMAAAIE

TLRIIRETPYLETLIASGAALRAGLEAQSQRHGLELKQTGPAQMPQIFFADDPDFRIGYA

WAAACLKGGVYVHPYHNMFLSAAHTVDDVTETLEATDRAFSAVLRDFASLQPHPILMQLA

GA

>Seq ID 21 (FumJ)
MYRKFRIEKPGKANSLLGAVALGTLAFPVSASAQDSDPASIGQPDEADTDRGTSEIVVTG

SRLQNGFNSPTPVTAVSSEQLKEASPTNLADALNQLPVFNDSLKTSNPGTTPGTGNSGQN

LLNMRGLGSNRNLVLLNGNRFVATNFTGSVDINVLPQALVKRVDVVTGGASAAYGSDAVS

GVINFVLDEDLEGIRAELQSGVSTRGDLPSYGGSIAFGTSFADDRLHLLGSFEYFRQDGI

RADEATGRRWFDIAAGQYPVPGATTGVTVVPDIRSSRGSYGGLVTSGPLKGIAFLPGGVL

GTFDYGNFTSSSFQSGGDGPRVNIGFAPDQLRYNAFLRAAYDVSDTVQVYAEGTYAYSHT

NLGAFVISHVGGSNNFRIFRDNAFLPAPLATLMDRNAQASIVVGRFSSDFPLVEIENFAK

VYRGAAGFRADIGNGWKLDGSASFGLTDLELRENNLTINRNLYAAVDAVRDPAGNIVCRS

TLAGLDQDCVPLNLFGTGSPSASAIDYVTADGVAQLRLEQYVAGLTISGDLGDSLSFGAG

PVSVAAGIEYRKEKARQETDAISQATTSITGIRGAPAAQAGRPGGFNLYNPLPFSGSYDI

KEGFVEIGVPILKDSALGRSLNLNGAVRYADYSQSGGVTTWKLGGEYEPIDGLRFRATRS

RDIRGPSLVELFDPGRQATLNSIYGGQAVQTRFFTAGNADLRPEKADVLTFGAVLRPAFV

PGFQFSVDRYVVKVKGAIDFLLPQQEIDACDAGNTFFCDLITENPDGTITVTGPNLNLAV

QKAAGIDFEAYYSRPVGGGTFSLRALATHHTSAYRIATGSAPIRSLGQPDTPKWSANFQA

RYSTDDWALLVQQRFIAASVFNADNVEGVDTNLNHAPAVWYTDATLTFDIAAFGQKQQLF

LSVNNLFDRDPPIATNDPSSFSSPTSSAYDPVGRYFNVGVRFRI

>Seq ID 23 (FumK) not complete
MRLTGGELLARCLAVEGVRYVFGLMSPEVDPLLAALEDNGILFVPVRHEAAAAYMAEGIY

KTTGQVAAIVTNPGPGTANLLPGVVTARHEGVPFVAITSQHQLGVVYPCTPKTFQGQDQI

DLFRPAVKWGAPIFAWNRIVEITHMAFREMWAGRPGPVQLEIPXSVMYVVGERGPR-KFX

DRR . . .

>Seq ID 25
MELSRQRDQALRERAQAVIPGGMYGHESTYLMPEGTPQFFSRGKGARLWDADGNEYVDYM

CAYGPNLLGYGFEPVEAAAAAQQARGDTLTGPSEVMVQLAEDFVAQISHADWAMFCKNGT

-continued

```
DATSMAMVIARAHTGRKTILCAKGAYHGAAPWCTPILAGTLPEDRAFVVYYDYNDAQSLV

DAFEARQDDVAAIFATPHRHEVFSDQIDPDPEYAASVRALCDKSGALLVVDEVRAGFRIA

RDCSWAKIGVAPDLSTWGKCFANGYPISAVLGGEKVRSAAKAVYVTGSFWFSATPMAAAV

ETLKQIRETDYLERINAAGTRLREGLQQQAAHNGFTLRQTGPVSMPQVLFEEDPDFRVGY

GWVRECLKRGVYFSPYHNMFLSAAHSEADLAKTLAATGDAFVELRAKLPSLEIHQPLLAL

RAA-
```

According to a preferred further development, the method according to the invention is conducted in a manner that fumonisins are degraded in an oxygen-independent or anaerobic manner. By degrading the fumonisins in an oxygen-independent manner, it is feasible to further develop the method according to the invention to the effect that the nucleic acid sequences of genes or enzymes will perform the degradation reactions safely and reliably without any addition of molecular oxygen so as to make the thus produced additive usable in any oxygen-independent or anaerobic media where mycotoxins will possibly have to be degraded, such as, for instance, in foods for humans and animals, in the production of bioethanol, but also for the production of genetically modified agricultural crops.

According to a further development, the method according to the invention is conducted in a manner that, prior to the use of the enzymes in the vegetable starting material, the former are modified by molecular-genetic methods, mutagenesis or molecular evolution. By conducting the method in a manner that the enzymes, prior to their use in the vegetable starting material, are modified by molecular-genetic methods, mutagenesis or molecular evolution, it is feasible to produce the enzymes in an even more stable form adapted to the subsequent purpose of use so as to even further improve or perfect the oxygen-independent degradation of fumonisins.

According to a preferred further development of the invention, the method is conducted in a manner that the enzymes are isolated. By conducting the method in this manner, fumonisins, in particular, will be completely degraded in an oxygen-independent manner.

According to another preferred further development of the invention, the method is conducted in a manner that the enzymes are encapsulated in a protective coating. By encapsulating the enzymes in a protective coating, it is feasible to transport the enzymes to their destination of use, for instance, in particular, into the digestive tract without being changed and, in particular, degraded or damaged, so that the enzymes will not start acting before the dissolution of the protective coating, for instance in the gastrointestinal tracts of humans or animals, thus ensuring an even more selective, rapid and complete degradation of the mycotoxins in the oxygen-independent environment of the gastrointestinal tract while, at the same time, preventing fumonisins from exerting their noxious effects on living creatures which have taken in the same together with food.

According to a preferred further development, the method according to the invention is conducted in a manner that the enzymes are selected from permease ID No. 3, carboxylesterase ID No. 9, tricarballylate dehydrogenase ID No. 11, citrate utilization protein ID No. 13, alcohol dehydrogenase ID No. 17, aminotransferase ID No. 19 and/or acetolactate synthase ID No. 23. By conducting the method in this manner, fumonisins can be smoothly and completely degraded in an oxygen-independent environment. In this case, the transcription of the open reading frames in the FUM gene clusters isolated from the gene cluster of the nucleic acid sequence ID No. 1, which is derived from a prokaryotic strain having the accession number DSM 16254, is controlled by a bidirectional promoter located between FumA and FumI, as is apparent from Table 1 below. The clusters encode proteins which are involved in the regulation of the gene expression, like e.g. FumB and FumC, in the sampling of the substrate and its transport, like e.g. FumA, FumJ, FumG, and in the catabolism of the substrate, like e.g. FumD, FumE, FumF, FumH, FumI, FumK. From these nucleic acid sequences which encode special genes and enzymes, those genes were selected according to a preferred further development of the method according to the invention, which are responsible for the catabolism of the substrate, thus enabling the respectively formed enzymes to completely catabolise the substrate, i.e. fumonisins.

In this case, open reading frames selected, for instance, from the gene cluster of the nucleic acid sequence having ID No. 1 are expressed in prokaryotic or eukaryotic host cells. The transcription of the open reading frames contained in the gene cluster having SEQ ID No. 1, in the bacterial strain with the accession number DSM 16254, takes place in a manner controlled by a bidirectional promoter located between fumA and fumI, as is apparent from the annexed FIG. 1. The genes encode proteins which are involved in the regulation of the gene expression, like e.g. FumB and FumC, in the recognition of the substrate and its transport, like e.g. FumA, FumJ, FumG, and in the catabolism of the substrate, like e.g. FumD, FumE, FumF, FumH, FumI and FumK.

In the Table 1 below, the designations of the genes of the fumonisin-catabolized gene cluster are listed, wherein O indicates the orientation, namely f forward and r reverse.

TABLE 1

| Gene | Sequence ID | O | Start | Stop | Length | Designation |
|---|---|---|---|---|---|---|
| fumA | 2 | f | 5214 | 6395 | 1182 | permease |
| fumB | 4 | f | 6418 | 7068 | 651 | tetR-type transcription regulator |
| fumC | 6 | f | 7232 | 8176 | 945 | lysR-type transcription regulator |
| fumD | 8 | f | 8294 | 9916 | 1623 | carboxylesterase |
| fumE | 10 | f | 9876 | 11378 | 1503 | tricarballylate dehydrogenase |
| fumF | 12 | f | 11494 | 12537 | 1044 | citrate utilization protein B |

TABLE 1-continued

| Gene | Sequence ID | O | Start | Stop | Length | Designation |
|------|-------------|---|-------|-------|--------|-------------|
| fumG | 14 | f | 12541 | 13836 | 1296 | tricarballylate proton symport |
| fumH | 16 | f | 13957 | 15027 | 1071 | alcohol dehydrogenase |
| fumI | 18 | r | 5063 | 3795 | 1269 | aminotransferase |
| fumJ | 20 | r | 3513 | 679 | 2835 | TonB-dependent receptor |
| fumK | 22 | r | 551 | ? | ? | acetolactate synthase (partial) |

By preferably conducting the method according to the invention in a manner that an enzyme is used, which comprises at least 90% sequence identity with at least one of the enzymes having ID No. 3, 5, 7, 9, 11, 13, 15, 17, 19, 21, 23 or 25, an even more complete degradation of the fumonisins will be ensured, whereby not only fumonisins but also related or structurally similar mycotoxins will, at the same time, be completely detoxified, particularly in anaerobic or oxygen-independent environments, such as e.g. AAL-toxin.

By preferably conducting the method in a manner that, when using aminotransferase ID No. 19, an α-keto acid is used as a cosubstrate, it is possible, in particular with the degradation of the amino group of fumonisin and the simultaneous use of an α-keto acid such as, e.g., pyruvic acid, to substitute a keto group for the amino group on the fumonisin molecule with alanine forming as a side product of this reaction, which is totally harmless, thus ensuring the complete degradation of fumonisins to harmless substances.

According to a preferred further development, the method according to the invention may also be conducted in a manner that, when using carboxylesterase ID No. 9, at least one adsorbent selected, in particular, from clay minerals is additionally used. By additionally using at least one adsorbent selected, in particular, from clay minerals when using carboxylesterase ID No. 9, it is possible to render fumonisins totally harmless even without the addition of any further enzymes, by cleaving the two tricarballylic acid side chains by the carboxylesterase from the fumonisin molecule in a first step and forming what is called hydrolyzed fumonisin. Hydrolyzed fumonisin, which is a substantially chain-like molecule, can subsequently be adsorbed, for instance, on clay minerals so as to enable fumonisins to be rendered completely harmless even in a one-step enzymatic degradation process.

According to a preferred further development, the method according to the invention is conducted in a manner that the thus produced additive is used in a vegetable starting material to be fermented or in a mash for the production of bioethanol. By using the additive produced by the method according to the invention in a vegetable starting material to be fermented or in a mash for the production of bioethanol, it is feasible to free coproducts occurring in the production of ethanol, namely pomace, i.e. the dried grain residues and undissolved components, or dried vinasse (dried distiller's grains with solubles—DDGS) from fumonisins or mycotoxins, particularly in an oxygen-independent environment.

The invention further aims to provide an additive for the enzymatic degradation of fumonisins, by which it is feasible in a safe and reliable manner to degrade or detoxify such mycotoxins, in an oxygen-independent environment.

To solve these objects, an additive of this type is characterized in that it contains at least one enzyme of the sequences ID Nos. 3, 5, 7, 9, 11, 13, 15, 17, 19, 21, 23 and 25 as well as optionally, in addition, at least one cosubstrate for at least one or several of the used enzymes, and an inert carrier.

Such an additive which contains at least one enzyme or a complete recombinant host organism for the expression of said enzyme as well as optionally, in addition, at least one cosubstrate for at least one or several of the used enzymes, and an inert carrier, excels by selectively degrading, and hence detoxifying fumonisins. The use of an additive according to the invention, which essentially consists of isolated enzymes as well as, optionally, their cosubstrates and carriers, offers the advantage that the former will keep their catalytic activities in an environment and under conditions in which, for instance, complete microorganisms would not or hardly be active, while, at the same time, allowing for significantly higher specific activities and the catalyzation of defined reactions with the avoidance of undesired side reactions.

In addition, problems caused according the prior art on agricultural raw products by the use of reproducible germs will be safely avoided, and additives merely containing isolated enzymes will, moreover, provide an enhanced formulation aptitude for a selective and controlled activation, i.e., for instance, in a particular site of the digestive tract, as well as the avoidance of an undesired, elevated consumption of substrate. In order to further enhance this specificity, the additive according to the invention is preferably further developed to the effect that enzymes modified by molecular-genetic methods, mutagenesis or molecular evolution are used.

According to a preferred further development, the additive is designed such that an enzyme is used, which comprises at least 90% sequence identity with an enzyme having ID No. 3, 5, 7, 9, 11, 13, 15, 17, 19, 21, 23 or 25. When using an enzyme which comprises at least 90% sequence identity with an enzymes having ID No. 3, 5, 7, 9, 11, 13, 15, 17, 19, 21, 23 or 25, it is feasible to safely and reliably degrade in an oxygen-independent manner even further mycotoxins besides the fumonisins to be preferably degraded, thus enabling the extensive detoxification of the fumonisins present, for instance, on vegetable raw products.

By designing the additive in a manner that the enzymes, modified enzymes and/or at least 90% identical enzymes are used sheathed with a protective coating, as in correspondence with a preferred further development of the invention, it will be safeguarded that the enzymes, the at least 90% identical enzymes or the modified enzymes will be secured against any premature loss of activity so as to safely and reliably develop their action in the intended site, for instance in the gastrointestinal tract.

By preferably further developing the additive in a manner that the enzymes are selected from carboxylesterase ID No. 9, tricarballylate dehydrogenase ID No. 11, citrate utilization protein ID No. 13, alcohol dehydrogenase ID No. 17, aminotransferase ID-No. 19 and/or ID No. 25, and/or acetolactate synthase ID No. 23, enzymes qualified for substrate catabolism will be substantially applied so as to ensure, in addition to a reduced amount of enzymes to be applied, that no undesired side reaction will occur when using said enzymes.

According to a preferred further development of the invention, the additive is designed such that it contains a carboxylesterase ID No. 9, an aminotransferase ID No. 19 or ID No. 25, an α-keto acid as a cosubstrate and an inert carrier. By the additive containing a carboxylesterase, an aminotransferase, an α-keto acid as a cosubstrate besides an inert carrier, it is, in particular, feasible to initially hydrolyze fumonisins contained in foods by cleaving tricarballylic acid residues from the fumonisins using carboxylesterase, and to subsequently further react the thus hydrolyzed fumonisin under the action of the aminotransferase and α-keto acid as a cosubstrate, preferably pyruvic acid in the present case, by substituting a keto group for an amino group of the hydrolyzed fumonisin molecule so as to form a 2-keto-hydrolyzed fumonisin, which is totally harmless, for instance, for mammals and can be excreted unchanged, and alanine as a side product, which too does not exert or have any negative effects, for instance, on organisms.

According to a preferred further development of the invention, the additive is further developed such that it contains a carboxylesterase ID No. 9, at least one adsorbent like a clay mineral as well as, optionally, an inert carrier. When using but one carboxylesterase ID No. 9 and at least one adsorbent, the detoxification of the fumonisins may also be performed in a manner that only the tricarballylic acid residues are cleaved and the thus formed, hydrolyzed fumonisin is adsorbed on said adsorbent. By cleaving the tricarballylic acid residues by the aid of carboxylesterase, a substantially long-chain molecule is formed, which can be readily and reliably adsorbed so as to ensure the complete detoxification merely by the selected use of a single enzyme, in particular, by the oxygen-independent degradation of fumonisin and subsequent adsorption.

In that, as in correspondence with a further development of the invention, the additive is used in an oxygen-independent environment during the production of bioethanol, in particular along with a mash or a vegetable starting material, by selecting the additive such that the enzymes contained therein are completely derived from bacteria catalyzing the catabolism of fumonisins via a highly specific degradation path, it is feasible to use the same with high specificity, activity and efficiency so as to enable the additive to be also used technologically in an oxygen-independent environment.

Finally, the present invention relates to the use of genes as represented in the sequences, or of complete recombinant host organisms for the expression of gene sequences having ID Nos. 1, 2, 4, 6, 8, 10, 12, 14, 16, 18, 20, 22 and 24 as well as, optionally, of cosubstrates for producing an additive for the degradation of fumonisins, in the processing or use of vegetable raw materials. An additive produced in this manner allows for the complete and reliable degradation of fumonisins, particularly in an oxygen-independent environment.

In a preferred manner, a cosubstrate selected from the group consisting of a carboxylesterase ID No. 9, an aminotransferase ID No. 19 or ID No. 25, or an α-keto acid, and an inert carrier are used according to the invention, which use allows for the safe and reliable degradation to harmless components of the total of fumonisins in, for instance, vegetable raw materials or starting materials.

A further preferred use is characterized in that a carboxylesterase, at least one adsorbent, in particular clay mineral, as well as, optionally, an inert carrier are used. When using a carboxylesterase and at least one adsorbent, it is feasible to safely and reliably detoxify fumonisins by the mere use of a single enzyme in that the tricarballylic acid side residues are cleaved from the fumonisin by, or by the aid of, said enzyme and the thus formed long-chain hydrolyzed fumonisin is subsequently adsorbed on the adsorbent so as to render the toxin harmless in a safe and reliable manner.

According to a preferred use, the additive according to the invention is used for the oxygen-independent or anaerobic treatment of a vegetable starting material or a mash in the production of bioethanol. In this case, it is feasible to safely and reliably render the mycotoxins contained in the vegetable starting material or raw material harmless during the production of bioethanol in an oxygen-independent environment so as to subsequently allow for the use of the residue from ethanol production, namely the pomace or dried vinasse, either directly or after drying and pelletizing without further processing and, in particular, detoxification as a feed that is free of fumonisins.

In the following, the invention will be explained in more detail by way of exemplary embodiments and Figures. Therein:

Figures 1, 2:
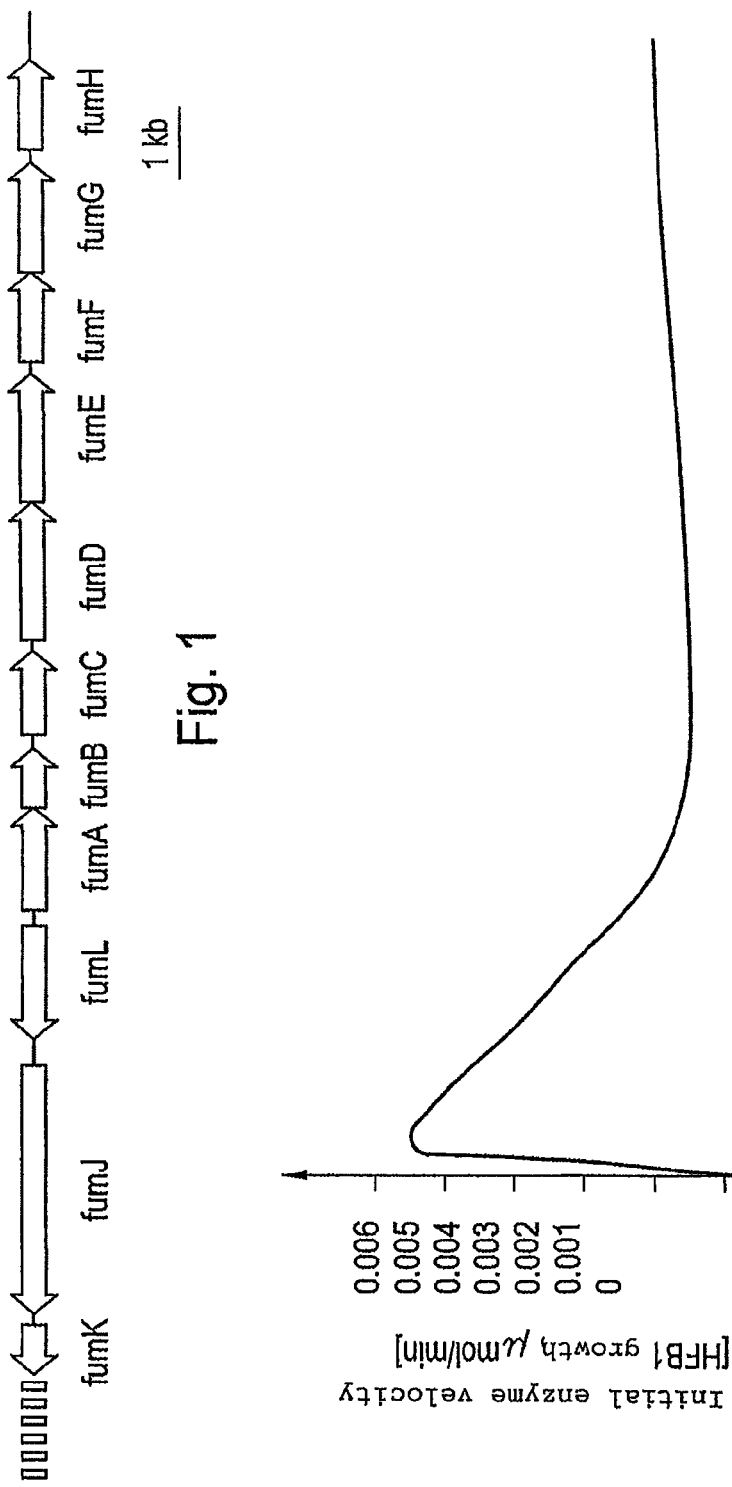
FIG. 1 depicts the fumonisin-catabolic gene cluster.
FIG. 2 illustrates the Michaelis-Menten curve for fumonisin carboxylesterase FumD.

FIG. 1 depicts a fumonisin-catabolic gene cluster as a partial sequence of 15420 base pairs of a microbial strain having the accession number DSM 16254. In the fum-gene cluster of the prokaryotic strain DSM 16254, the transcription of the open reading frame is controlled by a bidirectional promoter located between fumA and fumI. The cluster encodes proteins involved in the regulation of the gene expression, like e.g. FumB and FumC, in the recognition of the substrate and its transport, like like e.g. FumA, FumJ, FumG, and in the catabolism of a substrate, like e.g. FumD, FumE, FumF, FumH, FumI and FumK.

EXAMPLES

Example 1

The Enzyme Kinetics of Fumonisin Carboxylesterase

The fumD gene (sequence ID No. 8), which encodes a fumonisin carboxylesterase, was cloned and expressed in *Pichia pastoris* using standard procedures. The his-tagged enzyme was recovered and purified from the supernatant culture solution by affinity chromatography. The enzyme concentration was determined and the enzyme-kinetic parameters were determined with seven different substrate concentrations ranging from 50 µg to 25 mg $FB_1$ per liter and an enzyme concentration of 0.33 ng/ml. The reactions were buffered in 20 mM Tris-Cl buffer (pH 8.0) with 0.1 mg/ml bovine serum albumin and incubated at 30° C. Samples were taken after 0, 30, 60, 120 and 240 minutes of incubation and analyzed by HPLC-MS/MS. Fumonisin $B_1$ ($FB_1$) and hydrolyzed fumonisin $B_1$ were quantified, based on a calibration with the purified reference substances and a completely $^{13}C$-labelled internal $FB_1$-standard.

FIG. 2 illustrates the Michaelis-Menten curve for the hydrolysis of fumonisin $B_1$ ($FB_1$) by fumonisin carboxylesterase FumD, which was determined at an enzyme concentration of 0.33 ng/ml in Tris-Cl buffer (pH 8.0), with initial enzyme speeds having been plotted against the substrate concentrations. The Michaelis-Menten curve shows a drop at higher substrate concentrations, since the enzyme speed was calculated based on the product, i.e. the formation of hydrolyzed $FB_1$. Since hydrolyzed $FB_1$ is formed from $FB_1$ in a two-step reaction via partially hydrolyzed $FB_1$ with but one tricarballylic acid side chain which was retained and a side chain which was cleaved, the formation of the end product was delayed at high substrate concentrations. The Michaelis-Menten constant $K_M$ was calculated as 0.90 µmol/l, which was equivalent to 650 ppb, and the conversion rate was 900 per second.

From FIG. 2 results that fumonisins can be rapidly and completely hydrolyzed with the carboxylesterase in the relevant concentration ranges.

Example 2

The Catalytic Activity of HFB1 (Hydrolyzed Fumonisin B1) Aminotransferase

Figure 3:
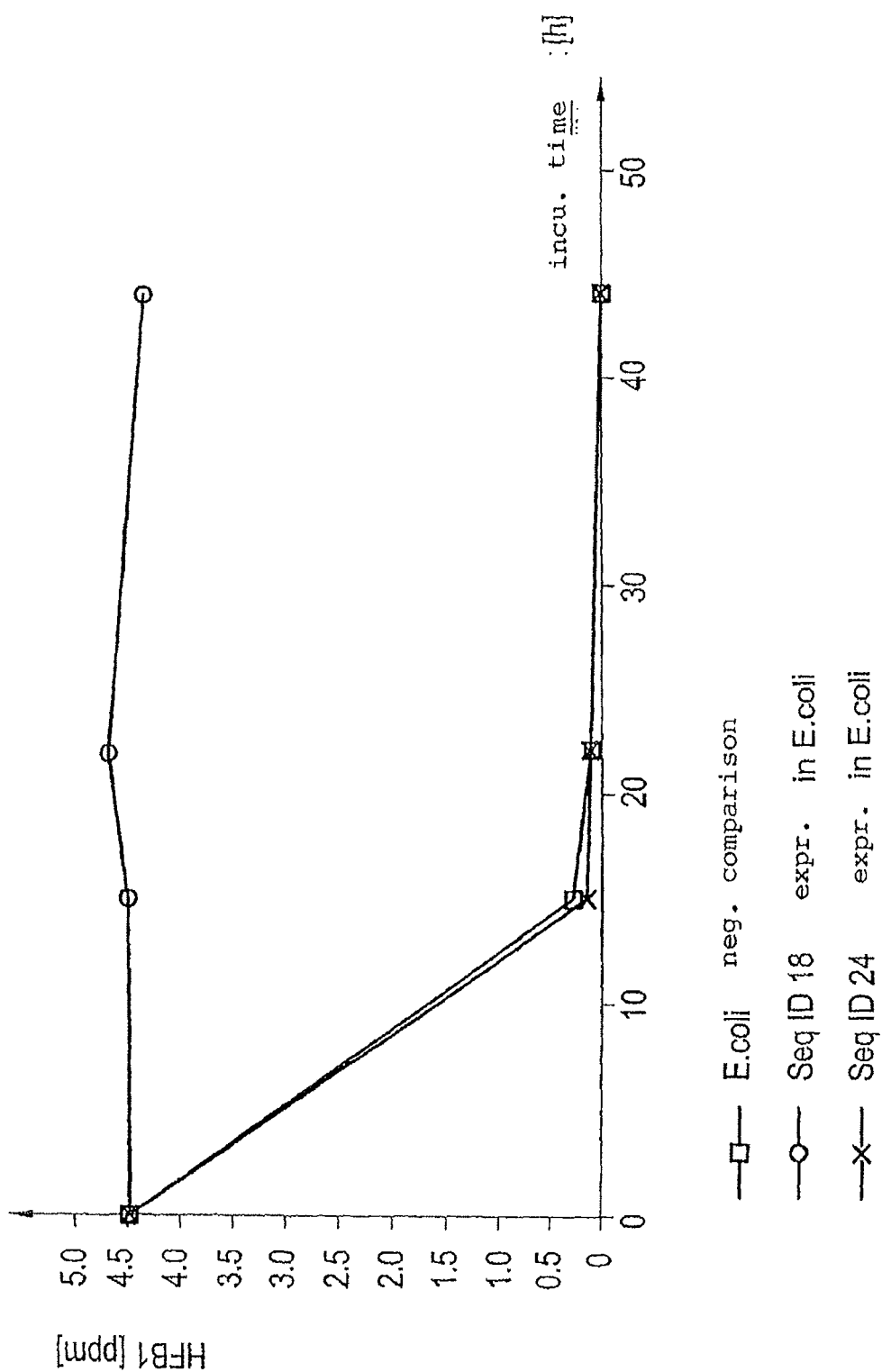
FIG. 3 shows a degradation curve of hydrolyzed fumonisin $B_1$.
Figure 4:
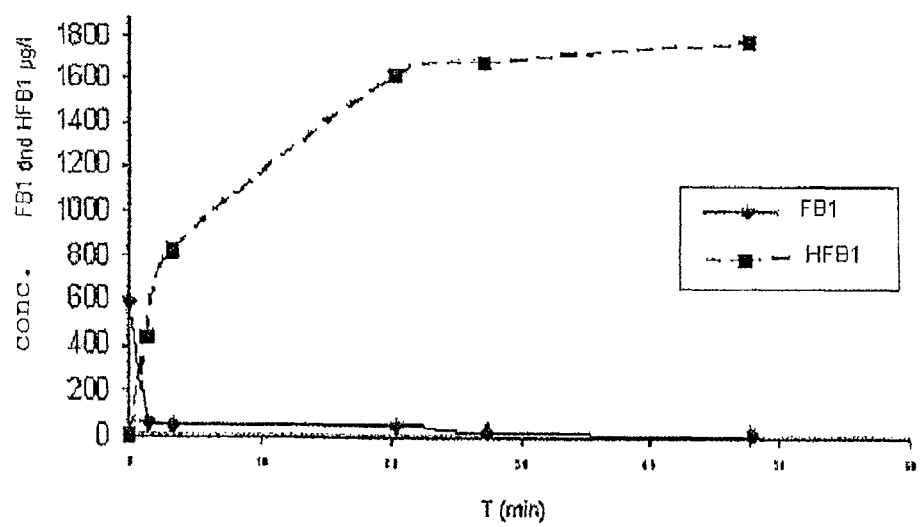
FIG. 4 illustrates the conversion of fumonisin FB1 into hydrolyzed fumonisin HFB1 after the addition of carboxylesterase ID No. 9.
Figure 5:
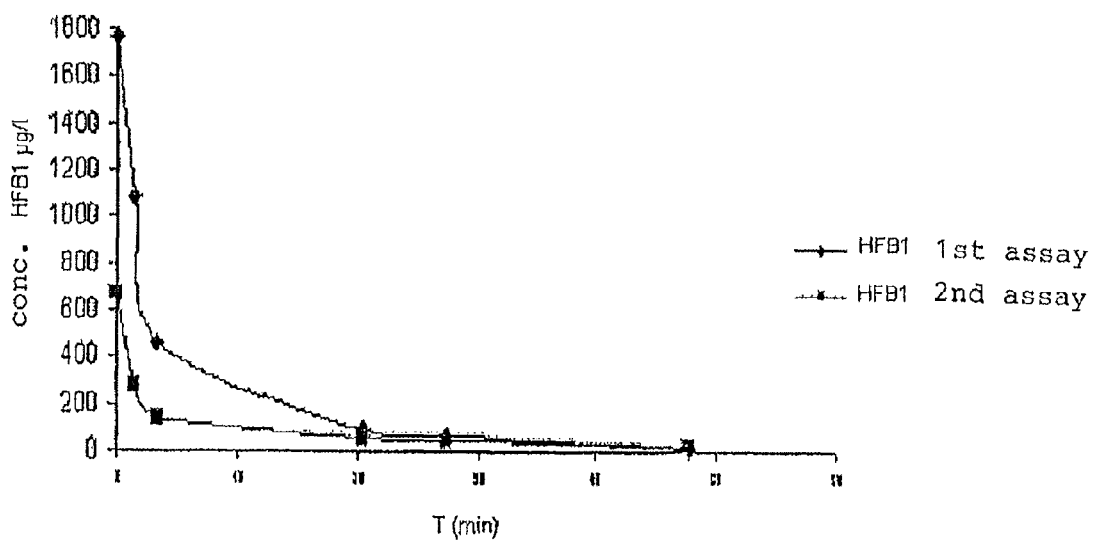
FIG. 5 illustrates the degradation of hydrolyzed fumonisin HFB1 by the addition of aminotransferase ID No. 19.

Sequences ID Nos. 18 and 24 were cloned using standard procedures and expressed in E. coli under the control of a bacteriophage T7 promoter. The bacterial cells were collected, resuspended in 50 mM sodium phosphate buffer and lyzed under ultrasonic action. Hydrolyzed fumonisin was added, and the samples were incubated at 25° C. Samples were taken at time intervals and analyzed by HPLC-MS/MS. No reduction of the hydrolyzed $FB_1$ concentration was observed. When a cosubstrate such as, for instance, an α-keto acid like e.g. pyruvic acid, or oxalacetate was added to the reaction, the complete degradation of the hydrolyzed fumonisin to 2-keto-$HFB_1$ could be observed as illustrated in FIG. 3. This substance is totally harmless for mammals.

Example 3

Enzyme Activity in the Intestinal Environment

To examine the enzymatic activity of FUM-carboxylesterase in the digestive tract, freshly butchered swine guts were used and transported to the lab under oxygen-exclusion and examined in an anaerobic sterile bench. Approximately 10-cm-long pieces of duodenum and jejunum were secured and cut out. Fumonisin B1, diluted to a final concentration of about 10 ppm in a concentrated aqueous solution, was injected by needles and mixed with intestinal contents. After this, 5 μg fumonisin carboxylesterase in an aqueous solution, or the same volume of water in the negative controls, respectively, was injected and incorporated. The intestinal sections were incubated at 39° C. Samples were drawn by the aid of needles and analyzed by HPLC-MS/MS. It was shown that, at the time of the first sampling after two hours, fumonisin B1 had already been completely hydrolyzed in the duodenum and jejunum.

Example 4

Determination of the Temperature Range of the Activity of Fumonisin Carboxylesterase To determine the temperature range in which fumonisin carboxylesterase is active, 1.6 ng/ml FUM-carboxylesterase in 20 mM Tris-Cl buffer, pH 7.0, was incubated with 0.1 mg/ml BSA and 10 ppm fumonisin B1 at different temperatures. It was shown that the temperature optimum for the enzyme was 30° C. Enzymatic activity was still clearly determined at 40° C. and even 50° C. FUM-carboxylesterase is, thus, suitable for application under the temperature conditions prevailing in the digestive tract, or in the course of process steps in the production of foods and feeds, which take place at elevated temperatures.

Example 5

Determination of the pH Range of the Activity of Fumonisin Carboxylesterase

To determine the pH range in which fumonisin carboxylesterase is active, Teorell-Stenhagen buffer was used. This buffer can be adjusted over a range of 10 pH units with the same buffer capacity by the combination of citrate, phosphate and borate. FUM-carboxylesterase was incubated in this buffer with 10 ppm fumonisin B1 at different pH values and 25° C., at a concentration of 3.3 ng/ml. The highest activity was shown at pH 8.0, yet activity could be determined in the whole range from pH 5 to pH 10. This activity within this broad pH range has enabled the technological application of the enzyme as a feed additive or in the course of food and feed processing.

Example 6

Feeding Test with Piglets

The test was performed in a test stable with 12 stalls for 10 animals each. The stable was equipped with a slatted floor, pan troughs and a computer-controlled feeding system. The automats were arranged along the stall walls. Every day, the stable climate was automatically recorded, and the temperature was set according to the standard recommendations for piglet breeding.

For this test, 120 mixed-sex weaned pigs (age: about 4 weeks, average setting weight: 8.21 kg) were used. Each piglet was earmarked and individually weighed. The 120 piglets were randomly distributed among 12 stalls. All piglets came from the Austrian Breeding Program ÖHYB (=(large white×landrace)×Pietrain).

Immediately upon weaning, the piglets were fed with a starter feed for two days, after this settling-in period the changeover to the test feed took place. Feeding was effected in two phases: Weaning phase days 1-14, breeding phase days 15-42. The test feed was mixed individually per stall via the spotmix feeding installation and allotted in dry form twice a day as a function of the number of piglets, weight development and feed consumption. Water was available ad libitum. The 12 stalls were divided into four different application groups at three repetitions each and received the following admixtures in the above-described feed:

| Group | |
|---|---|
| Negative control | no toxins, no enzyme addition |
| Positive control | 4-5.5 ppm fumonisin B1 |
| Test group 1 | 4-5.5 ppm fumonisin B1 + enzyme mix 1 (carboxylesterase, aminotransferase, pyruvate) 0.5 kg/t feed |
| Test group 2 | 4-5.5 ppm fumonisin B1 + enzyme mix 1 (carboxylesterase, aminotransferase, pyruvate, inert carrier) 1 kg/t feed |

Respiratory problems were observed in the positive control with almost half of the animals, even one dropout occurred. All other groups appeared healthy.

Performance Data

| Group | Number of animals | Starting weight (average, kg) | Final weight (average, kg) | Drop-outs |
| --- | --- | --- | --- | --- |
| Negative control | 30 | 8.34 | 26.82 | |
| Positive control | 30 | 8.17 | 24.77 | 1 |
| Test group 1 | 30 | 8.08 | 26.69 | |
| Test group 2 | 30 | 8.25 | 27.03 | |

Example 7

Enzymatic Degradation of Fumonisins in Bioethanol Mash

Samples of corn mash for the production of bioethanol were taken and incubated at 30 to 65° C. under stirring, the degradation of fumonisin B1 having been investigated after the addition of 770 units of carboxylesterase ID No. 9 per cubic meter of mash under stirring (stirring time in minutes). Samples were inactivated by boiling-up after having been taken and subsequently centrifuged for analysis, and an aliquot of the supernatant was evaporated. The residue was taken up in 200 µl sample buffer containing $C^{13}$-labelled internal fumonisin standard, shaken for 1.5 min, centrifuged off, and then subjected to LC-MS-analysis. From this results that, as illustrated in FIG. 4, fumonisin FB1 is completely converted into hydrolyzed fumonisin HFB1. After the addition of aminotransferase ID No. 19, the hydrolyzed fumonisin HFB1 is completely degraded to harmless components as illustrated in FIG. 5.

Example 8

Degradation of Fumonisins and their Derivatives in Corn Tortilla Mush and Cornflake Mush The activity of the fumonisin-degrading enzymes was examined in corn mush samples (corn grits) for the production of corn tortillas and cornflakes, Fumonisin-contaminated corn (about 1 ppm) was ground to corn flour, mixed with water and boiled up. For the production of tortillas, the corn mush cooled to about to 60° C. was supplemented with a mixture of proteinases in alkaline solution. After 30 to 180 min, when the pH had fallen below 9, preferably below 8, a mixture of carboxylesterase and aminotransferase (500-1000 U/$m^3$ each) was added and incubated for further 30 to 60 min. Concerning the production of cornflakes, a corn mush of ground corn and barley malt was boiled up in a pressure vessel for about one hour; after cooling to below 60° C. (preferably 50° C.), an enzymatic mixture comprising carboxylesterase and aminotransferase (500-1000 U/$m^3$ each) was added and incubated for further 30 to 60 min. Samples were then drawn from this mixture and examined for FB1 and HFB1 residues as in Example 7. HFB1 levels were below 80 ppb in all of the samples, the HFB1 formed of FB1 apparently had been continuously further reacted. The measured values for FB1 are indicated in the Table below.

TABLE

Enzymatic degradation of FB1 and HFB1 in corn mush; fumonisin concentration in ppb (µg/kg)

| Treatment time with enzyme mix (min) | Tortilla mush (40° C., 500 units) | Tortilla mush (50° C., 1000 units) | Cornflake mush (35° C., 500 units) | Cornflake mush (40° C., 1000 units) |
|---|---|---|---|---|
| 0 | 852 | 866 | 912 | 1053 |
| 10 | 116 | 134 | 51 | 97 |
| 30 | 32 | 71 | 17 | 37 |

The invention claimed is:

1. An additive for the enzymatic degradation of mycotoxins including fumonisins in vegetable raw materials and mixtures containing vegetable raw materials, wherein the additive comprises the enzyme of SEQ ID NO: 9 having mycotoxins degradation activity and optionally SEQ ID NO: 19 having mycotoxins degradation activity, in addition, at least one cosubstrate for the enzyme, and an inert carrier.

2. The additive according to claim 1, wherein the enzymes are used sheathed with a protective coating.

3. The additive according to claim 1, wherein it contains a carboxylesterase of SEQ ID NO: 9, at least one aminotransferase of SEQ ID NO: 19, an α-keto acid as a cosubstrate and an inert carrier.

4. The additive according to claim 1, wherein it contains a carboxylesterase of SEQ ID NO: 9, at least one adsorbent, in particular at least one clay mineral, as well as, optionally, an inert carrier.

5. The additive according to claim 1, wherein the additive is used in an oxygen-independent environment during the production of bioethanol along with a mash or a vegetable starting material.

6. An additive for the enzymatic degradation of mycotoxins including fumonisins in vegetable raw materials and mixtures containing vegetable raw materials, wherein the additive comprises the enzymes of SEQ ID NO: 9 and SEQ ID NO: 19 having mycotoxins degradation activity, in addition, at least one cosubstrate and an inert carrier.

7. A method for producing an additive for the enzymatic degradation of mycotoxins including fumonisins in vegetable raw materials and mixtures containing vegetable raw materials, wherein at least one nucleic acid sequence of genes corresponding to sequences of SEQ ID NOs: 8 and 18 is provided, the at least one nucleic acid sequence is expressed in prokaryotic or eukaryotic host cells, and at least one thus prepared enzyme corresponding to sequences of SEQ ID NOs: 9 having mycotoxins degradation activity and 19 having mycotoxins degradation activity optionally with a cosubstrate, are used in a vegetable raw material.

8. The method according to claim 7, wherein the fumonisins are degraded in an oxygen-independent manner.

9. The method according to claim 7, wherein the enzymes are isolated.

10. The method according to claim 7, wherein the enzymes are encapsulated in a protective coating.

11. The method according to claim 7, wherein the enzymes are carboxylesterase of SEQ ID NO: 9 and aminotransferase of SEQ ID NO: 19.

12. The method according to claim 7, wherein, when using at least one aminotransferase of SEQ ID NO: 19, a ketone is used as a cosubstrate.

13. The method according to claim 7, wherein, when using carboxylesterase of SEQ ID NO: 9, at least one adsorbent selected from clay minerals is additionally used.

14. The method according to claim 7, wherein, the additive is used in a vegetable starting material to be fermented or in a mash for the production of bioethanol.

* * * * *

UNITED STATES PATENT AND TRADEMARK OFFICE
CERTIFICATE OF CORRECTION

PATENT NO. : 8,703,460 B2  
APPLICATION NO. : 12/998061  
DATED : April 22, 2014  
INVENTOR(S) : Moll et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 36 days.

Signed and Sealed this

Twenty-ninth Day of September, 2015

Michelle K. Lee
*Director of the United States Patent and Trademark Office*